(12) United States Patent
Perrine et al.

(10) Patent No.: US 9,018,176 B2
(45) Date of Patent: Apr. 28, 2015

(54) INDUCERS OF HEMATOPOIESIS AND FETAL GLOBIN PRODUCTION FOR TREATMENT OF CYTOPENIAS AND HEMOGLOBIN DISORDERS

(76) Inventors: Susan Perrine, Weston, MA (US); Douglas V. Faller, Weston, MA (US)

( * ) Notice: Subject to any disclaimer, the term of this patent is extended or adjusted under 35 U.S.C. 154(b) by 0 days.

(21) Appl. No.: 13/310,199

(22) Filed: Dec. 2, 2011

(65) Prior Publication Data
US 2015/0018290 A1 Jan. 15, 2015

Related U.S. Application Data

(60) Provisional application No. 61/419,016, filed on Dec. 2, 2010.

(51) Int. Cl.
| | |
|---|---|
| A61K 31/165 | (2006.01) |
| A61K 31/435 | (2006.01) |
| A61K 31/4406 | (2006.01) |
| A61K 31/704 | (2006.01) |
| A61K 31/7135 | (2006.01) |
| A61P 7/00 | (2006.01) |
| A61P 7/06 | (2006.01) |
| A61K 31/473 | (2006.01) |

(52) U.S. Cl.
CPC .................................... *A61K 31/473* (2013.01)

(58) Field of Classification Search
USPC ..................................................... 514/24, 43
See application file for complete search history.

(56) References Cited

U.S. PATENT DOCUMENTS

| | | | | |
|---|---|---|---|---|
| 2001/0027215 | A1* | 10/2001 | Perrine | 514/557 |
| 2007/0232528 | A1* | 10/2007 | Franke | 514/9 |
| 2009/0137567 | A1 | 5/2009 | Perrine et al. | |
| 2011/0015168 | A1 | 1/2011 | Keegan et al. | |

OTHER PUBLICATIONS

Witt et al, Blood, 2003, 101, Jul. 2001.*
Spyrou et al, Blood, Cells, Molecules and Diseases, 2010, 44, 100-106.*
Hoffman LaRoche Monograph, 2007, pp. 1-10.*
McGovern, T. J. HFD-570, 1998, pp. 123-131.*
Linscott's Directory, 1980, p. 1.*
Atweh et al., Blood 93(6):1790-1797 (1999). "Sustained Induction of Fetal Hemoglobin by pulse butyrate therapy in sickle cell disease."
Cao et al. Blood 103(2):701-709 (2004). "Induction of human gamma globin gene expression by histone deceatylase inhibitors."
Charache et al., Blood 69:109-116 (1987). "Hydroxyurea-induced augmentation of fetal hemoglobin production in patents with sickle cell anemia."
Goldberg et al. J. Biol. Chem. 252:3414-3421 (1977). "Particiaption of hemoglobin A and F in polymerization of sickle hemoglobin."
Letvin et al., N. Engl. J. Med. 310:869-873 (1984). "Augmentation of fetal-hemoglobin production in anemic monkeys by hydroxyurea."
Mork et al., Current Reviews in Pharmacology 11:1091-1104 (2005). "A mechanic approach to anticancer therapy: targeting the cell cycle with Histone Deacetylase inhibitors."
Nudel et al., Proc. Nat. Acad. Sci. USA 74:1100-1104 (1977). "Differential effects of chemical inducers on expression of B globin genes in murine erythroleukemia cells."
Partington et al., The EMBO Journal 3(12):2787-2792 (1984). "Human globin gene transcription in injected Xenopus oocytes: enhancement by sodium butyrate."
Perrine et al., N. Eng. J. Med. 328:81-86 (1993). "A short-term trial of butyrate to stimulate fetal-globin-gene expression in the B-globin disorders."
Perrine et al., Pediatr Ann. 37:339-346 (2008). "Fetal goblin stimulant therapies in the beta-hemoglobinopathies: principles and current potential."
Perrine et al., Ann NY Acad. Sci. 1202:158-164 (2010). "Fetal globin gene inducers: novel agents and new potential."
Perrine et al., Hematol Oncol Clin North Am. 28(2):233-248 (2014). "Targeted fetal hemoglobin induction for treatment of beta hemaglobinopathies."
Saito et al., Proc. Natl. Acad. Sci. USA 96:4592-4597 (1999). "a synthetic inhibitor of histone deacetylase MS-27-275 with marked in vivo antitumor activity against human tumors."
Sangerman et al., Amer. Soc. Hematology, 56th Annual Meeting and Exposition: San Francisco, CA; Thalassemia and Globin Gene Regulation, Poster 4277 (2010). "Identification of new and diverse inducers of fetal hemaglobin with high throughput screening (HTS)."
Skarpidi et al. Blood 96:321-326 (2000). Novel in vitro assay for the detection of pharmacologic inducers of fetal hemoglobin.
Steinberg et al., Medicine 80:328-44, (2001). "Pharmacologic modulation of fetal hemoglobin."
Steinberg et al. Br.J.Haematol. 129:465-81, 2005. "Predicting the clinical severity of sickle cell disease."
Steinberg, M.G.., The Scientific World 8: 1295-1324 (2008). "Sickle cell Anemia, the First Molecular Disease: overview of molecular etiology pathophysiology, and therapeutic approaches."
Suzuki et al., J. Med. Chem. 42:3001-3003 (1999). "Synthesis and histone deacetylase inhibitory activity of new benzamide derivatives"
Takahashi et al., Gann 66:577-80, (1977). "Differentiation of Cultured friend leukemia cells induced by short-chain fatty acids."
Weatherall, D.J., Blood 115:4331-4336 (2010). "The inherited diseases of hemoglobin are an emerging global health burden."
Wittich et al., Anticancer Drugs. 16(6):635-43 (2005). "Effect of inhibitors of histone deacetylase on the induction of cell differentiation in murine and human erythroleukemia cell lines."
International Search Report PCT/US2014/051887.

\* cited by examiner

*Primary Examiner* — Ganapathy Krishnan
(74) *Attorney, Agent, or Firm* — Nixon Peabody LLP

(57) ABSTRACT

The present invention generally relates to compositions containing chemical compounds and compositions and pharmaceutical formulations of the compounds which increase the expression of total hemoglobin or globin protein such as embryonic or fetal globin, or the proliferation of hemoglobin expressing and other blood cells. These compositions can be used to treat or prevent the symptoms associated with anemia, sickle cell diseases, thalassemia, and other blood cell deficiencies and blood disorders. The invention also relates to methods for administering these compositions to subjects and for use as medical aids for the treatment and prevention of blood and other disorders.

25 Claims, 12 Drawing Sheets

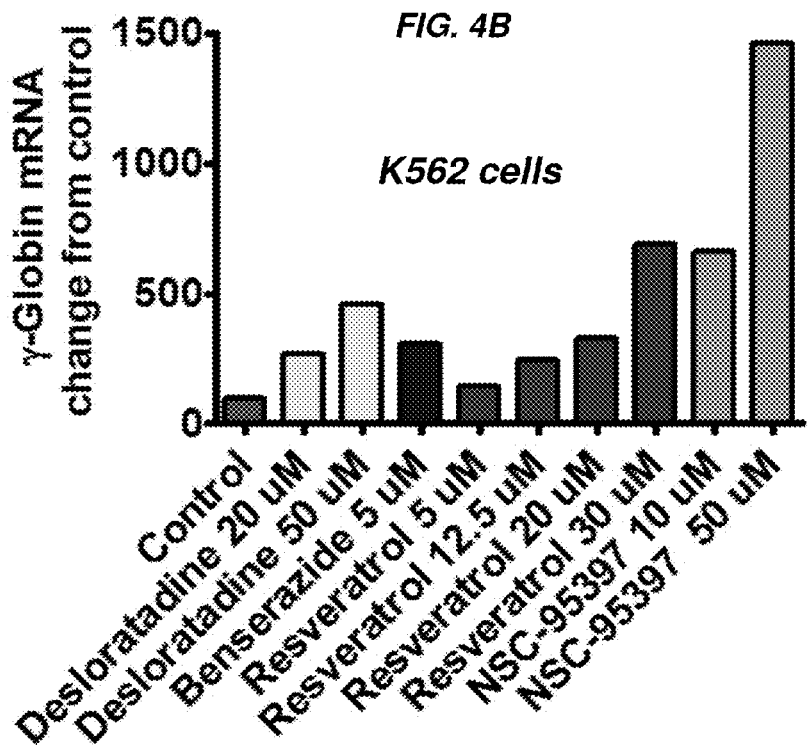
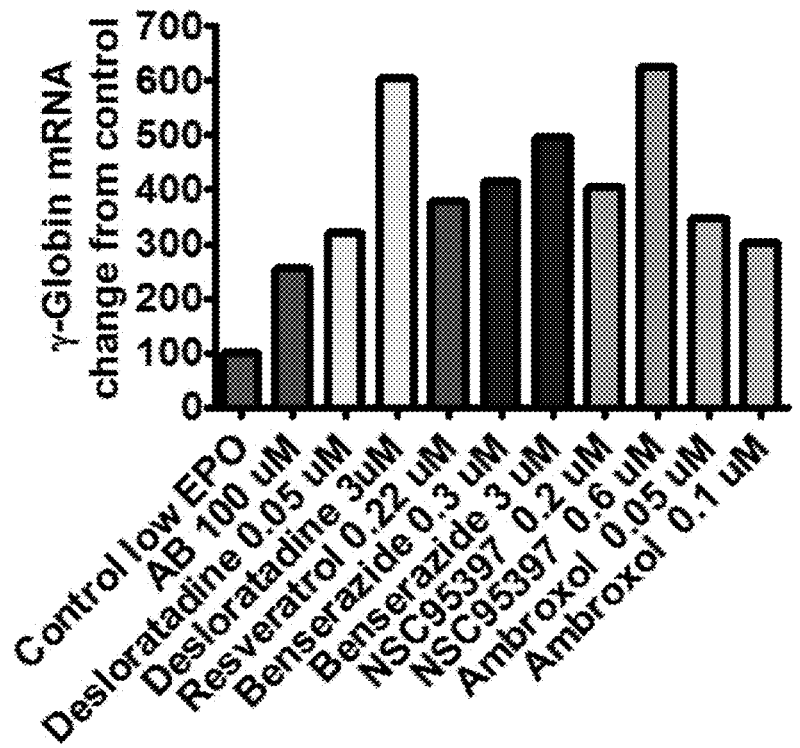

FIG. 7

| | | |
|---|---|---|
| Ambroxol | A mucolytic agent which has extensive clinical experience and a benign safety profile. | |
| Benserazide | Used in a combination to enhance the PK profile of L-dopa, and is reported to have no clinical effects itself. | |
| Desloratadine | This therapeutic is approved in children and adults as an allergy medication. Its safety profile is benign in extensive clinical use | |
| Resveratrol | This is a natural substance identified from red wine and has been studied clinically in cancer trials and for anti-oxidant actions | |
| NSC-95397 | This phosphatase inhibitor is not currently a clinical stage agent and may have cytotoxicity, but is a known bioactive. It will undergo *in vitro* evaluation, although it may not advance to *in vivo* studies | |
| Idarubicin | An anthracycline anti-leukemic drug that is currently combined with cytosine arabinoside as a first line treatment of acute myeloid leukemia. It belongs to the family of drugs called antitumor antibiotics. FDA approved. | |
| MS-275 | An oral pan-HDAC inhibitor, was initially developed by the NCI and has been studied in many oncology trials. The major adverse effect is fatigue, but it can be administered infrequently, eg, once every 2 weeks and is therefore worthwhile to evaluate. It does not have the cardiac side effects of many HDAC inhibitors. | |

*FIG. 11*

| Compound | FDA-Approved | Reporter | | γ-globin mRNA in K562 (fold increase) | γ-globin mRNA in BFUe (fold increase) |
| --- | --- | --- | --- | --- | --- |
| | | HTR (fold increase) | Dual-Luciferase (fold increase) | | |
| Arg. But. (control) | No | 4 (1000 μM) | 4.05 (1000 μM) | 2.2 (1500 μM) | 2.5 (100 μM) |
| Idarubicin | Yes | 7 (1 μM) | 13 (1 μM) | 8 (10 μM) | |
| Ambroxol | Yes | 1.8 (4 μM) | 1.4 (1 μM) | 1.1 (20 μM) | 3.4 (0.05 μM) |
| Desloratadine | Yes | 1.5 (1 μM) | 1.26 (20 μM) | 4.5 (50 μM) | 6 (3 μM) |
| Benserazide | No | 2.4 (5 μM) | 1.4 (5 μM) | 3 (5 μM) | 4.9 (3 μM) |
| NSC-95397 | No | 5.6 (1.07 μM) | 1.23 (1 μM) | 6 (10 μM) | 5 (0.2-0.6 μM) |
| MS-275 | No | 3.9 (5 μM) | 3.67 (5 μM) | 3 (20 μM) | 5.9 (0.5 μM) |
| Resveratrol | No | 3.2 (10 μM) | 3.23 (10 μM) | 4 (10-30 μM) | 3.7 (0.2 μM) |
| HQK1001 | No | 1.1 (3000 μM) | 1.1 (3000 μM) | 1.1 (4000 μM) | 2.2 (500 μM) |

γ-globin mRNA induced by HDAC inhibitors in erythroid progenitors

γ-globin mRNA induction in primary erythroid progenitors by test agents

INDUCERS OF HEMATOPOIESIS AND FETAL GLOBIN PRODUCTION FOR TREATMENT OF CYTOPENIAS AND HEMOGLOBIN DISORDERS

CROSS REFERENCE TO RELATED APPLICATIONS

This application claims priority under 35 U.S.C. 119(e) of U.S. Provisional Patent Application Ser. No. 61/419,016 filed on Dec. 2, 2010, the contents of which are incorporated herein by reference in their entirety.

FIELD OF THE INVENTION

The present invention is directed to methods and compositions for the treatment of hemoglobin disorders and blood disorders and increase total hemoglobin or globin protein such as embryonic or fetal globin (HbF), or induction of erythropoiesis and the proliferation of hemoglobin expressing cells in a subject. The compositions and methods can be used to treat and/or prevent the symptoms associated with anemia, sickle cell diseases, thalassemia and other blood cell deficiencies and blood disorders.

BACKGROUND OF THE INVENTION

Inherited disorders of production of the β-chain of adult hemoglobin A (β-thalassemia) or mutations affecting the structure of the β-globin chain (sickle cell disease) are the most common genetic diseases in the world, afflicting millions of individuals worldwide, and are designated by WHO as a global health burden. Pharmacological augmentation of fetal hemoglobin (γ-globin chain) production, to replace the defective or missing β-globin chains, has emerged as a promising therapeutic modality.

Anemia, a red blood cell disorder, can be grossly defined as a reduction in the ability of blood to transport oxygen. Although red blood cell disorders may be caused by certain drugs and immune system disorders, the majority are caused by genetic defects in the expression of hemoglobin. Disorders of hemoglobin synthesis include deficiencies of globin synthesis such as thalassemia syndromes and structural abnormalities of globin such as sickle cell syndromes and syndromes associated with unstable hemoglobins.

Fetal globin (also known as gamma globin or γ globin) normally combines with alpha globin chains prenatally to form fetal hemoglobin (HbF). Fetal globin is replaced by beta globin after birth, which then combines with alpha globin to form adult hemoglobin A. Fetal globin performs the same function as beta globin, and can combine with the alpha chains to generate a healthy form of hemoglobin thereby reducing high concentrations of unmatched alpha globin chains.

The various types of β thalassemias are syndromes resulting from mutations which produce a deficiency of β globin chains. In beta thalassemia, the unmatched alpha globin chains aggregate inside red blood cells (RBCs) and their progenitors, causing the premature destruction of RBCs and RBC progenitors, which results in anemia, transfusion-dependence, iron overload, organ failure, and early death.

In sickle cell disease (SCD), one amino acid substitution in the beta globin chain results in the generation of sickling hemoglobin (HbS), which allows polymerization with repeated cycles of deoxygenation. Polymerization results in "sickling" of RBCs. The sickled RBCs undergo hemolysis, while adhesive sickled RBCs occlude the microcirculation, provoking widespread tissue ischemia and organ infarction. The natural history of SCD is marked by painful crises and acute chest syndrome and eventual potentially life-threatening sequelae, including renal insufficiency, retinitis, osteonecrosis, osteomyelitis, aplastic crises, functional asplenism, stroke, priapism, and severe pulmonary hypertension.

Many efforts to stimulate HbF production have accordingly been undertaken, but pharmacologic reactivation of high-level HbF expression with non-toxic and tolerable therapeutic agents that are orally-available (for worldwide therapeutic application) has been an elusive therapeutic goal for many years. In sickle cell disease, average HbF levels in adult patients are 5-7%; but levels of HbF >15-20% and >70% F-cells are typically required to ameliorate most of the clinical complications. One HbF stimulant therapeutic, hydroxyurea (HU), is FDA-approved for treatment of sickle cell disease and benefits approximately 40% of subjects, with most benefit occurring those who attain absolute HbF levels >0.5 g/dl or 20%. HbF levels achieved are often not sufficiently high to completely ameliorate all complications. Additional therapeutics, especially non-cytotoxic agents which can be used in combinations with HU, could provide additional benefit. There are no therapeutic agents approved for the β-thalassemia syndromes.

Individuals with severe sickle cell anemia develop no symptoms until about five to six months after birth. In these infants it was determined that fetal hemoglobin did not interact with HbS and, as long as sufficient quantities were present, could modulate the effects of HbS disease. This modulating effect of β globin is also observed with other β globin disorders, such as HbC and HbD, and other mutations of the β chain. HbS polymerization is also significantly affected by the hemoglobin concentration of the cell. The higher the HbS concentration, the greater the chances for contact between two or more HbS molecules. Dehydration increases hemoglobin concentration and greatly facilitates sickling.

The thalassemia syndromes are a heterogeneous group of disorders all characterized by a lack of or a decreased synthesis of the globin chains of HbA. Deficiencies of β-globin expression are referred to as β-thalassemias and deficiencies of α-globin, α-thalassemias. The hemolytic consequences of deficient globin chain synthesis result from decreased synthesis of one chain and also an excess of the complementary chain. Free chains tend to aggregate into insoluble inclusions within erythrocytes causing premature destruction of maturing erythrocytes and their precursors, ineffective erythropoiesis, and the hemolysis of mature red blood cells. The underlying defects of hemoglobin synthesis have been elucidated over the years and largely reside in the nucleic acid sequences which express or control the expression of a or p globin protein.

Beta thalassemias are genetic disorders of moderate to severe anemias, caused by molecular mutations which decrease production of the beta globin chain of adult hemoglobin A ($\alpha_2\beta_2$). Unmatched alpha globin is toxic and causes early apoptosis of red blood cell precursors. In thalassemia major, patients have severe anemia and require red blood cell transfusions regularly to survive, beginning in infancy. In thalassemia intermedia, there is moderate, chronic hemolytic anemia, which adversely affects growth, cardiac function, and other systems; transfusions are used intermittently in childhood but often required regularly later in life. Complications of blood transfusions, iron overload and hepatitis C, cause widespread organ damage and early mortality. Beta hemoglobinopathies, or sickle cell syndromes, caused by a single point mutation (A-T) in the beta globin gene, causes polymerization of HbS, distortion of the red blood cell, chronic hemolysis, vascular adhesion, tissue hypoxia, and widespread organ damage. Fetal hemoglobin, (HbF, $\alpha_2\gamma_2$), is an alternative type of hemoglobin that is normally silenced in early childhood. Renewed or increased fetal globin (HbF) expression replaces the missing adult globin protein and reduces anemia in beta thalassemia, and inhibits sickling in sickle cell disease, preventing almost all the complications of this disease, when present in adequate amounts.

In the US and EU, beta thalassemias are niche orphan conditions, with an estimated 1200 patients in the US and 6500 patients in the EU, primarily in Italy, Greece, and the UK, with small populations in Germany and France. In the US, sickle cell disease is also an orphan condition with 80-100,000 patients. Ex-US, these conditions are considered a major global health burden, with 500,000 patients estimated in SE Asia.

A small number of therapeutic agents of different chemical classes can induce HbF experimentally, with only a few are orally-active or currently in clinical testing. Three general classes of therapeutic agents have been shown to induce HbF significantly in subjects with sickle cell disease and β-thalassemia, including: cytotoxic chemotherapeutic agents (such as Hydroxyurea (HU), 5-azacytidine, and decitabine), erythropoietin (EPO) preparations, and short chain fatty acids (SCFAs) and derivatives (SCFADs) which include some HDAC inhibitors. Additionally, there are a variety of small molecules have been shown to effect hemoglobin or fetal globin expression. Early experiments demonstrated that acetate ($CH_3COOH$), propionate ($CH_3CH_2COOH$), butyrate ($CH_3CH_2CH_2COOH$) and isobutyrate ($CH_3CH(CH_3)COOH$) all induced hemoglobin synthesis in cultured Friend leukemia cells (E. Takahashi et al., Gann 66:577-80, 1977). Additional studies showed that polar compounds, such as acid amides, and fatty acids could stimulate the expression of both fetal and adult globin genes in murine erythroleukemia cells (U. Nudel et al., Proc. Natl. Acad. Sci. USA 74:1100-4, 1977). Hydroxyurea ($H_2NCONHOH$), another relatively small molecule, was found to stimulate globin expression (N. L. Letvin et al., N. Engl. J. Med. 310:869-73, 1984). Stimulation, however, did not appear to be very specific to fetal globin (S. Charache et al., Blood 69:109-16, 1987). Hydroxyurea (HU) is also a well-known carcinogen making its widespread and long term use as a pharmaceutical impractical. One of the major breakthroughs in the treatment of hemoglobinopathies was made when it was discovered that butyric acid (butanoic acid; $CH_3CH_2CH_2COOH$) accurately and specifically stimulated transcription of the human fetal globin (HbF or γ-globin) gene (G. A. Partington et al., EMBO J. 3:2787-92, 1984). Some of these have shown proof-of-principle, but, except for HU, have required parenteral administration or large doses, which were not suitable for broad application.

While three short chain fatty acid (SCFA) agents have been reported to induce γ-globin expression and to increase hemoglobin levels in subjects with β-thalassemia, rendering some β-thalassemia subjects transfusion-independent, these prior generations of SCFAs, including arginine butyrate (AB) and sodium phenylbutyrate (SPB), have limited utility as a therapeutic agent in vivo, as they are either rapidly metabolized, required intravenous (IV) infusions, or required large doses which were difficult for subjects to tolerate long-term. Furthermore, these 1st generation SCFAs are also known to inhibit erythroid cell proliferation, and therefore require titration and intermittent dosing, complicating their use in conditions of anemia where compensatory erythroid cell proliferation is desirable. There, thus remains an unmet clinical need for a therapeutic agent that induces γ-globin gene expression and does not inhibit erythroid cell proliferation (i.e., is not cytotoxic), and which is more applicable for wide application in these genetic diseases.

Despite long-term efforts, regulatory approval has been obtained for only one chemotherapeutic agent. Pharmacologic reactivation of high-level HbF expression with noncytotoxic, tolerable therapeutics is still an unmet medical need for this global health burden. Arginine Butyrate and Phenylbutyrate have demonstrated proof-of-principle in re-inducing expression of HbF, correcting globin imbalance, increasing hemoglobin levels, and reducing transfusion requirements, these HDAC inhibitors, however, were inconvenient for broad application due to high dose requirements and/or IV administration. Accordingly, there is an unmet need for low dosing, long-term use of orally available and high activity agents which induce HbF expression which are safe for use in a large patient base.

SUMMARY OF THE INVENTION

The present invention relates to agents which function as fetal globin-inducing agents as well as to stimulate blood cell production, for the treatment of β-globin disorders, such as sickle cell anemia and thalassemias.

To investigate potential therapeutic libraries for unrecognized HbF inducers, the inventors developed a high-throughput screening (HTS) program to interrogate diverse chemical libraries, including a library of FDA-approved and clinical stage drugs. Using this assay, the inventors identified unexpected new and highly potent HbF-inducing drugs, some of which are already in clinical use for other medical indications and have established safety profiles.

Herein, using a promoter reporter gene assay that detects β globin gene promoter induction and cytotoxicity for high throughput screen, the inventors have identified structurally unrelated compounds with high potent activity for increasing γ-globin expression in vitro and in vivo. In particular, the inventors have discovered a variety of short chain fatty acid derivatives (SCFADs) which function as fetal globin-inducing agents. SCFADs offer particular appeal for safe, long-term treatment of these diseases as, unlike the chemotherapeutic agents, SCFADs are not mutagenic. The inventors demonstrate that the compounds as disclosed herein are non-cytotoxic. Cell viability in the presence of the compounds as disclosed herein can be assayed by DNA fragmentation assays or cell division assays, or by measuring the amount of nucleic acid or protein synthesis which occurred in treated cells as compared to untreated cells. Cells tested may be normal healthy cells, subject cells to be treated or cells in tissue culture.

The inventors demonstrate in an in vivo non-primate model that these compounds increase total hemoglobin and increase in γ-globin expression. Accordingly, the compounds as disclosed herein can be used in method for the treatment of β-globin disorders, such as, for example, Sickle Cell Disease and α- and β-Thalassemias. Accordingly, subjects in need of increased non-alpha-globin expression (e.g., γ- or β-globins) can be selected and administered the compounds identified herein for treatment of beta globin diseases, such as Sickle Cell Disease, α-thalassemias, and β-Thalassemias.

Some of the identified compounds have previously been demonstrated to have a high safety profile and are already FDA-approved. However, their use to increase γ-globin expression and for the treatment of β-globin disorders or administration to a subject in need of increased γ-globin expression or for the treatment of anemia or cytopenias was not known. In some embodiments, a subject who is treated with the compounds as disclosed herein is selected to have blood cell disorder, or a low red blood count, or is anaemic or has a cytopenia.

Accordingly, in some embodiments, aspects of the present invention relate to methods and compositions for increasing the amount of fetal hemoglobin in a subject with a blood disorder, including α- and β thalassemias and sickle cell disease. Without wishing to be bound by theory, fetal hemoglobin (HbF: α2, γ2) is an endogenous type of hemoglobin which is present in all humans, but is normally suppressed in infancy to levels below 2%. Decades of biochemical, clinical, and epidemiologic research have shown that any increase in HbF and F-cell levels reduce the severity of sickle cell disease, or alleviate the anemia of α- and β-thalassemia. It is well-established that fetal globin (γ-globin) chains interfere with the polymerization of sickle hemoglobin, preventing many pathologic consequences of sickling, and that adequate, or high levels of fetal hemoglobin (also referred to as hemoglobin F or HbF) correlate with mild or benign courses in sickle cell disease (SCD).

Accordingly, the inventors demonstrate herein pharmacologic augmentation of fetal hemoglobin (HbF, γ-globin) production, to replace diminished β-globin chains in the β-thalassemias and to inhibit HbS polymerization in sickle cell disease.

The invention overcomes many problems associated with current strategies for the treatment of β-globin diseases and pharmacological reactivation of high-level HbF expression, and provides new noncytotoxic compositions and methods for the treatment and prevention of blood disorders. In particular, the present invention generally relates to increasing the percentage of fetal hemoglobin (HbF or γ-globin) in the blood of a subject without decreasing proliferation of cells, the method comprising administering to the subject a composition comprising at least one of, or any combination of HbF-inducing drugs, which include, ambroxol, 2-amino-3-hydroxy-N'-(2,3,4-trihydroxybenzyl)propanehydrazide (Benserazide), 8-Chloro-6,11-dihydro-11-(4-piperidinylidene)-5H-benzo[5,6]cyclohepta[1,2-b]pyridine (Desloratadine), resveratrol, NSC-95397, idarubicin or N-(2-aminophenyl)-4-[N-(pyridin-3-yl-methoxycarbonyl)aminomethyl]benzamide (MS-275), or auronafin.

In some embodiments, the composition comprises at least one or a combination of any of 2-amino-3-hydroxy-N'-(2,3,4-trihydroxybenzyl)propanehydrazide (Benserazide) or 8-Chloro-6,11-dihydro-11-(4-piperidinylidene)-5H-benzo[5,6]cyclohepta[1,2-b]pyridine (Desloratadine) or N-(2-aminophenyl)-4-[N-(pyridin-3-yl-methoxycarbonyl)aminomethyl]benzamide (MS-275), or any pharmaceutically acceptable salt, polymorph or ester thereof.

One embodiment of the invention is directed to compositions that comprise one or more compounds which stimulate the proliferation of hemoglobin producing cells, the expression of hemoglobin or the expression of embryonic or fetal globin in mammalian cells. Chemical compounds, or HbF-inducing agents include, ambroxol, benserazide, desloratadine, resveratrol, NSC-95397, idarubicin, MS-275, or auronafin.

In some embodiments the compounds of the present invention, e.g., at least one of, or any combination of HbF-inducing drugs, which include, ambroxol, 2-amino-3-hydroxy-N'-(2,3,4-trihydroxybenzyl)propanehydrazide (Benserazide), 8-Chloro-6,11-dihydro-11-(4-piperidinylidene)-5H-benzo[5,6]cyclohepta[1,2-b]pyridine (Desloratadine), resveratrol, NSC-95397, idarubicin or N-(2-aminophenyl)-4-[N-(pyridin-3-yl-methoxycarbonyl)aminomethyl]benzamide (MS-275), or auronafin can be used in methods for the treatment of hemoglobin disorders, and to raise blood cell counts in vitro and in vivo, and as the compounds surprisingly increase red blood cell numbers and demonstrate red blood cell stimulation activity in addition to inducing HbF expression. Accordingly, the methods and compositions as disclosed herein can be used in the treatment of cytopenias and other anemias and/or hemoglobin disorders.

Another embodiment of the invention is directed to compositions comprising at least one or any combination of HbF-inducing agents selected from the group of ambroxol, benserazide, desloratadine, resveratrol, NSC-95397, idarubicin, MS-275, or auronafin, in particular benserazide, desloratadine or MS-275 that stimulate the proliferation of hemoglobin producing and other types of cells, the expression of hemoglobin or the expression of embryonic or fetal globin in mammalian cells, but do not decrease or otherwise adversely affect cell viability. Such HbF-inducing agents include benserazide, desloratadine or MS-275.

Another embodiment of the invention is directed to methods for the treatment of blood disorders, e.g., for the treatment of cytopenias and other anemias and/or hemoglobin disorders. Compositions containing an effective amount of one or more agents selected from, at least one or any combination of HbF-inducing agents selected from the group including, ambroxol, benserazide, desloratadine, resveratrol, NSC-95397, idarubicin, MS-275, or auronafin, in particular benserazide, desloratadine or MS-275 which stimulate the proliferation of hemoglobin producing cells or the expression of embryonic or fetal globin from cells are administered to patients. Patients may be any mammal such as a human. Administration may be by parenteral or nonparenteral means, but is preferably oral or intravenous. Treatment may be for short periods of time, e.g., pulsed or administered intermittently or continuous throughout the lifetime of the patient.

Another embodiment of the invention is directed to methods for the treatment of blood disorders, e.g., cytopenias, and/or hemoglobin disorders, comprising the administration of compositions containing therapeutically effective amounts of a HbF-inducing agent selected from at least one or any combination of ambroxol, benserazide, desloratadine, resveratrol, NSC-95397, idarubicin, MS-275, or auronafin, in particular benserazide, desloratadine or MS-275 which increases the proportion or number of reticulocytes that express embryonic or fetal globin and the amount of embryonic or fetal globin expressed per cell.

Accordingly, one aspect of the present invention relates to a method for increasing the percentage or absolute amount of fetal hemoglobin in the blood of a subject, comprising administering to the subject a pharmaceutical composition comprising at least one fetal hemoglobin inducing agent, wherein the fetal hemoglobin inducing agent is selected from 2-amino-3-hydroxy-N'-(2,3,4-trihydroxybenzyl)propanehydrazide, 8-Chloro-6,11-dihydro-11-(4-piperdinylidene)-5H-benzo[5,6]cyclohepta[1,2-b]pyridine, or N-(2-aminophenyl)-4-[N-(pyridin-3-yl-methoxycarbonyl)aminomethyl]benzamide, or a pharmaceutically acceptable salt or ester thereof, or a derivative thereof, or any combination of 2-amino-3-hydroxy-N'-(2,3,4-trihydroxybenzyl)propanehydrazide, 8-Chloro-6,11-dihydro-11-(4-piperdinylidene)-5H-benzo[5,6]cyclohepta[1,2-b]pyridine, and N-(2-aminophenyl)-4-[N-(pyridin-3-yl-methoxycarbonyl)aminomethyl]benzamide, wherein after administration, the percentage of fetal hemoglobin in the blood of the subject increases.

Another aspect of the present invention relates to a method of treating a blood disorder in a subject, comprising: administering to the subject determined to have a blood disorder, a pharmaceutical composition comprising at least one fetal hemoglobin inducing agent selected from benserazide, desloratadine, or MS-275, or a pharmaceutically acceptable salt or ester thereof, or a derivative thereof, or any combination of 2-amino-3-hydroxy-N'-(2,3,4-trihydroxybenzyl)propanehydrazide, 8-Chloro-6,11-dihydro-11-(4-piperdinylidene)-5H-benzo[5,6]cyclohepta[1,2-b]pyridine, and N-(2-aminophenyl)-4-[N-(pyridin-3-yl-methoxycarbonyl)aminomethyl] benzamide, to increase the percentage or absolute amount of fetal hemoglobin in the blood or increase the absolute number of red blood cells and/or hemoglobin to treat the blood disorder in the subject, and not administering a pharmaceutical composition comprising at least one fetal hemoglobin inducing agent selected from 2-amino-3-hydroxy-N'-(2,3,4-trihydroxybenzyl)propanehydrazide, 8-Chloro-6,11-dihydro-11-(4-piperidinylidene)-5H-benzo[5,6]cyclohepta[1,2-b]pyridine, or N-(2-aminophenyl)-4-[N-(pyridin-3-yl-methoxycarbonyl)aminomethyl]benzamide, or a pharmaceutically acceptable salt or ester thereof, or a derivative thereof to a subject who does not have a blood disorder.

In all aspects of the embodiments as disclosed herein, the method of treating a blood disorder or increasing the percentage or absolute amount of fetal hemoglobin in the blood of a subject in a subject further comprising administering to the subject 2,2-dimethylbutyrate, and/or can further comprise administering to the subject hydroxyurea (HU), or a HDAC inhibitor or a combination thereof. In some embodiments, a subject has been diagnosed or is selected to be treated based on having a blood disorder or anemia. In some embodiments, the blood disorder is sickle cell syndrome, α-Thalassemia, or a β-Thalassemia syndrome. In some embodiments, the blood disorder is caused by radiation therapy or chemotherapy.

In all aspects of the embodiments as disclosed herein an increase the percentage and/or absolute number of reticulocytes increases in the blood of the subject, and includes, but without limitation, an increase in the amount of hemoglobin and/or the percentage of hematocrit and/or amount of red blood cells in the blood of the subject. In some embodiments, red blood cell production increases.

In all aspects of the embodiments as disclosed herein, the agents and compositions as disclosed herein are administered by pulse administration. In some embodiments, they are administered orally to the subject. In some embodiments, the subject is a mammal, e.g., a human. In some embodiments, the subject is a child or infant or an infant under the age of 2.

In all aspects of the embodiments as disclosed herein, desloratidine is administered to a subject at a dose of at least 5 nM or at least 0.2 mg/kg, and benserazide is administered in a dose of at least 0.3 µM or at least 1 mg/kg, and MS-275 is administered in a dose of at least between 0.1 mg/kg and 10 mg/kg, or between 1 mg/m² and 4 mg/m².

Another embodiment of the invention is directed to methods for regulating the expression of a globin gene such as an embryonic or fetal globin gene or an at least partially functional pseudo-globin gene in mammalian cells. In some embodiments, treated cells, e.g., ex vivo, or products expressed from these cells, can be harvested and introduced or reintroduced to a subject to treat or prevent a blood disorder.

Another embodiment of the invention is directed to methods for inducing or increasing the proliferation of hemoglobin expressing cells. Cells in culture or in patients are exposed to compositions of HbF-inducing agents selected from the group including, at least one or any combination of ambroxol, benserazide, desloratadine, resveratrol, NSC-95397, idarubicin, MS-275, or auronafin, in particular benserazide, desloratadine or MS-275 and induced to proliferate. Proliferating cells may be stem cells, committed cells such as BFUs or CFUs, or mature reticulocytes. These cells can be used to treat blood disorders or to produce large quantities of products which are expressed from bacterial or mammalian cells.

Another embodiment of the invention is directed to methods for the prevention of blood disorders. Compositions containing an effective amount of agents as disclosed herein, e.g., at least one or any combination of ambroxol, benserazide, desloratadine, resveratrol, NSC-95397, idarubicin, MS-275, or auronafin, in particular benserazide, desloratadine or MS-275 which stimulate the proliferation of hemoglobin producing cells or the expression of embryonic or fetal globin are administered to patients suspected of having a blood disorder. The subject may be any mammal such as a human and is preferably an adolescent, child or infant. Administration may be by any route including parenteral and nonparenteral routes, but is preferably oral, subcutaneous or intravenous. Treatment may be for short periods of time or continuous throughout the lifetime of the patient.

BRIEF DESCRIPTION OF THE DRAWINGS

FIG. 2 shows that some new candidates have significantly higher activity and potency in increasing γ globin expression.

FIGS. 4A-4C shows the % induction of the γ-globin mRNA gene expression by different HTS compounds in different cells. FIGS. 4A and 4B shows % induction of γ-globin mRNA gene expression in K562 cells, showing Resveratrol (30 µM), desloratadine (50 µM), NSC (50 µM) and Benserazine (5 µM) had the most significant % increase in γ-globin mRNA expression. FIG. 4C shows % induction of γ-globin mRNA gene expression in HFU-E (burst-forming units-erythroid) cells, showing Resveratrol (30 µM), desloratadine (50 µM), NSC (50 µM) and Benserazine (5 µM) had the most significant % increase in γ-globin mRNA expression.

FIG. 5A shows the absolute γ-globin mRNA increase of Desloratadine at 10 μM-100 μM, showing Desloratadine results in the most γ-globin mRNA expression at 50 μM. FIG. 5B shows the absolute γ-globin mRNA increase with Resveratrol at 5 μM-30 μM, showing Resveratrol results in the most γ-globin mRNA expression at 30 μM. FIG. 5C shows the absolute γ-globin mRNA increase with NSC at 1 μM-50 μM, showing NSC results in the most γ-globin mRNA expression at 50 μM.

FIG. 7 shows a table with HbF-inducing agents identified from an FDA-approved library using the HTS as disclosed herein. Several compounds were eliminated from further development as potential hemoglobinopathy therapeutics because of cytotoxicity (e.g. Idarubicin), but were nonetheless validated in confirmatory assays as potent HbF-inducers.

FIG. 10A shows western blood showing MS275 (10 μM) does not have Bcl11A expression. FIG. 10B shows analysis of mRNA of γ-globin expression in K562 cells.

FIG. 11 is a table of the fold increase fetal globin mRNA in erythroid progenitors. HbF-inducers idarubicin, ambroxol, NSC-95397 and resveratrol had between a 3.5 to 6-fold increase, which was higher than prior agents such as arginine butyrate (AB) and SDMN (referred to as HQK-1001 in this table).

FIG. 12A shows γ-globin mRNA expression in the blood of baboons administered fetal hemoglobin inducing agents, MS-275 and desloratadine (DSL). Administration of 3 mg/m² MS-275 (for 4 days and 2 weeks) increases the γ-globin mRNA expression in the blood to the same level as compared to administration of the positive control ST20 (sodium 2,2-dimethylbutyrate) (150 mg/kg), and administration of 0.6 mg/kg of desloratadine (DSL) for two days was more effective at increasing γ-globin mRNA expression than administration of the positive control ST20 after 2 or 4 days. FIG. 12B shows total hemoglobin (Hb) levels in the blood of baboons administered fetal hemoglobin inducing agents, MS-275 and desloratadine (DSL). Administration of 3 mg/m² MS-275 (for 4 days and 2 weeks) increases blood total hemoglobin (Hb) levels to a greater extent as compared to administration the positive control ST20 (sodium 2,2-dimethylbutyrate) (150 mg/kg for 2 and 4 days), and administration of 0.6 mg/kg of desloratadine (DSL) for two days was significantly more effective at increasing blood total hemoglobin (Hb) levels than the administration of the positive control ST20 after 2.

DETAILED DESCRIPTION OF THE INVENTION

Figure 1A:
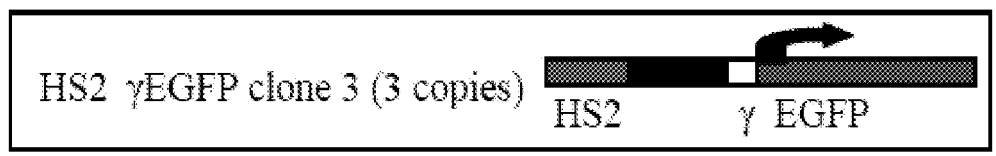
FIG. 1A shows the γ-globin reporter structure used in the high throughput screen (HTS) which is a cell-based assay comprising a locus control region (LCR-HS2) linked to the y-globin gene promoter and enhanced GFP (EGFP).
Figure 1B:
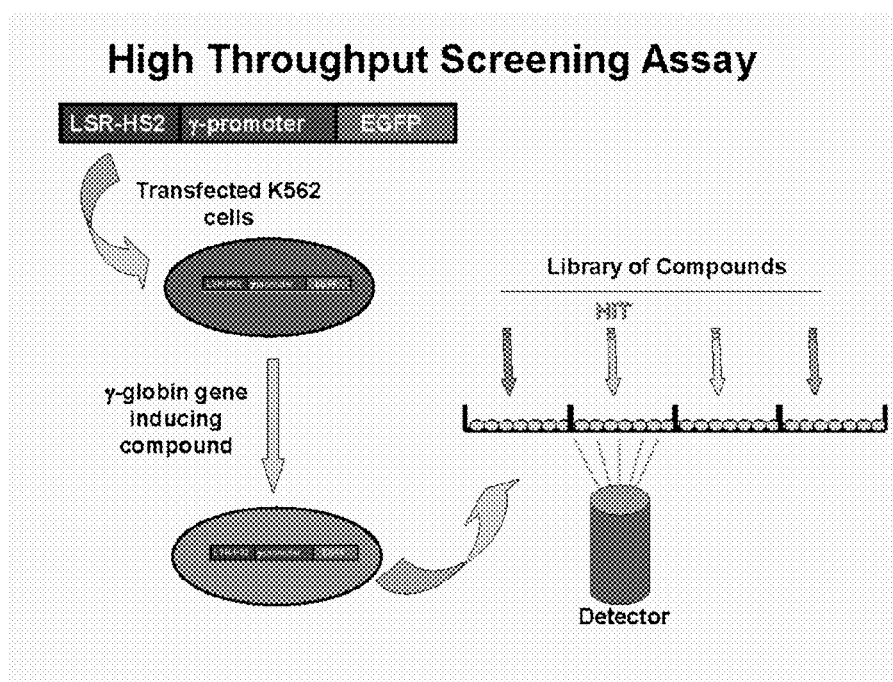
FIG. 1B is a schematic illustration showing an illustration of the method of the high throughput screening assay (HTS) with the cell construct comprising a locus control region (LCR) linked to the y-globin gene promoter and enhanced GFP (EGFP). A compound which activates γ-globin promoter will induce gene expression of EGFP which can be detected by a suitable detector.

The present invention relates to compounds which increase γ-globin expression in a subject in vivo, for example, for use in compositions and methods for the treatment of γ-globin disorders such as, but not limited to Sickle Cell anemia and β-Thalamassia.

In particular, the present invention generally relates to increasing the percentage of fetal hemoglobin (HbF or γ-globin) in the blood of a subject, the method comprising administering to the subject a composition comprising at least one of, or any combination of ambroxol, benserazide, desloratadine, resveratrol, NSC-95397, idarubicin, MS-275, or auronafin.

In some embodiments, the composition comprises benserazide or desloratadine or MS-275, or any pharmaceutically acceptable salt, polymorph or ester thereof.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "hematopoietic cell" as used herein is a collective term for all bone marrow-derived cell types in the blood (see also: hematopoiesis). Thus, a hematapoeitic cell refers to mature cell types and their immature precursors that are identifiable either by morphology or, mostly, by a distinct pattern of cell surface markers. The term is used to distinguish these cells from other cell types found in the body and also includes T-cells and distinctive subsets, which are the only hematopoietic cells that are not generated in the bone marrow. The specific precursors of mature blood cells that are defined by their ability to reconstitute completely bone marrow functions after its destruction are hematopoietic stem cells. Hematopoietic cells are subgrouped broadly into myeloid cells (erythrocytes, thrombocytes, neutrophils, monocytes and macrophages, eosinophils, basophils, mast cells) and the lymphoid cells (B-cells, various types of T-cells, NK-cells). Those cells that do not produce hemoglobin are leukocytes. Those cells that produce hemoglobin (red blood cells) are erythrocytes. A collective term for cells engaged in immune responses is lymphocytes.

The term "myelopiesis" as used herein refers to the formation of myeloid cells, including eosinophilic granulocytes, basophilic granulocytes, neutrophilic granulocytes, and monocytes. In hematology, myelopoiesis is the production of blood cells in the bone marrow. Without wishing to be bound by theory, a myeloid progenitor can differentiate in the bone marrow into granulocytes, macrophages (mature monocytes), mast cells (whose blood-borne progenitor is not well defined), and dendritic cells of the innate immune system. The granulocytes, also called polymorphonuclear leukocytes because of their oddly shaped nuclei, give rise to three short lived cell types including eosinophils, basophils, and neutrophils. A granulocyte differentiates into a distinct cell type by a process called granulopoiesis. In this process it first transforms from a common myeloblast (myeloid progenitor) to a common promyelocyte. This promyelocyte gives rise to a unique myelocyte that for the first time can be classified as an eosinophil, basophil, or neutrophil progenitor based on the histological staining affinity (eosinophilic, basophilic, or neutral granules). The unique myelocyte next differentiates into a metamyelocyte and then a band cell, with a "C" shaped nucleus, before becoming a mature eosinophil, basophil, or neutrophil. Macrophages come from monoblast progenitors that differentiate into promonocytes, which mature into monocytes. Monocytes eventually enter the tissues and become macrophages. The term myelopiesis includes the process of Granulopoiesis (Myeloblast, Promyelocyte, Myelocyte, Metamyelocyte, Band cell production); Monocytopoiesis (production of Monoblast, Promonocyte); MEP Thrombopoiesis (production of Megakaryoblast, Promegakaryocyte); Erythropoiesis (production of Proerythroblast, Normoblast, Reticulocytes).

The term "haematopoiesis" (also referred to herein ashaemopoiesis or hemopoiesis) refers to the formation of blood cellular components, and includes both the process of myleposieis and general extramedullary hematopoiesis. Without wishing to be bound by theory, all cellular blood components are derived from hematopoietic stem cells. In a healthy adult person, approximately $10^{11}$-$10^{12}$ new blood cells are produced daily in order to maintain steady state levels in the peripheral circulation.

The term "erythropoiesis" as used herein refers the process by which red blood cells (erythrocytes) are produced. Without wishing to be bound by theory, Erythropoiesis is stimulated by decreased $O_2$ delivery to the kidneys, which then secrete the hormone erythropoietin, which activates increased erythropoiesis in the hemopoietic tissues. In mammals (including humans), erythropoiesis usually occurs within the red bone marrow. In the early fetus, erythropoiesis takes place in the mesodermal cells of the yolk sac. By the third or fourth month, erythropoiesis moves to the spleen and liver. After seven months, erythropoiesis occurs in the bone marrow. However, in humans with certain diseases and in some animals, erythropoiesis also occurs outside the bone marrow, within the spleen or liver, which is referred to as extramedullary erythropoiesis.

The term "hematopoietic stem cell" or "HSC" as used herein refers to a multipotent stem cells that give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells). The term "hematopoietic stem cells" can also refer to stem cells or progenitor cells found in bone marrow and peripheral blood that are greater than about 10 μm in diameter and are capable of differentiating into any of the specific types of hematopoietic or blood cells, such as erythrocytes, lymphocytes, macrophages and megakaryocytes. HSCs are reactive with certain monoclonal antibodies which are now recognized as being specific for hematopoietic cells, for example, CD34+/CD45+. The term "hematopoietic stem cells" also refers to as "HSCs" refers to all types of hematopoietic cells throughout their differentiation from self-renewing hematopoietic stem cells through immature precursor cells of the various blood lineages to and including the mature functioning blood cells as would be understood by persons skilled in the art. Hematopoietic stem cells (HSCs) are multipotent stem cells that give rise to all the blood cells including myeloid and lymphoid lineages. These HSCs are responsible for constant maintenance and immune protection of every cell type of the body. Basically there are two types of HSC's, short term and long term stem cells. A short term HSC has limited hematopoietic capabilities whereas a true HSC's are the one which can self-renew itself for the entire life span. But it is very difficult to distinguish between short term and long term HSCs. As HSC's look and behave in culture like ordinary white blood cells, it's also difficult to identify them by morphology (size and shape). The only way to identify them is through cell surface proteins. Human HSC that express high levels of CD34 and low or absent levels of CD33, CD38, thy-1, and CD71, appear to be enriched for primitive progenitor and HSC activity, while more mature progenitors express one or more of these markers. Stem cells can also be identified based on side population depending on the surface markers used for staining HSC are useful for hematopoietic stem cell transplantation, which involves administration, e.g., intravenous infusion of autologous or allogenic stem cells collected from bone marrow, peripheral blood or umbilical cord blood to reestablish hematopoietic function in patients with damaged or defective bone marrow or immune system.

The term "proliferation" or "proliferating" as used herein refers to an increase in a number of cells in a population of cells by means of cell division or cell renewal. Cell proliferation, e.g., neutrophil proliferation or red blood proliferation as disclosed herein is generally understood to result from the coordinated activation of multiple signal transduction pathways in response to the environment, and can result in a direct replication of neutrophils or red blood cell counts or to increase in hematopoietic cell which produce neutrophil cells or red blood cells.

The term "treating", as used herein, refers to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

The term "pharmaceutically acceptable excipient", as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

Thus, as used herein, the term "pharmaceutically acceptable salt," is a salt formed from an acid and a basic group of a compound of the invention. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate salts.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. Other pharmaceutically acceptable salts are described in the Handbook of Pharmaceutical Salts. Properties, Selection, and Use (P. Heinrich Stahl and C. Wermuth, Eds., Verlag Helvetica Chica Acta, Zurich, Switzerland (2002)).

The term "subject" as used herein refers to a vertebrate, preferably a mammal, more preferably a primate, still more preferably a human. Mammals include, without limitation, humans, primates, wild animals, feral animals, farm animals, sports animals, and pets.

As used herein, a "prodrug" refers to compounds that can be converted via some chemical or physiological process (e.g., enzymatic processes and metabolic hydrolysis) to a biologically active agent. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design*, Theory and Application, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* ll,:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenyloin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv.*

*Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

The term "subject" is used interchangeably herein with "patient" and refers to a vertebrate, preferably a mammal, more preferably a primate, still more preferably a human. Mammals include, without limitation, humans, primates, wild animals, rodents, feral animals, farm animals, sports animals, and pets. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. A subject can be male or female.

Mammals other than humans can be advantageously used as subjects that represent animal models of conditions or disorders associated blood disorders. In addition, the methods and compositions described herein can be used to treat domesticated animals and/or pets.

A subject can be one who has been previously diagnosed with or identified as suffering from or having a blood disorder. A subject can one who is currently being treated for a blood disorder.

In some embodiments of the aspects described herein, the method further comprising diagnosing a subject for a blood disorder before onset of treatment with a method described herein. Methods of diagnosing blood disorders are well known in the art.

In some embodiments, the method further comprising selecting a subject diagnosed with a blood disorder before onset of treatment with a method described herein.

The term "therapeutically effective amount" as used herein refers to an amount sufficient to effect a beneficial or desired clinical result upon treatment. Specifically, the term "therapeutically effective amount" means an amount of a compound of this invention sufficient to measurably (i) reduce or inhibit the growth of transformed (cancer) cells in a relevant in vitro assay or cause a measurable improvement in an animal model of cancer and/or (ii) induce expression of fetal hemoglobin in a relevant in vitro assay or cause a measurable improvement in an animal model of a hemoglobinopathy and/or thalassemia, for example, a sickle cell disease. Alternatively, a "therapeutically effective amount" is an amount of a compound of this invention sufficient to confer a therapeutic or prophylactic effect on the treated subject against (i) cancer and/or (ii) a hemoglobinopathy and/or thalassemia. Therapeutically effective amounts will vary, as recognized by those skilled in the art, depending on the specific disease treated, the route of administration, the excipient selected, and the possibility of combination therapy.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. Furthermore, therapeutically effective amounts will vary, as recognized by those skilled in the art, depending on the specific disease treated, the route of administration, the excipient selected, and the possibility of combination therapy.

Physiological effects that can be measured to determine the therapeutically effective amount include, without limitation, substrate protein hyperacetylation (histone, tubulin, hsp90, p53, STAT, etc.), gene induction (fetal hemoglobin mRNA expression or protein expression), impaired protein trafficking, improved neuronal vesicle trafficking, induction of apoptosis, cell cycle arrest, and induction of p21.

Relevant assays to measure such effects include, without limitation, Western (immuno)blot, RT-PCR, expression profile by microarray or other technology, high-content immunofluorescence, cytoblot, biochemical inhibition of HDAC proteins, alterations in chromatin structure by ChIP, and alterations in histone and/or other target protein modification by mass spectrometry.

As used herein, a "promoter" or "promoter region" or "promoter element" used interchangeably herein refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "operatively linked" or "operatively associated" are used interchangeably herein, and refer to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined The term "obtaining" as in "obtaining the compound" is intended to include purchasing, synthesizing or otherwise acquiring the compound (or indicated substance or material).

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased","increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "substantially" as used herein means a proportion of at least about 60%, or preferably at least about 70% or at least about 80%, or at least about 90%, at least about 95%, at least about 97% or at least about 99% or more, or any integer between 70% and 100%.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Accordingly, the articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about."

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" is intended to encompass numbers that fall within a range of ±10% of a number, in some embodiments within ±5% of a number, in some embodiments within ±1%, in some embodiments within ±0.5% of a number, in some embodiments within ±0.1% of a number unless otherwise stated or otherwise evident from the context (except where such number would impermissibly exceed 100% of a possible value).

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

HbF-Inducing Agent

In particular, the present invention generally relates to increasing the percentage of fetal hemoglobin (HbF or γ-globin) in the blood of a subject, the method comprising administering to the subject a composition comprising at least one of, or any combination of HbF-inducing agents, selected from the group comprising; ambroxol, benserazide, desloratadine, resveratrol, NSC-95397, idarubicin, MS-275, or auronafin.

In some embodiments, a HbF-inducing agent is benserazide or desloratadine or MS-275, or any pharmaceutically acceptable salt, polymorph or ester thereof.

In certain embodiments, the amount of fetal globin in the blood of the subject increases with administration of a HbF-inducing agent as disclosed herein to the subject. In some embodiments, the number of F-cells in the blood of the subject increases with administration of one or more Hb-inducing agent as disclosed herein. In certain embodiments, the number of F-reticulocytes in the blood of the subject increases on administration of a HbF-inducing agent as disclosed herein. In some embodiments, the amount of total fetal hemoglobin in the blood of the subject increases. In certain embodiments, the amount of total hemoglobin in the blood of the subject increases. In some embodiments, the percentage of reticulocytes in the blood of the subject increases. In certain embodiments, the number of reticulocytes in the blood of the subject increases. In some embodiments, hematocrit increases. In certain embodiments, red blood cell production increases.

In some embodiments, a composition comprising at least one HbF-inducing agent as disclosed herein is administered in an effective amount to increase the expression of γ-goblin in the blood by a statistically significant increase as compared to in the absence of a compound. In some embodiments, a composition comprising at least one HbF-inducing agent as disclosed herein is administered to increase the expression of γ-goblin in the blood by a statistically significant increase as compared to in the presence of a control agent, such as, for example, ST20.

In some embodiments, a composition comprising at least one HbF-inducing agent as disclosed herein, for example, any one, or any combination of ambroxol, benserazide, desloratadine, resveratrol, NSC-95397, idarubicin, MS-275, or auronafin, or in particular, benserazide, desloratadine, or MS-275 is administered in an effective amount to increase the level of γ-globin expression in blood by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to either in the absence of the composition, or as compared to a positive control agent, such ST20.

In some embodiments, a composition comprising at least one HbF-inducing agent as disclosed herein, for example, any one, or any combination of ambroxol, benserazide, desloratadine, resveratrol, NSC-95397, idarubicin, MS-275, or auronafin, or in particular, benserazide, desloratadine, or MS-275 is administered in an effective amount to increase the total amount of fetal globin in the blood, e.g., the blood in a subject by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to either in the absence of the composition, or as compared to a positive control agent, such ST20.

In some embodiments, a composition comprising at least one HbF-inducing agent as disclosed herein, for example, any one, or any combination of ambroxol, benserazide, desloratadine, resveratrol, NSC-95397, idarubicin, MS-275, or auronafin, or in particular, benserazide, desloratadine, or MS-275 is administered in an effective amount to increase the total hemoglobin in the blood, e.g., the blood in a subject by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to either in the absence of the composition, or as compared to a positive control agent, such ST20.

In some embodiments, administration of one or more HbF-inducing agent is a pulsed administration. In certain embodiments, a pulsed administration comprises administering one or more HbF-inducing agent for about 8 weeks, followed by not administering a HbF-inducing agent for about 4 weeks. In some embodiments, the pulsed administration comprises administering at least one HbF-inducing agent for about 6 weeks, followed by not administering a HbF-inducing agent for about 2 weeks. In certain embodiments, the pulsed administration comprises administering at least one HbF-inducing agent for about 4 weeks, followed by not administering a HbF-inducing agent for about 2 weeks. In some embodiments, the pulsed administration comprises administering at least one HbF-inducing agent for about 2 weeks, followed by not administering a HbF-inducing agent for about 2 weeks. In some embodiments, pulsed administration comprises pulses of administering at least one HbF-inducing agent for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, pulsed administration comprises intervals of not administering a HbF-inducing agent of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, administration is continuous. In certain embodiments, administration is for the lifetime of the subject.

In some embodiments, a subject is a mammal. In certain embodiments, a mammal is an animal. In some embodiments, an animal is a horse. In certain embodiments, the mammal is a human. In some embodiments, the human is a child. In certain embodiments, a human is under the age of 18. In some embodiments, a human is under the age of 10. In some embodiments, a human is under the age of 2.

Further provided herein are methods for increasing the percentage of fetal hemoglobin in the blood of a subject diagnosed with a α- and/or β thalassemia comprising administering to the subject a composition comprising at least one HbF-inducing agent or a pharmaceutically acceptable salt, or ester thereof, wherein after the administration the percentage of fetal hemoglobin in the blood of the subject increases by a statistically significant amount as compared to the absence of administration of the HbF-inducing agent, or a control agent, such as, for example, ST20.

In some embodiments, provided herein are methods for increasing the percentage of fetal hemoglobin in the blood of a subject diagnosed with a α- and/or β thalassemia comprising administering to the subject a composition comprising one or more HbF-inducing agents, as the free acid, a pharmaceutically acceptable salt, or ester thereof.

In some embodiments, the percentage of fetal hemoglobin in the blood of a subject increases after one week of administering as compared to baseline. In other embodiments the percentage of fetal hemoglobin in the blood of a subject increases after two weeks of administering as compared to baseline. In certain embodiments, the percentage of fetal hemoglobin in the blood of a subject increases after four weeks of administering as compared to baseline. In some embodiments, the percentage of fetal hemoglobin in the blood of a subject increases after one day of administering as compared to baseline. In certain embodiments the percentage of fetal hemoglobin in the blood of a subject increases after 3 days of administering as compared to baseline.

In some embodiments, the methods for increasing the percentage of fetal hemoglobin further comprises administering to the subject at least one other therapeutic agent with at least one HbF-inducing agent, wherein the therapeutic agent can be selected from the group consisting of hydroxyurea, decitabine, an HDAC inhibitor, sodium 2,2 dimethylbutyrate, ST20 or a component of madopare or any combination thereof.

Benserazide

Benserazide (also called SERAZIDE™ or Ro 4-4602) is a peripherally-acting aromatic L-amino acid decarboxylase (AAAD) or DOPA decarboxylase inhibitor, which is unable to cross the blood-brain barrier, and has the following structure:

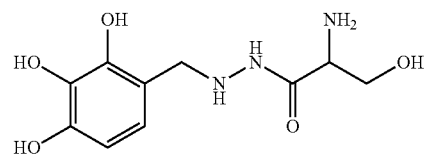 [SMILES: NC(CO)C(=O)NNCc1ccc(O)c(O)c1O]

Benserazide is commercially available and well known by persons of ordinary skill in the art has a systematic (IUPAC) name 2-amino-3-hydroxy-N'-(2,3,4-trihydroxybenzyl)propanehydrazide or is also known as (2S)-2-amino-3-(3,4-dihydroxyphenyl)propanoic acid or DL-serine-2-(2,3,4-trihydroxybenzyl)hydrazide-hydrochloride (benserazide) or 2-amino-3-hydroxy-N'-[(2,3,4-trihydroxyphenyl)methyl] propanehydrazide, and CAS number 14919-77-8m and formula: C10H15N3O5, and Molecular mass of 257.243 g/mol.

In some embodiments, the dose of Benserazide used in the methods and compositions as disclosed herein is at least about 0.5 mg/kg, or between about 0.5 mg/kg and 1 mg/kg, or at least about 0.5 mg/kg, or at least about 1.0 mg/kg or at least about 2.0 mg/kg, or at least about 3.0 mg/kg, or at least about 4.0 mg/kg, or at least about 5.0 mg/kg or greater than 5.0 mg/kg, for example, between 5-10 mg/kg. In some embodiments, a dose of benserazide used in the methods and compositions as disclosed herein is between the range of about 0.1-0.5 mg/kg, or about 0.5 mg/kg-1.0 mg/kg, or 1.0 mg/kg-2.0 mg/kg, or 2.0 mg/kg-3.0 mg/kg, or 3.0 mg/kg-4.0 mg/kg, or about 4.0 mg/kg-5.0 mg/kg, or about between 5-10 mg/kg.

In some embodiments, a dose of Benserazide used in the methods and compositions as disclosed herein is at least about 0.1 µM, or at least about 0.3 µM, or at least about 0.5 µM, or at least about 1.0 µM, or at least about 2.0 µM, or at least about 3.0 µM or greater than 4.0 µM, or at least about 5.0 µM, or at least about 6.0 µM, or at least about 7.0 µM, or at least about 8.0 µM, or at least about 9.0 µM, or at least about 10.0 µM or any integer between about 0.1 µM and 10 µM.

Desloratadine

Desloratadine, known as β-chloro-2-(piperidin-4-ylidene)-4-azatricyclo[9.4.0.0^{3,8}]pentadeca-1(11),3,5,7,12,14-hexaene or 8-Chloro-6,11-dihydro-11-(4-piperidinylidene)-5H-benzo[5,6]cyclohepta[1,2-b]pyridine, has the following structure:

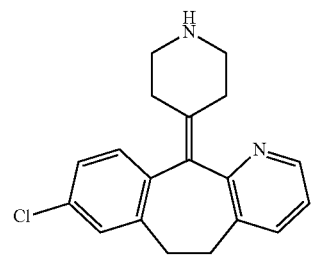 [SMILES: Clc1ccc2c(c1)CCc1cccnc1C2=C1CCNCC1]

Desloratadine is currently marketed as CLARINEX™ and other trade names such as NEOCLARITYN™, CLARAMAX™, LARINEX™, AERIUS™, DAZIT™, AZOMYR™ and DELOT™. in the United States. CLARINEX™ is prescribed as an antihistamine for prevention or treatment of allergenic reactions, which may result in symptoms such as sneezing, itchy eyes and hives. U.S. Pat. No. 4,659,716, which is incorporated herein in its entirety by reference discloses descarbonylethoxyloratadine (also known as Desloratadine), which possesses antihistaminic properties with substantially no sedative properties. The U.S.

Pat. No. 4,659,716 describes a process for the preparation of Desloratadine by dissolving loratadine in water and basifying with dilute solution of potassium carbonate to obtain a pink coloured oil. The organic material is extracted with chloroform, washed with water and triturated with hexane. Desloratadine is obtained by recrystallisation of the extracted organic material with large volume of hexane after charcolisation.

U.S. Pat. No. 6,506,767 (hereinafter '767) which is incorporated herein in its entirety by reference, discloses two polymorphic forms of desloratadine, labeled Forms I and II. The XRPD peaks and the FTIR spectrum for the forms are also disclosed in the '767 patent. According to this '767 patent, discloses certain alcoholic solvents, e.g., hexanol and methanol produce 100% polymorph form 1, but others, e.g., 3-methyl-1-butanol and cyclohexanol produce significant amounts of form 2. Chlorinated solvents, e.g., dichloromethane produce form 1 substantially free of form 2. Ether solvents such as dioxane produced form 1 substantially free of form 2 but other alkane ethers, e.g., di-isopropyl ether produced form 1 with significant amounts of form 2 and di-n-butyl ether favored formation of form 2. Ketones such as methyl isobutyl ketone produced crystalline polymorph form 1 essentially free of form 2 but methyl butyl ketone produced 8:1 ratio of form 1 to form 2. Use of methyl isobutyl ketone is preferred to produce crystalline polymorph form 1 essentially free of form 2. Only ethyl acetate and di-n-butyl ether were found to produce crystalline polymorph form 2 substantially free of form 1. Use of di-n-butyl ether is preferred for producing crystalline form 2 substantially free of form 1. According to this patent the polymorph form obtained from U.S. Pat. No. 4,659,716 is a mixture of form I and form II.

Teva Patent WO2004/080461, which is incorporated herein in its entirety by reference, claims a pharmaceutical composition of desloratadine comprising of a mixture of crystalline Desloratadine of form I and II in a weight to weight ratio of about 25% to about 75% of either form to the other and a pharmaceutically acceptable excipient.

Desloratadine or its pharmaceutically acceptable salts thereof can be used in the methods and compositions as disclosed herein, and are well known in the art and is disclosed and can be manufactured as taught in the following U.S. Patent Applications, 2010/0129310; 2010/0216831; 2010/0069402; 2010/0022576; 2010/0021542; 2008/0118555; 2007/0244144; 2007/0135472; 2007/0060756; 2007/0053974; 2007/0014855; 2007/0004671; 2006/0276495; 2006/0223841; 2006/0154948; 2006/0100435, which are incorporated herein in their entirety by reference.

In some embodiments, the dose of Desloratadine used in the methods and compositions as an HbF-inducer as disclosed herein is at least about 0.2 mg/kg, or about 0.4 mg/kg, or between about 0.4 mg/kg and 0.6 mg/kg, or at least about 0.6 mg/kg, or at least about 0.8 mg/kg or at least about 1.0 mg/kg or greater than 1.0 mg/kg. In some embodiments, a dose of benserazide used in the methods and compositions as disclosed herein is between the range of about 0.4 mg/kg-0.6 mg/kg, or 0.6 mg/kg-0.8 mg/kg, or 0.8 mg/kg-1.0 mg/kg, or 2.0 mg/kg and 3.0 mg/kg. In some embodiments, the dose of Desloratadine used in the methods and compositions as an HbF-inducer as disclosed herein is administered at 0.5 mg/kg, or 1 mg/kg, or 1.5 mg/kg, or 2.0 mg/kg. In some embodiments, the dose desloratadine can be administered twice a day, daily, every other day (bid), or weekly. In some embodiments, the dose of desloratadine can be between 35-150 mg per day. In some embodiments, a subject is selected for treatment with desloratadine that has a blood disorder, or hemoglobin disorder or cytopenia or in need of increased red blood cells.

In some embodiments, a dose of Desloratadine used in the methods and compositions as disclosed herein is at least about 5 nM, or at least about 10 nM, or at least about 50 nM, or at least about 100 nM, or at least about 200 nM, or at least about 300 nM, or at least about 400 nM, or at least about 500 nM, or at least about 600 nM, or at least about 700 nM, or at least about 800 nM, or at least about 900 nM, or at least about 1 µM, or at least about 1 µM, or at least about 3 µM or greater than 3 µM, or any integer between 5 nM and 3 µM.

MS-275

MS-275 is also called MS-27-275 or N-(2-aminophenyl)-4-[N-(pyridin-3-yl-methoxycarbonyl)aminomethyl]benzamide or 3-pyridinylmethyl[[4-[[(2-aminophenyl)amino]carbonyl]phenyl]methyl]carbamate, which has the following structure:

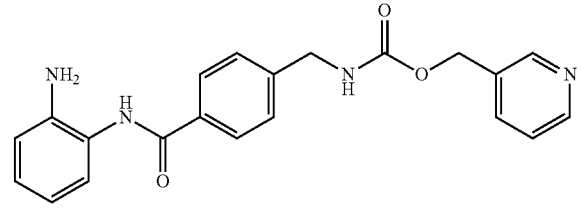 [SMILES: Nc1ccccc1NC(=O)c1ccc(CNC(=O)OCc2cccnc2)cc1]

MS-275 is also commonly known in the art as ENTINOSTAT™ or SNDX-275, and is an orally bioavailable, highly selective, class I histone deacetylase (HDAC) inhibitor with a long half-life that allows for weekly or every-other-week dosing. Entinostat is currently being investigated in multiple phase 2 clinical studies: in advanced breast cancer in combination with aromatase inhibitors; in combination with erlotinib in metastatic lung cancer and as a single agent in Hodgkin's lymphoma. Entinostat also is being studied in advanced non-small-cell lung cancer and in advanced colorectal cancer in combination with azacitidine under a Cooperative Research and Development Agreement (CRADA) with the NCI.

MS-275 is a synthetic benzamide derivative that has been shown to inhibit cellular histone deacetylase activity and to block growth in a variety of human tumor cell lines (A. Saito, et al., 1999, Proc. Natl. Acad. Sci. USA, A synthetic inhibitor of histone deacetylase, MS-27-275, with marked in vivo anti-tumor activity against human tumors, 96:4592-7). The chemical structure of MS-275 is shown as structure I in the Summary of the Invention section of this application. MS-275 is chemically synthesized using methods known in the art. One such method is described in T. Suzuki et al., 1999, J. Med. Chem., Synthesis and histone deacetylase inhibitory activity of new benzamide derivatives, 42:3001-3. Additional information relating to synthesis of MS-275 and related compounds is found in Japanese Unexamined Patent Publication Hei No. 10-152462. MS-275 is also available from various sources. One such source is Nihon Schering K.K. Another source is the National Cancer Institute (MS-275 is NSC No. 706995). Two benzamide derivatives closely related to MS-275 are shown as structures II and III in the Summary of the Invention section of this application.

MS-275 can have derivatives as shown as structures (I), (II) and (III), in U.S. Pat. No. 6,841,565, which is incorporated herein in its entirety by reference and are shown below:

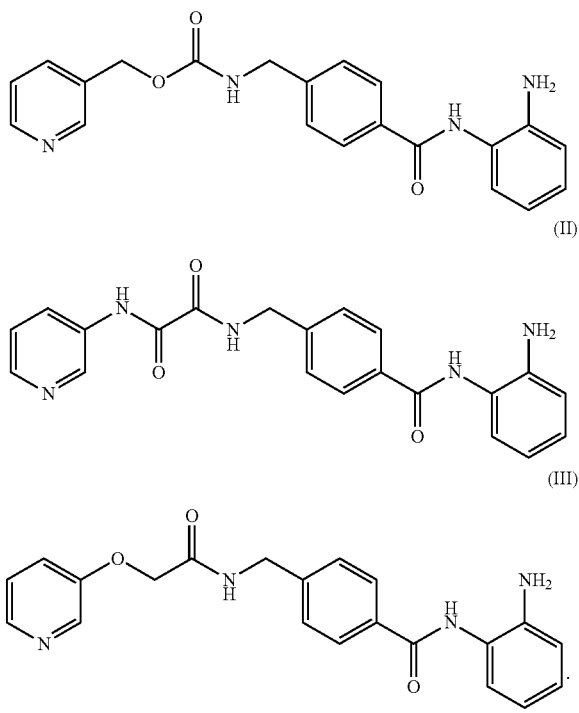

In addition to the MS-275 derivatives shown above, MS-275 derivatives can be pharmaceutically acceptable salts of the benzamide derivatives for use in practice of the invention. Such salts include salts with an inorganic acid such as hydrochloric acid, hydrobromic acid, sulfuric acid and phosphoric acid; and with an organic acid such as acetic acid, lactic acid, tartaric acid, malic acid, succinic acid, fumaric acid, maleic acid, citric acid, benzoic acid, trifluoroacetic acid, p-toluenesulfonic acid and methanesulfonic acid. Such salts include N-(2-aminophenyl)-4-(N-(pyridin-3-yl)methoxycarbonylaminomethyl)benzamide hydrochloride, N-(2-aminophenyl)-4-(N-(pyridin-3-yl)methoxycarbonylaminomethyl)benzamidehydrobromide, N-(2-aminophenyl)-4-(N-(pyridin-3-yl)methoxycarbonylaminomethyl)benzamide sulfate, N-(2-aminophenyl)-4-(N-(pyridin-3-yl)methoxycarbonylaminomethyl)benzamide phosphate, N-(2-aminophenyl)-4-(N-(pyridin-3-yl)methoxycarbonylaminomethyl)benzamide acetate, N-(2-aminophenyl)-4-(N-(pyridin-3-yl)methoxycarbonylaminomethyl)benzamide lactate, N-(2-aminophenyl)-4-(N-(pyridin-3-yl)methoxycarbonylaminomethyl)benzamide tartrate, N-(2-aminophenyl)-4-(N-(pyridin-3-yl)methoxycarbonylaminomethyl)benzamide malate, N-(2-aminophenyl)-4-(N-(pyridin-3-yl)methoxycarbonylaminomethyl)benzamide succinate, N-(2-aminophenyl)-4-(N-(pyridin-3-yl)methoxycarbonylaminomethyl)benzamide fumarate, N-(2-aminophenyl)-4-(N-(pyridin-3-yl)methoxycarbonylaminomethyl)benzamide maleate, N-(2-aminophenyl)-4-N-(pyridin-3-yl)methoxycarbonylaminomethyl)benzamide citrate, N-(2-aminophenyl)-4-(N-(pyridin-3-yl)methoxycarbonylaminomethyl)benzamide trifluoroacetate, N-(2-aminophenyl)-4-(N-(pyridin-3-yl)methoxycarbonylaminomethyl)benzamide p-toluenesulfonate and N-(2-aminophenyl)-4-(N-(pyridin-3-yl)methoxycarbonylaminomethyl)benzamide methanesulfonate, and others.

A polymorph of MS-275 is disclosed in GB patent GB0907347.9 entitled N-(2-aminophenyl)-4-[N-(pyridine-3-YL)-methoxycarbonyl-aminomethyl]-benzamide (MS-275) polymorph B, which is incorporated herein in its entirety by reference.

In some embodiments, the dose of MS-275 for use in the methods and compositions as an HbF-inducer as disclosed herein is at least about 1 mg/m$^2$, or at least about 2 mg/m$^2$, or at least about 3 mg/m$^2$, or at least about 4 mg/m$^2$, or at least about 5 mg/m$^2$ or between about 1 mg/m$^2$ and 4 mg/m$^2$, or greater than 4 mg/m$^2$.

In some embodiments, the dose of MS-275 for use in the methods and compositions as an HbF-inducer as disclosed herein is administered at about 0.05 mg/kg, or about 0.1 mg/kg, or about 0.2 mg/kg, or about 0.3 mg/kg, or about 0.4 mg/kg, or about 0.5 mg/kg, or about 0.6 mg/kg, or about 0.7 mg/kg, or about 0.8 mg/kg, or about 0.9 mg/kg, or about 1.0 mg/kg, or about 2.0 mg/kg or between about 0.1 mg/kg and 1 mg/kg, or between about 1 mg/kg-2 mg/kg, or between about 2 mg/kg and 5 mg/kg, or between about 5 mg/kg and 10 mg/kg, or between about 10-15 mg/kg, or between about 10-20 mg/kg, or any integer between 0.05 mg/kg and 20 mg/kg. In some embodiments, a dose of MS-275 used in the methods and compositions as disclosed herein is between the range of about 0.01 mg/kg-0.05 mg/kg, or 0.05 mg/kg-0.1 mg/kg, or 0.1 mg/kg-1.0 mg/kg, or between 1.0 mg/kg-2.0 mg/kg, or between 0.1 mg/kg and 10 mg/kg. In some embodiments, the dose can be administered twice a day, daily, every other day (bid), or weekly.

Treatment of Diseases

In one embodiment, the invention relates to compositions useful in the treatment and prevention of blood disorders such as anemia, thalassemia, and sickle cell disease. Compositions as disclosed herein stimulate the specific expression of a γ-globin protein, without inhibiting cell proliferation, and can increase the development of hemoglobin-expressing or other myeloid cells.

Beta Thalassemias

Thalassemia syndromes result from deficiencies in either alpha-globin (β-thalassemia) or beta-like globin (β-thalassemia) chains. The diseases become apparent when the deficient globin is required during development. β-Thalassemia is symptomatic during gestation, as γ-globin is required for fetal hemoglobin (HbF, α2,γ2). As γ-globin is not required in large amounts before birth, β-thalassemia is asymptomatic until around 6 months after birth. Mutations that cause prolonged production of fetal γ-globin chains may present later, at 2 to 4 years of age.

The major pathologic process in thalassemia is the imbalance of alpha and non-alpha globin chain accumulation. The unaffected chains, produced in normal amounts, precipitate during erythropoiesis. In β-thalassemia, the precipitated γ-globin chains are particularly toxic, damaging cell membranes and causing rapid cell death (apoptosis). Red blood cell life-span is further shortened by removal of abnormal cells in the reticuloendothelial system. Erythropoietin levels increase, causing erythroid hyperplasia. Hypersplenism causes more severe anemia.

Beta globin is made by two genes, one on each chromosome 11. The beta thalassemia syndromes are caused by more than 175 molecular mutations affecting the beta globin gene complex. Each beta globin gene comprises three exons which encode about 146 amino acids, two introns, and a 5'-untranslated region containing the promoter sequences. Biosynthesis of beta globin begins with transcription of the entire gene followed with RNA processing of the message, removal of the introns by splicing, poly A addition, capping and post-transcriptional modifications. The mature mRNA molecule is exported from the nucleus and translated into beta globin. Defects in each of these functions have been found associated with specific thalassemias. Identified mutations include single-nucleotide deletions, insertions and substitutions, frame shift mutations, deletions of entire segments of coding or controlling regions, improper termination signals, aberrant splicing signals, and multiple mutations.

β0-Thalassemias are characterized by a complete absence of any beta globin chains. β+-Thalassemias are characterized by detectable presence of a reduced amount of beta chains. There are three principal categories of beta thalassemias: thalassemia major, thalassemia intermedia, and thalassemia minor Thalassemia syndromes are graded according to severity of the anemia. Thalassemia major, in which severe anemia manifests during infancy, is caused by inheritance of two severely impaired beta-globin alleles. Such homozygous or doubly heterozygous conditions have milder manifestations when there is an increase in fetal globin chain production, or when the co-inheritance of alpha thalassemia decreases the net imbalance of alpha-globin to beta-globin. Thalassemia trait (inheritance of a single defective allele) is characterized by mild hypochromic, microcytic anemia and does not require treatment. Thalassemia intermedia (TI) causes moderate anemia with total hemoglobin levels of 6.0 to 10.0 grams per dL. These patients require occasional transfusions with infections, but do not require regular transfusions during childhood, although many deteriorate later in life, and develop similar complications as in thalassemia major.

The beta thalassemia trait can also combine with variant hemoglobins to produce other related blood disorders. Hemoglobin E trait is one of the most common abnormal hemoglobins. In some instances, a person carries the beta thalassemia trait and the hemoglobin E trait, which leads to HbE beta thalassemia, a moderately severe anemia that has similar symptoms to beta thalassemia intermedia but on occasion may be as severe as thalassemia major. It is usually found in people of Southeast Asian ancestry, such as Cambodians, Vietnamese, and That.

In certain instances, a person carries the beta thalassemia trait and the hemoglobin S trait (the abnormal hemoglobin found in people with sickle cell disease), which leads to HbS beta thalassemia. The severity of this condition varies according to the amount of normal beta globin produced by the beta globin gene. When no beta globin is produced by the beta globin gene, the condition is almost identical to sickle cell disease. When some beta globin is produced by the beta globin gene, the condition is less severe. Hemoglobin S trait is commonly found in people of African or Mediterranean ancestry, such as Africans, Italians, Greeks, Turks, and in people from the Caribbean.

In β-thalassemia major, red blood cell (RBC) transfusion is the mainstay of supportive therapy. Transfusions should maintain a hemoglobin level ideally above 10.5 to 11 g/dL (range 10.5 to 13 g/dL). Transfusions can transmit infections, including hepatitis viruses, HIV, CMV, and other pathogens. Further complications from transfusion therapy arise when iron deposition causes dysfunction in the heart, liver, and endocrine organs. Glucose intolerance with insulin-dependent diabetes mellitus, primary hypothyroidism, hypoparathyroidism, delayed puberty, amenorrhea, and osteopenia, are common; arrhythmias are often precipitated by cardiac hemosiderosis and hypocalcemia secondary to hypoparathyroidism. Growth retardation may respond to Growth Hormone before 13 years of age. Hepatic iron and hepatitis C lead to fibrosis and cirrhosis. Cardiac dysfunction is detectable early by cardiovascular magnetic resonance and T2*measurements <20 ms and reduced ejection fractions, and presents with fatigue, arrhythmias, or pericarditis, advancing to congestive heart failure, the major cause of death in transfused patients (60%), followed by infections (13%), and liver disease, including hepatocellular carcinoma (6%) Pulmonary hypertension develops in untransfused intermedia patients with hemolysis; a TR jet velocity >2 is associated with 25% mortality.

Osteopenia occurs in approximately 55% of thalassemia major and intermedia patients. In certain instances, it is severe and causes fractures, and even occurs in transfused patients in early childhood. In some instances, affected patients are maintained on elemental calcium (1500 mg per day) and vitamin D (400 IU per day). In certain instances, osteoporosis is treated with bisphosphonates.

Patients should be monitored for marrow expansion, facial deformity, splenomegaly, growth retardation, endocrinopathies, and osteopenia. Pulmonary hypertension is a recently recognized risk, related to chronic hemolysis in untransfused patients. Tricuspid regurgitation (TR jet of >2) is associated with a 25% mortality, for which transfusions should be instituted. Patients with β+ thalassemia and baseline erythropoietin levels <130 mU/mL, require erythropoietin and a fetal globin stimulant.

The hyperplastic marrow in thalassemia intermedia stimulates intestinal iron absorption and eventually iron overload and endocrine deficiencies occur as in thalassemia major, although more slowly, and cardiomyopathy does not develop in untransfused patients. Avoidance of iron-rich meats and regular consumption of tea can reduce iron absorption. Osteopenia occurs in 55% of major and intermedia patients. Hypercoagulability and thromboembolic events occur particularly in splenectomized patients, related to thrombocytosis and hepatic dysfunction. Folic acid and antioxidant supplements should be used. Spinal cord compression syndromes from thoracic or vertebral paraspinal bone marrow masses should be suspected with acute or increasing weakness, numbness, and diminished reflexes in the lower extremities, a medical emergency.

In some instances, tests to determine the genotypes of beta thalassemia in a patient include, but are not limited to, hemoglobin electrophoresis, globin chain electrophoresis, molecular mutation analysis, family studies, and quantitative trait loci (QTL) analysis.

In certain instances, disruption of the beta globin gene complex results in decreased synthetic ratios of non-alpha to alpha globin chains, precipitation of excess unbalanced alpha globin chains, and programmed cell death of erythroblasts early in their development. Affected patients do not become anemic until the fetal (gamma) globin genes are developmentally silenced. Patients with persistent high levels of fetal globin typically have less severe anemia, milder clinical syndromes, and are often transfusion-independent. The beta thalassemias are thus one of a few clinical conditions in which a gene that is transiently expressed during fetal life can functionally replace a mutant gene normally expressed later in development. Reactivation of fetal (gamma) globin expression is appealing as a therapeutic approach to the beta thalassemias, because the fetal globin genes are universally present and appropriately contextually integrated in the beta globin locus in hematopoietic stem cells in virtually all humans.

Sickle Cell Disease

In sickle cell disease (SCD), one amino acid substitution in the beta globin chain results in the generation of hemoglobin S (HbS). Upon deoxygenation, HbS molecules undergo aggregation and polymerization ultimately leading to a morphological distortion of the red cells which acquire a sickle or holly-leaf shape. Sickling has two major consequences, a chronic hemolytic anemia and an occlusion of small blood vessels that results in ischemic damage to tissues. Further, when exposed to low oxygen tensions, polymerization converts blood containing HbS from a free flowing liquid to a viscous gel. Consequently, in certain instances, the degree of pathology associated with sickle cell disease is correlated with the relative amount of HbS in the patient's system. HbS polymerization is also significantly affected by the hemoglobin concentration in the cell. The higher the HbS concentration, the greater is the chance for contact between two or more HbS molecules. In some instances, dehydration increases hemoglobin concentration and greatly facilitates sickling.

To some extent, sickling is a reversible phenomenon. With increased oxygen tensions, sickled cells depolymerize. This process of polymerization-depolymerization is very damaging to red cell membranes and eventually leads to irreversibly sickled cells (ISC), which retain their abnormal shape even when fully oxygenated. The average ISC survives for about 20 days in the body, as compared to the normal 120 day life span.

Individuals with HbS syndromes have frequent infections, chronic hemolysis with a striking reticulocytosis and hyperbilirubinemia. The course of the disease is typically punctuated with a variety of painful crises called vaso-occlusive crises. These crises represent episodes of hypoxic injury and infarction in the organs, abdomen, chest, extremities, or joints. Leg ulcers are an additional manifestation of vaso-occlusive tendency of this disease. Central nervous system involvement is common producing seizures and even strokes. Aplastic crises, also common, represent a temporary cessation of bone marrow activity and, in certain instances, are triggered by infections, folic acid deficiency, or both. Crises are episodic and reversible, but may be fatal. Damage from crisis episodes tends to be cumulative and even in those individuals with milder forms of sickle cell disease life-spans can be greatly reduced. Absent alternative intervention, patients typically die before the age of 30.

Individuals with severe SCD develop no symptoms until about five to six months after birth. In these infants, fetal hemoglobin (HbF) does not interact with HbS and can modulate the effects of HbS, as long as sufficient quantities of HbF are present. HbF levels above 20% are generally considered to be sufficient to eliminate symptoms associated with sickle cell disease.

Blood Disorders.

In another embodiment, the invention relates to methods and medical aids which utilize these compositions to treat blood disorders and/or to ameliorate symptoms associated with blood disorders.

The term "blood disorders" as used herein includes hemoglobinopathies and thalassemias. Blood disorders include disorders that can be treated, prevented, or otherwise ameliorated by the administration of a compound of the invention. A blood disorder is any disorder of the blood and blood-forming organs. The term blood disorder includes nutritional anemias (e.g., iron deficiency anemia, sideropenic dysphasia, Plummer-Vinson syndrome, vitamin B12 deficiency anemia, vitamin B12 deficiency anemia due to intrinsic factor, pernicious anemia, folate deficiency anemia, and other nutritional anemias), myelodysplastic syndrome, bone marrow failure or anemia resulting from chemotherapy, radiation or other agents or therapies, hemolytic anemias (e.g., anemia due to enzyme disorders, anemia due to phosphate dehydrogenase (G6PD) deficiency, favism, anemia due to disorders of glutathione metabolism, anemia due to disorders of glycolytic enzymes, anemias due to disorders of nucleotide metabolism and anemias due to unspecified enzyme disorder), thalassemia, α-thalassemia, β-thalassemia, δβ-thalassemia, thalassemia trait, hereditary persistence of fetal hemoglobin (HPFP), and other thalassemias, sickle cell disorders (sickle cell anemia with crisis, sickle cell anemia without crisis, double heterozygous sickling disorders, sickle cell trait and other sickle cell disorders), hereditary hemolytic anemias (hereditary spherocytosis, hereditary elliptocytosis, other hemoglobinopathies and other specified hereditary hemolytic anemias, such as stomatocyclosis), acquired hemolytic anemia (e.g., drug-induced autoimmune hemolytic anemia, other autoimmune hemolytic anemias, such as warm autoimmune hemolytic anemia, drug-induced non-autoimmune hemolytic anemia, hemolytic-uremic syndrome, and other non-autoimmune hemolytic anemias, such as microangiopathic hemolytic anemia); aplastic anemias (e.g., acquired pure red cell aplasia (erythroblastopenia), other aplastic anemias, such as constitutional aplastic anemia and fanconi anemia, acute posthemorrhagic anemic, and anemias in chronic diseases), coagulation defects (e.g., disseminated intravascular coagulation (difibrination syndrome)), hereditary factor VIII deficiency (hemophilia A), hereditary factor IX deficiency (Christmas disease), and other coagulation defects such as Von Willebrand's disease, hereditary factor Xi deficiency (hemophilia C), purpura (e.g., qualitative platelet defects and Glanzmann's disease), neutropenia, agranulocytosis, functional disorders of polymorphonuclear neutrophils, other disorders of white blood cells (e.g., eosinophilia, leukocytosis, lymphocytosis, lymphopenia, monocytosis, and plasmacyclosis), diseases of the spleen, methemoglobinemia, other diseases of blood and blood forming organs (e.g., familial erythrocytosis, secondary polycythemia, essential thrombocytosis and basophilia), thrombocytopenia, infectious anemia, hypoproliferative or hypoplastic anemias, hemoglobin C, D and E disease, hemoglobin lepore disease, and HbH and HbS diseases, anemias due to blood loss, radiation therapy or chemotherapy, or thrombocytopenias and neutropenias due to radiation therapy or chemotherapy, sideroblastic anemias, myelophthisic anemias, antibody-mediated anemias, and certain diseases involving lymphoreticular tissue and reticulohistiocytic system (e.g., Langerhans' cell hystiocytosis, eosinophilic granuloma, Hand-Schuller-Christian disease, hemophagocytic lymphohistiocytosis, and infection-associated hemophagocytic syndrome).

Accordingly, as disclosed herein, compositions comprising the compounds as disclosed herein can be administered to a subject to treat a blood disorder, where a blood disorder is any disease or malady which could be characterized as a direct or indirect consequence of a defect or disease of hemoglobin producing cells or the production of hemoglobin. The blood disorder may be associated with an anemia such as sickle cell anemia, hemolytic anemia, infectious anemia, aplastic anemias, hypoproliferative or hypoplastic anemias, sideroblastic anemias, myelophthisic anemias, antibody-mediated anemias, anemias due to enzyme-deficiencies or chronic diseases, anemias due to blood loss, radiation therapy or chemotherapy, thalassemias including α-like and β-like thalassemias, or globin disorders due to infections of viral, bacterial or parasitic origin such as malaria, trypanosomiasis, human immunodeficiency virus and other retroviruses, a polyoma virus such as JC virus, or a hepatitis virus such as human hepatitis viruses types A-G. Treatable blood disorders also include syndromes such as hemoglobin C, D and E disease, hemoglobin lepore disease, and HbH and HbS diseases. Treatment ameliorates one or more symptoms associated with the disorder. Symptoms typically associated with blood disorders include, for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic crises and pain such as angina pectoris. Compositions provided to the subject may include any combination of the proteins or chemical compounds of the invention or known to those of ordinary skill in the art. The subject may be a domesticated animal such as a dog, cat, horse, cow, steer, pig, sheep, goat or chicken, or a wild animal, but is preferably a human. Administration may be to an adult, an adolescent, a child, a neonate, an infant or in utero. Administration of the composition may be short term, continuous or sporadic as necessary. Patients with a suspected or diagnosed with a blood disorder may only require composition treatment for short periods of time or until symptoms have abated or have been effectively eliminated.

In some embodiments, the blood deficiencies are acquired or genetic deficiencies. Genetic blood disorders are well known by persons of ordinary skill in the art, and include, without limitation, Thalassemias, Sickle cell disease, hereditary spherocytosis, G6PD Deficiency hemolytic anemia, Kostman's syndrome, Swachman-Diamond Syndrome, Cyclic neutropenia, Hereditary neutropenia, Dyskeratosis Congenita, Hereditary thrombocytopenia syndromes, Wiskott-Aldrich Syndrome, May-Hegglin anomaly, Thrombocytopenia with Absent Radii Syndrome, Fanconi's anemia and other hereditary blood disorders.

In some embodiments, the oral compositions of the HbF inducers as disclosed herein, e.g., any one or a combination of at least one or a combination of any of 2-amino-3-hydroxy-N'-(2,3,4-trihydroxybenzyl)propanehydrazide (Benserazide) or 8-Chloro-6,11-dihydro-11-(4-piperidinylidene)-5H-benzo[5,6]cyclohepta[1,2-b]pyridine (Desloratadine) or N-(2-aminophenyl)-4-[N-(pyridin-3-yl-methoxycarbonyl) aminomethyl]benzamide (MS-275), or any pharmaceutically acceptable salt, polymorph or ester thereof, can be used in methods for the treatment of neutropenia. Neutrophenia is a disorder of low white blood cell count in a subject, and is characterized by one or more of the following: an absolute neutrophil count (ANC) of less than 1500/microL. People suffering or diagnosed with neutrophia may result in hospitalization for treatment of fever, neutropenic sepsis, and can cause potentially fatal infection. Neutropenia is very common in subjects undergone or currently undergoing chemotherapy, transplants, radiation therapy and the like.

Current treatment for neutropenia are inadequate. Existing therapies include Granulocyte colony-stimulating factor (G-CSF, filgrastim) which, in 2008 US sales were about $929,201, Granulocyte-macrophage colony-stimulating factor (GM-CSF, sargramostim) which, in 2008 US sales were approximately $82,440, and Pegfilgrastim, a pegylated formulation of G-CSF, which in 2008 US sales were about $3,013,159.

Cytopenias

In some embodiments, the methods and compositions as disclosed herein can be used for the treatment of low platelet count, for example but not limited to, a low platelet count occurring in thrombocytopenia an/or platelet dysfunction. There is currently no or inadequate drug therapy, and the only current treatment is a platelet transfusion. In some embodiments, the methods and methods and compositions as disclosed herein can be used for the treatment of low platelet count which is occurs as a consequence of other disorders, for example but not limited to, AIDS (acquired immunodeficiency syndrome); ITP (immune thrombocytopenic purpura); DIC (disseminated intravascular coagulation); TTP (thrombotic thrombocytopenic purpura) and the like.

In some embodiments, the methods and methods and compositions as disclosed herein can be used for the treatment of cytopenias. Significant cytopenias are associated with radiation therapies and accidental exposures, and also occur after or during chemotherapy and chemo-radiation. It has been demonstrated that the duration of neutropenia in the Acute Radiation Syndrome particularly correlates with reduced survival, with a longer duration of neutropenia correlates with decreased survival. Although G-CSF and GM-CSF can be used to reduce duration of neutropenia, they are not routinely utilized for treatment of radiation-associated neutropenias due to numerous limitations, including commercial cost, and route of administration and need for the G-CSF and GM-CSF to be refrigerated.

Deficiencies of blood cells, frequently termed cytopenias, can affect cells of any or all hematopoietic lineage, including stem cells, red blood cells, white blood cells (myeloid cells), particularly neutropenias (deficiency of neutrophils, the cells which fight and control bacterial infections), or thrombocytopenias, (deficiencies of platelets, cells which initiate blood clotting).

Hematopoietic stem cells (HSCs) refer to stem cells or progenitor cells typically residing in the bone marrow that are capable of self-renewing and differentiating into any of the specific types of hematopoietic blood cells, including erythroid cells, myeloid or monocytic cells, megakaryocytes (platelet precursors), or lymphoid cells. Stem cells are responsible for the constant maintenance and proliferation, when needed, of all hematopoietic cell lineages.

Cytopenias can be caused by factors which suppress proliferation and differentiation of stem cells or of specific lineages. SUhc factors can include vial infections (such as hepatitis viruses A-G, human immunodeficiency virus, others), toxins, drugs, exposure to radiation or radiation accidents, chemotherapy, idiopathic etiologies (aplastic anemia), or genetic disorders such as Fanconi's anemia, severe or mild congenital neutropenias, Schwachman Diamond sundrome, Diamond Blackfan anemia, thrombocytopenia associated with viral infections or antibodies, and other conditions. Cytopenias always occur following stem cell or marrow transplantation.

Cytopenias place a subject at high risk of a serious or even fatal complication or outcome. Neutropenias are associated with serious bacterial infections which can be overwhelming rapidly and fatal; anemias are associated with hypoxia, poor exercise tolerance, poor growth, cardiac enlargement and failure, and even shock; thrombocytopenia is associated with severe bleeding. All of these conditions would benefit from treatment with a hematopoietic stimulant, particularly an oral stimulant which can be used without injections and can be stable at room temperature.

Accordingly, another embodiment of the present invention is a method and compositions as disclosed herein which can be used to enhance pan-hematologic recovery from radiation exposures, and have advantages of reduced cost, easy administration, long shelf life and no, or minimal need for refrigeration.

Figure 8:
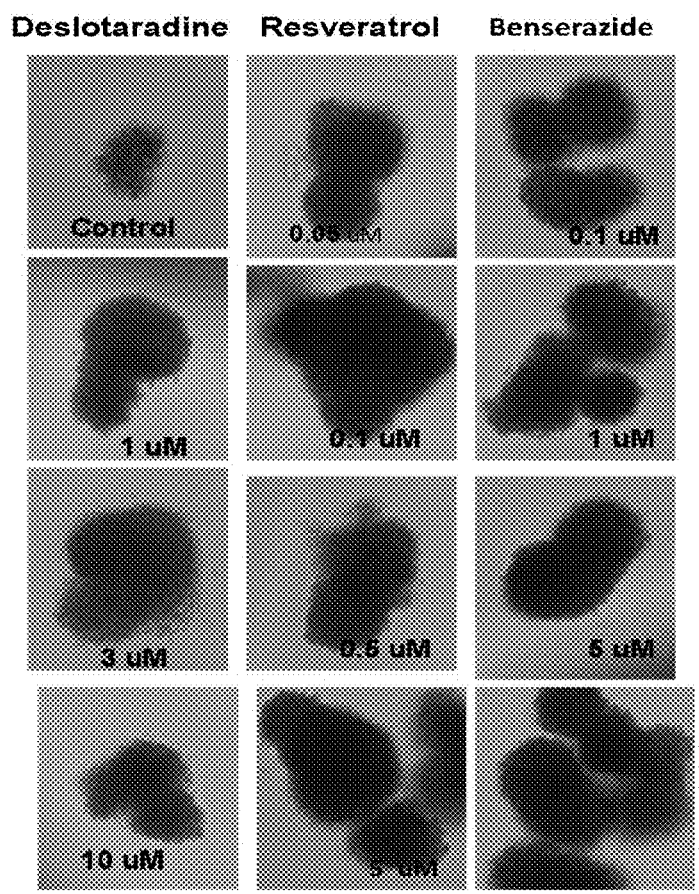
FIG. 8 shows the effect of different concentrations of Desloratadine, Resveratrol and Benserazide on CB BFU-E cell proliferation. Representative images of increased blood cells per colony (cells/colony) are shown after treatment with Desloratadine (1 μM-10 μM), Resveratrol (0.05 μM-5 μM) and Benserazie (0.1 μM-10 μM) showing that these compounds are non-cytotoxic compounds and do not inhibit erythroid cell proliferation. The 3 drug candidates assessed enhance erythroid growth at 1/100 to 1/1000 of the concentration required by Butyrate (200 μM) (e.g., they have higher potency for inducing γ-globin).

As demonstrated in FIG. 8, the HbF-inducer agents desloratadine, resveratrol and benserazine increase the number of blood cells per colony, and thus are useful inducers of hematopoiesis and erythroid expansion, or proliferation of red blood cells (erythropoiesis). Thus, in some embodiments the compounds of the present invention, e.g., at least one of, or any combination of HbF-inducing drugs, which include, ambroxol, 2-amino-3-hydroxy-N'-(2,3,4-trihydroxybenzyl) propanehydrazide (Benserazide), 8-Chloro-6,11-dihydro-11-(4-piperdinylidene)-5H-benzo[5,6]cyclohepta[1,2-b]pyridine (Desloratadine), resveratrol, NSC-95397, idarubicin or N-(2-aminophenyl)-4-[N-(pyridin-3-yl-methoxycarbonyl) aminomethyl]benzamide (MS-275), or auronafin are useful in methods to raise blood cell counts in vitro and in vivo, and as they demonstrate red blood cell stimulation activity (they induce erythropoiesis) in addition to inducing HbF expression, and can be used in the treatment of cytopenias and other anemias.

Another embodiment of the invention is directed to methods for the treatment of patients with blood disorder comprising the administration of one or more compositions of the invention. Compositions to be administered contain a therapeutically effective amount of a chemical compound. A therapeutically effective amount is that amount which has a beneficial effect to the subject by alleviating one or more symptoms of the disorder or simply reduce premature mortality. For example, a beneficial effect may be a decrease in pain, a decrease in duration, frequency or intensity of crises, an increased hemocrit, an improved erythropoiesis, an increased reticulocyte count, an increased peripheral blood flow, a decreased hemolysis, decreased fatigue or an increased strength. Preferably, a therapeutic amount is that amount of chemical compound or agent that stimulates or enhances the expression of non-adult globin such as embryonic or fetal globin (HbF), or the proliferation of embryonic, fetal or adult globin expressing cells. In some embodiments, a therapeutic amount is that amount of chemical compound or agent as disclosed herein that increases the percentage of expression of non-adult globin such as embryonic or fetal globin (HbF), or the proliferation of embryonic, fetal or adult globin expressing cells.

Administration

In some embodiments, compositions comprising at least one or any combination of ambroxol, benserazide, desloratadine, resveratrol, NSC-95397, idarubicin, MS-275, or auronafin, in particular benserazide, desloratadine or MS-275 can be directly or indirectly administered to the patient. Indirect administration can also be performed, for example, by administering the composition to cells ex vivo and subsequently introducing the treated cells to the patient. The cells may be obtained from the subject to be treated or from a genetically related or unrelated patient. Related patients offer some advantage by lowering the immunogenic response to the cells to be introduced. For example, using techniques of antigen matching, immunologically compatible donors can be identified and utilized.

Direct administration of compositions comprising at least one or any combination of ambroxol, benserazide, desloratadine, resveratrol, NSC-95397, idarubicin, MS-275, or auronafin, in particular benserazide, desloratadine or MS-275 can also be by oral, parenteral, sublingual, rectal such as suppository or enteral administration, or by pulmonary absorption or topical application. Parenteral administration may be by intravenous injection, subcutaneous injection, intramuscular injection, intra-arterial injection, intrathecal injection, intra peritoneal injection or direct injection or other administration to one or more specific sites. Injectable forms of administration are sometimes preferred for maximal effect in, for example, bone marrow. When long term administration by injection is necessary, venous access devices such as mediports, in-dwelling catheters, or automatic pumping mechanisms are also preferred wherein direct and immediate access is provided to the arteries in and around the heart and other major organs and organ systems.

In some embodiments, a composition comprising at least one or any combination of ambroxol, benserazide, desloratadine, resveratrol, NSC-95397, idarubicin, MS-275, or auronafin, in particular benserazide, desloratadine or MS-275 can be administered by transdermal transfusion such as with a dermal or cutaneous patch, by direct contact with, for example, bone marrow through an incision or some other artificial opening into the body. Compositions may also be administered to the nasal passages as a spray. Arteries of the nasal area provide a rapid and efficient access to the bloodstream and immediate access to the pulmonary system. Access to the gastrointestinal tract, which can also rapidly introduce substances to the blood stream, can be gained using oral, enema, or injectable forms of administration. Compositions may be administered as a bolus injection or spray, or administered sequentially over time (episodically) such as every two, four, six or eight hours, every day (QD) or every other day (QOD), or over longer periods of time such as weeks to months. Compositions may also be administered in a timed-release fashion such as by using slow-release resins and other timed or delayed release materials, coatings and devices.

Orally active compositions comprising at least one or any combination of ambroxol, benserazide, desloratadine, resveratrol, NSC-95397, idarubicin, MS-275, or auronafin, in particular benserazide, desloratadine or MS-275 are more preferred as oral administration is usually the safest, most convenient and economical mode of drug delivery. Oral administration is usually disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity. This can often be accomplished by formulating a composition with a complimentary reagent which neutralizes its polarity, or by modifying the compound with a neutralizing chemical group. Oral bioavailability is also a problem because drugs are exposed to the extremes of gastric pH and gastric enzymes. These problems can be overcome in a similar manner by modifying the molecular structure to withstand very low pH conditions and resist the enzymes of the gastric mucosa such as by neutralizing an ionic group, by covalently bonding an ionic interaction, or by stabilizing or removing a disulfide bond or other relatively labile bond.

Treatments to the subject may be therapeutic or prophylactic. Therapeutic treatment involves administration of one or more compositions of the invention to a subject suffering from one or more symptoms of the disorder. Symptoms typically associated with blood disorders include, for example, anemia, tissue hypoxia, organ dysfunction, abnormal hematocrit values, ineffective erythropoiesis, abnormal reticulocyte count, abnormal iron load, splenomegaly, hepatomegaly, impaired peripheral blood flow, dyspnea, increased hemolysis, jaundice, anemic crises and pain such as angina pectoris. Relief and even partial relief from one or more of these symptoms corresponds to an increased life span or simply an increased quality of life. Further, treatments that alleviate a pathological symptom can allow for other treatments to be administered.

Prophylactic treatments involve administration of a composition of the invention to a subject having a confirmed or suspected blood disorder without having any overt symptoms. For example, otherwise healthy patients who have been genetically screened and determined to be at high risk for the future development of a blood disorder may be administered compositions of the invention prophylactically. Administration can begin at birth and continue, if necessary, for life. Both prophylactic and therapeutic uses are readily acceptable because these compounds are generally safe and non-toxic.

Another embodiment of the invention is directed to a method for regulating the expression of a globin gene in a mammalian cell. Briefly, the cell is exposed to an effective amount of a compositions comprising at least one or any combination of ambroxol, benserazide, desloratadine, resveratrol, NSC-95397, idarubicin, MS-275, or auronafin, in particular benserazide, desloratadine or MS-275. A poorly expressed or quiescent globin gene of the cell is stimulated to increase the expression of its protein product. An effective amount of a composition comprising at least one or any combination of ambroxol, benserazide, desloratadine, resveratrol, NSC-95397, idarubicin, MS-275, or auronafin, in particular benserazide, desloratadine or MS-275 is the amount which increases the extent or magnitude of hematopoiesis, increases the proliferation of hemoglobin expressing cells, increases, decreases or balances expression from one or more globin genes, or increases or stimulates the specific expression of one or more globin genes such as an alpha ($\alpha$) globin gene, a zeta (.zeta.) globin gene, an epsilon ($\epsilon$) globin gene, a beta ($\beta$) globin gene, a delta ($\delta$) globin gene, a gamma (G-$\gamma$ or A-$\gamma$) globin gene, or an, at least, partly functional pseudo-globin gene. Cells, e.g., blood, can be treated in culture or in vivo. In some embodiments, blood is removed from a subject, treated ex vivo and reintroduced to the subject. Cultures of treated cells will produce increased amounts of hemoglobin and preferably embryonic or fetal globin. This hemoglobin can be harvested for introduction to a subject or the stimulated cells themselves can be administered to the patient. Alternatively, recombinant cells containing a globin gene which can be stimulated by compositions of the invention can be utilized. These recombinant cells may be heterologous or homologous natural cells, or synthetically created cells such as a lipid vesicles.

Another embodiment of the invention is directed to a method for regulating the proliferation of hemoglobin expressing cells. As above, an effective amount of a composition comprising at least one or any combination of ambroxol, benserazide, desloratadine, resveratrol, NSC-95397, idarubicin, MS-275, or auronafin, in particular benserazide, desloratadine or MS-275 as disclosed herein can be used to expose to cells ex vivo or administered to cells in vivo. These cells or purified products harvested from these cells can be utilized to treat blood disorders by administration to patients. For example, increasing the amount of one or more different types of globin or hemoglobin expressing cells can alleviate symptoms associated with a blood disorder. Cells can be obtained from volunteers or the patients to be treated. Alternatively, treated cells or products derived from treated cells can be harvested, purified by, for example, column chromatography, and utilized for other medical applications such as diagnostic or other treatment monitoring screening kits.

Another embodiment of the invention is directed to a method for ameliorating a blood disorder by administering a therapeutically effective amount of a pharmaceutical composition comprising at least one or any combination of ambroxol, benserazide, desloratadine, resveratrol, NSC-95397, idarubicin, MS-275, or auronafin, in particular benserazide, desloratadine or MS-275 as disclosed herein that stimulates the expression of a globin gene or stimulates the proliferation of hemoglobin expressing cells wherein the composition does not significantly decrease viability of the cell being treated or a normal cell. The therapeutically effective amount is that amount which ameliorates one or more symptoms of the blood disorder or reduces premature mortality. A normal cell is a relatively healthy mammalian cell that is not otherwise infected or transformed. Viability can be assayed by determining the effect of the composition on cell division, protein or nucleic acid synthesis, biochemical salvage pathways, amino acid or nucleotide transport processes, nucleic acid fragmentation or apoptosis and comparing the effects observed to control cells. Effects of the compositions can be tested in tissue culture or in vivo.

Patients with blood disorders are typically quite infirm with, for example, iron damaged organs and systems. Most treatments further tax the patient's already frail health in an effort to combat the disorder. This is true for both arginine butyrate and isobutyramide which decrease cell viability as determined in DNA fragmentation assays. To decrease cell viability is not necessary or desired for the treatment of blood disorders and may even be harmful. Surprisingly, many of the compositions of the invention maintain or, preferably, increase cell viability. This is a great benefit in the treatment of blood disorders and can significantly increase the chances for a successful outcome for the patient. For example, phenoxyacetic acid and butyric acid ethyl ester both reduce DNA fragmentation in fragmentation assays, and phenoxyacetic acid and $\alpha$-methyl cinnamic acid do not significantly alter system A transport of amino acids.

Another embodiment of the invention is directed to methods for the treatment of a subject with an infection or a neoplastic disorder by administering to the subject a composition comprising at least one or any combination of ambroxol, benserazide, desloratadine, resveratrol, NSC-95397, idarubicin, MS-275, or auronafin, in particular benserazide, desloratadine or MS-275 as disclosed herein. Treatable infectious diseases include bacterial infections such as sepsis and pneumonia, infections caused by bacterial pathogens such as, for example, Pneumococci, Streptococci, Staphylococci, Neisseria, Chlamydia, Mycobacteria, Actinomycetes and the enteric microorganisms such as enteric Bacilli; viral infections caused by, for example, a hepatitis virus, a retrovirus such as HIV, an influenza virus, a papilloma virus, a herpes virus (HSV I, HSV II, EBV), a polyoma virus, a slow virus, paramyxovirus and corona virus; parasitic diseases such as, for example, malaria, trypanosomiasis, leishmania, amebiasis, toxoplasmosis, sarcocystis, pneumocystis, schistosomiasis and elephantitis; and fungal infections such as candidiasis, phaeohyphomycosis, aspergillosis, mucormycosis, cryptococcosis, blastomycosis, paracoccidiodomycosis, coccidioidomycosis, histomycosis, actinomycosis, nocardiosis and the Dematiaceous fungal infections.

Anti-neoplastic activity includes, for example, the ability to induce the differentiation of transformed cells including cells which comprise leukemias, lymphomas, sarcomas, neural cell tumors, carcinomas including the squamous cell carcinomas, seminomas, melanomas, neuroblastomas, mixed cell tumors, germ cell tumors, undifferentiated tumors, neoplasm due to infection (e.g. viral infections such as a human papilloma virus, herpes viruses including Herpes Simplex virus type I or II or Epstein-Barr virus, a hepatitis virus, a human T cell leukemia virus (HTLV) or another retrovirus) and other malignancies. Upon differentiation, these cells lose their aggressive nature, no longer metastasize, are no longer proliferating and eventually die and/or are removed by the T cells, natural killer cells and macrophages of the patient's immune system. The process of cellular differentiation is stimulated or turned on by, for example, the stimulation and/or inhibition of gene specific transcription. Certain gene products are directly involved in cellular differentiation and can transform an actively dividing cell into a cell which has lost or has a decreased ability to proliferate. An associated change of the pattern of cellular gene expression can be observed. To control this process includes the ability to reverse a malignancy. Genes whose transcriptional regulation are altered in the presence of compositions of the invention include the oncogenes myc, ras, myb, jun, abl and src. The activities of these gene products as well as the activities of other oncogenes are described in J. D. Slamon et al. (Science 224:256-62, 1984).

Another example of anti-neoplastic activity includes the ability to regulate the life cycle of the cell, the ability to repress angiogenesis or tissue regeneration through the blockade or suppression of factor activity, production or release, the ability to regulate transcription or translation, or the ability to modulate transcription of genes under angiogenesis, growth factor or hormonal control. These activities are an effective therapy particularly against prostatic neoplasia and breast carcinomas. Additional anti-neoplastic activities include the ability to regulate the cell cycle for example by effecting time in and passage through S phase, M phase, $G_1$ phase or $G_0$ phase, the ability to increase intracellular cAMP levels, the ability to inhibit or stimulate histone acetylation, the ability to methylate nucleic acids and the ability to maintain or increase intracellular concentrations of anti-neoplastic agents.

The neoplastic disorder may be any disease or malady which could be characterized as a neoplasm, a tumor, a malignancy, a cancer or a disease which results in a relatively autonomous growth of cells. Neoplastic disorders prophylactically or therapeutically treatable with compositions of the invention include small cell lung cancers and other lung cancers, rhabdomyosarcomas, chorio carcinomas, glioblastoma multiformas (brain tumors), bowel and gastric carcinomas, leukemias, ovarian cancers, prostate cancers, osteosarcomas or cancers which have metastasized. Diseases of the immune system which are treatable by these compositions include the non-Hodgkin's lymphomas including the follicular lymphomas, Burkitt's lymphoma, adult T-cell leukemias and lymphomas, hairy-cell leukemia, acute myelogenous, lymphoblastic or other leukemias, chronic myelogenous leukemia, and myelodysplastic syndromes. Additional diseases treatable by the compositions include virally-induced cancers wherein the viral agent is EBV, HPV, HTLV-1 or HBV, breast cell carcinomas, melanomas and hematologic melanomas, ovarian cancers, pancreatic cancers, liver cancers, stomach cancers, colon cancers, bone cancers, squamous cell carcinomas, neurofibromas, testicular cell carcinomas and adenocarcinomas.

In some embodiments, composition comprising at least one or any combination of ambroxol, benserazide, desloratadine, resveratrol, NSC-95397, idarubicin, MS-275, or auronafin, in particular benserazide, desloratadine or MS-275 as disclosed herein cab be used in combination with other anti-neoplastic agents or therapies to maximize the effect of the compositions in an additive or synergistic manner. Cytokines which may be effective in combination with the compositions of the invention include growth factors such as B cell growth factor (BCGF), fibroblast-derived growth factor (FDGF), granulocyte/macrophage colony stimulating factor (GM-CSF), granulocyte colony stimulating factor (G-CSF), macrophage colony stimulating factor (M-CSF), epidermal growth factor (EGF), platelet derived growth factor (PDGF) nerve growth factor (NGF), stem cell factor (SCF), and transforming growth factor (TGF). These growth factors plus a composition may further stimulate cellular differentiation and/or the expression of certain MHC antigens or tumor specific antigens. For example, BCGF plus a composition may be effective in treating certain B cell leukemias. NGF plus a composition may be useful in treating certain neuroblastomas and/or nerve cell tumors. In a similar fashion, other agents such as differentiating agents may be useful in combination with a composition of the invention to prevent or treat a neoplastic disorder. Other differentiating agents include B cell differentiating factor (BCDF), erythropoietin (EPO), steel factor, activin, inhibin, the bone morphogenic proteins (BMPs), retinoic acid or retinoic acid derivatives such as retinol, the prostaglandins, and TPA.

Alternatively, other cytokines and related antigens in combination with a composition may also be useful to treat or prevent neoplasia. Potentially useful cytokines include tumor necrosis factor (TNF), the interleukins (IL-1, IL-2, IL-3, etc.), the interferon proteins (IFN) IFN-.alpha., IFN-.beta., and IFN-.gamma., cyclic AMP including dibutyryl cyclic AMP, hemin, hydroxyurea, hypoxanthine, glucocorticoid hormones, dimethyl sulfoxide (DMSO), and cytosine arabinoside, and anti-virals such as acyclovir and gemciclovirs. Therapies using combinations of these agents would be safe and effective against malignancies and other forms of cancer. Combinations of therapies may also be effective in inducing regression or elimination of a tumor or some other form of cancer such as compositions of the invention plus radiation therapy, toxin or drug conjugated antibody therapy using monoclonal or polyclonal antibodies directed against the transformed cells, gene therapy or specific anti-sense therapy. Effects may be additive, logarithmic, or synergistic, and methods involving combinations of therapies may be simultaneous protocols, intermittent protocols or protocols which are empirically determined Another embodiment of the invention comprises use of the composition comprising at least one or any combination of ambroxol, benserazide, desloratadine, resveratrol, NSC-95397, idarubicin, MS-275, or auronafin, in particular benserazide, desloratadine or MS-275 as disclosed herein and methods for the treatment of neoplastic disorders by augmenting conventional chemo-therapy, radiation therapy, antibody therapy, and other forms of therapy. Compositions containing chemical compounds of the invention, in combination with chemotherapeutic agents, enhance the effect of the chemotherapeutic agent alone. Compositions decrease the expression or activity of proteins responsible for lowering the intra-cellular concentration of chemotherapeutic agents. Proteins responsible for resistance to drugs and other agents, the multi-drug resistance (MDR) proteins, include the P-glycoprotein (Pgp) encoded by the mdr-1 gene. Consequently, conventional drugs for the treatment of neoplastic disorders accumulate at higher concentrations for longer periods of time and are more effective when used in combination with the compositions herein. Some conventional chemotherapeutic agents which would be useful in combination therapy with compositions of the invention include the cyclophosphamide such as alkylating agents, the purine and pyrimidine analogs such as mercapto-purine, the vinca and vinca-like alkaloids, the etoposides or etoposide like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as antiinsulin and antiandrogen, the antiestrogens such as tamoxifen an other agents such as doxorubicin, L-asparaginase, dacarbazine (DTIC), amsacrine (mAMSA), procarbazine, hexamethylmelamine, and mitoxantrone. The chemotherapeutic agent could be given simultaneously with the compounds of the invention or alternately as defined by a protocol designed to maximize drug effectiveness, but minimize toxicity to the patient's body.

Another embodiment of the invention is directed to aids for the treatment of human disorders such as infections, neoplastic disorders and blood disorders. Aids contain compositions of the invention in predetermined amounts which can be individualized in concentration or dose for a particular patient. Compositions, which may be liquids or solids, are placed into reservoirs or temporary storage areas within the aid. At predetermined intervals, a set amount of one or more compositions are administered to the patient. Compositions to be injected may be administered through, for example, mediports or in-dwelling catheters. Aids may further comprise mechanical controls or electrical controls devices, such as a programmable computer or computer chip, to regulate the quantity or frequency of administration to patients. Examples include the Baxa Dual Rate Infuser (Baxa Corp.; Englewood, Colo.) and the Baxa Programmable Infuser (Baxa Corp.; Englewood, Colo.). Delivery of the composition may also be continuous for a set period of time. Aids may be fixed or portable, allowing the subject as much freedom as possible.

Treatment Options

The average U.S. survival of patients with beta thalassemia and SCD is approximately 26 years and 40 years of age, respectively.

In beta thalassemia intermedia (TI) and SCD, most affected individuals can sustain activities of daily living when provided with appropriate supportive care, such as transfusions at times of illness (e.g. infection) or pregnancy. Transfusions are required more frequently over time, as the conditions progress to more severe, later stage disease. Many patients develop iron overload as a complication of multiple transfusions and other transfusion-related complications such as those described above. Frequent transfusions in areas of the world with suboptimal blood product screening also place such patients at risk for potential blood-borne pathogens. Cirrhosis from hepatitis C is common in patients in many parts of the world. With transfusion therapy, many patients become alloimmunized which increases the risk of hypersensitivity reactions and transfusion requirements due to progressively reduced RBC survival.

The Role of Fetal Hemoglobin

Genotypic variations in healthy individuals have been identified wherein adult beta globin is not formed, but severe complications are avoided. In certain instances, these patients express fetal globin in amounts sufficient to substitute for the missing beta globin chains. In some instances, this hereditary persistence of fetal hemoglobin involves one or both of the fetal globin genes. In certain instances, consistent production of fetal globin accomplishes the necessary functions of abnormal or missing beta globin chains.

The level of fetal hemoglobin (HbF) expression is one of the most important modifiers of disease expression for patients with SCD. The percentage of HbF (% HbF) influences both laboratory values and clinical features of children and adults with SCD. In one instance, 30% HbF in every red blood cell is a highly effective inhibitor of clinical sickling, while 15% to 22% HbF in 60% to 70% of cells is beneficial to Saudi Arabian and Indian patients. In further instances, elevated % HbF has been significantly associated with fewer painful vaso-occlusive events, fewer episodes of acute chest syndrome, and reduced early mortality. Increased HbF levels correlate with reduction in organ damage and improved patient survival.

Higher production of HbF parallels higher hemoglobin levels in beta thalassemia patients, similar to findings in sickle cell disease. In certain instances, patients with beta thalassemia treated with hydroxyurea had an increase in HbF levels and an apparent decrease in crisis frequencies. For instance, the two major hemoglobin components in patients with HbE beta thalassemia disease are HbE and HbF, the levels of HbF varying from 30% to 70%. In some instances, there is a good correlation of hemoglobin levels with the amount of HbF production in certain groups of patients with HbE beta thalassemia disease. Increased HbF production associated with an improvement in the alpha/non-alpha globin production can be achieved using hydroxyurea. In some instances, the temporal relationship between the increase in % HbF (and the reciprocal decrease in % HbE) and the increase in total hemoglobin is consistent with improved erythropoiesis. For example, in a study almost all HbE beta thalassemia patients treated with hydroxyurea responded with an increase in HbF levels and a reciprocal decline in % HbE, reticulocytosis was decreased, and there was a slight but statistically significant increase in hemoglobin levels and an improved balance in alpha/non-alpha globin chain ratios.

In certain instances, reactivating fetal globin to approximately 60-70% of β-globin chain synthesis ameliorates anemia in beta thalassemia enough to eliminate transfusion requirements. Chemotherapeutic agents (hydroxyurea and 5-azacytidine or decitabine), short chain fatty acid derivatives (SCFADs), and rhu-erythropoietin (EPO) are being evaluated in clinical trials, with highest hematologic responses observed in patients with baseline (untransfused) HbF levels >50% and erythropoietin levels >130 mU/mL. In some instances, combinations of these agents are required to eliminate regular transfusion requirements in severe β thalassemia patients. Non-mutagenic, non-cytotoxic agents are preferable over chemotherapy for life-long treatment. Sodium phenylbutyrate (Buphenyl) and arginine butyrate have increased total hemoglobin by 1-4 g/dL above baseline in untransfused patients, but require large numbers of tablets or IV infusion, respectively. Patients with β+ thalassemia and baseline EPO levels <80 mU/ml have responded best to combined therapy with butyrate and EPO. The long-acting EPO preparation, darbepoietin, increases hemoglobin in some. These therapies require supplementation with oral iron to be effective, even in the presence of elevated ferritin levels, as stored iron may not be available for erythropoiesis, and several months of treatment are often required. New oral short chain fatty acid derivatives under evaluation appear more tolerable Doses and Administration:

In some embodiments, the dose of an HbF inducer as disclosed herein can be assessed in vitro in a panel of erythroid progenitors cultured from peripheral blood of beta-thalassemia patients, to evaluate comparative HbF induction in the 2 major subtypes of beta-thalassemia. Additionally, the dose of an HbF inducer can be assessed and determined in an in vivo non-human primate model as disclosed in the Examples. Furthermore, clinical studies assessing the long-term safety profile of an HbF inducer as disclosed herein can be performed, e.g., for example, by selecting patients with α- or beta-thalassemia intermedia, 2 subtypes, comparing 2 doses of a HbF inducer agent as disclosed herein, which is administered weekly or bi-weekly dose regimen for a predetermined period of time, e.g., approximately 3 months. During the study, the blood counts of the patients can be monitored every 2 weeks, or every 4 weeks, and determining one or more of: (1) change from baseline in HbF expression and total Hb as compared to baseline levels, and/or (2) safety and tolerability of administration of the HbF inducer agent in the patient population. Secondary endpoints can also be assessed, for example, change in laboratory biomarkers of hemolysis (LDH).

In some embodiments, the amount of a HbF-inducing agent that can be combined with a carrier material to produce a single dosage form will generally be that amount of the compound that produces a therapeutic effect. Generally out of one hundred percent, this amount will range from about 0.01% to 99% of the compound, preferably from about 5% to about 70%, most preferably from 10% to about 30%.

The data obtained from the cell culture assays and animal studies can be used in formulating a range of dosage for use in humans. The dosage of such compounds lies preferably within a range of circulating concentrations that include the ED50 (the dose therapeutically effective in 50% of the population) with little or no toxicity. The dosage may vary within this range depending upon the dosage form employed and the route of administration utilized.

The therapeutically effective dose of a HbF-inducing agent can be estimated initially from cell culture assays, for example, one can measure the % increase in mRNA γ-globin in the blood on administration, as disclosed herein. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage of a HbF-inducing agent may be determined by a physician and adjusted, as necessary, to suit observed effects of the treatment. Generally, the compositions are administered so that a HbF-inducing agent or a prodrug thereof is given at a dose from 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions comprising a HbF-inducing agent are administered at a dosage so that a HbF-inducing agent or a metabolite thereof has an in vivo, e.g., serum or blood, concentration of less than 500 nM, less than 400 nM, less than 300 nM, less than 250 nM, less than 200 nM, less than 150 nM, less than 100 nM, less than 50 nM, less than 25 nM, less than 20 nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to a HbF-inducing agent acid. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, pulsed administration of a HbF-inducing agent as disclosed herein is more effective than continuous treatment because total pulsed doses are often lower than would be expected from continuous administration of the same composition. Each pulse dose can be reduced and the total amount of drug administered over the course of treatment is minimized In traditional forms of therapy, repeated administration is designed to maintain a desired level of an active ingredient in the body. Very often, complications that develop can be attributed to dosage levels that, to be effective, are near toxic or otherwise harmful to normal cells. In contrast, with pulse therapy, in vivo levels of drug drop below that level required for effective continuous treatment. Therefore, pulsing is not simply the administration of a sufficiently large bolus such that there will be therapeutically sufficient drug available for a long period of time. Pulsed administration can substantially reduce the amount of the composition administered to the patient per dose or per total treatment regimen with an increased effectiveness. This represents a significant saving in time, effort and expense and, more importantly, a lower effective dose substantially lessens the number and severity of complications that may be experienced by the patients.

Individual pulses of a HbF-inducing agent as disclosed herein can be delivered to the patient continuously over a period of several hours, such as about 2, 4, 6, 8, 10, 12, 14 or 16 hours, or several days, such as 2, 3, 4, 5, 6, or 7 days, preferably from about 1 hour to about 24 hours and more preferably from about 3 hours to about 9 hours. Alternatively, periodic doses can be administered in a single bolus or a small number of injections of the composition over a short period of time, typically less than 1 or 2 hours. For example, arginine butyrate has been administered over a period of 4 days with infusions for about 8 hours per day or overnight, followed by a period of 7 days of no treatment. This has been shown to be an effective regimen for many thalassemic disorders. Fetal hemoglobin levels rise substantially and there is a significant rise in the number of both adult and fetal hemoglobin expressing cells. In certain instances, a substantial rise in HbF means that there are positive consequences that raise the patient's standard of living such as, for example, increased activity or mobility, fewer side-effects, fewer hospital stays or visits to the physician, or fewer transfusions. For instance, HbF levels above 20% are generally considered to be sufficient to eliminate symptoms associated with sickle cell disease.

The interval between pulses or the interval of no delivery is greater than 24 hours and preferably greater than 48 hours, and can be for even longer such as for 3, 4, 5, 6, 7, 8, 9 or 10 days, two, three or four weeks or even longer. Often, the interval between pulses can be calculated by administering another dose of the composition when the composition or the active component of the composition is no longer detectable in the patient prior to delivery of the next pulse. Intervals can also be calculated from the in vivo half-life of the composition. Intervals may be calculated as greater than the in vivo half-life, or 2, 3, 4, 5 and even 10 times greater the composition half-life. For compositions with fairly rapid half lives, intervals may be 25, 50, 100, 150, 200, 250 300 and even 500 times the half life of the chemical composition. The number of pulses in a single therapeutic regimen may be as little as two, but is typically from about 5 to 10, 10 to 20, 15 to 30 or more. In some embodiments, patients receive drugs for life according to the methods of this invention without the problems and inconveniences associated with current therapies.

In certain embodiments, compositions comprising a HbF-inducing agent as disclosed herein are administered by most any means, but are preferable delivered to the patient as an injection (e.g. intravenous, subcutaneous, intraarterial), infusion or instillation, and more preferably by oral ingestion.

In some embodiments, administration of a composition comprising a HbF-inducing agent and/or salts can be intermittent; for example, administration can be once every two days, every three days, every five days, once a week, once or twice a month, and the like. The amount, forms, and/or amounts of the different forms of a composition comprising a HbF-inducing agent can be varied at different times of administration.

Pulsed administration of one or more pharmaceutical compositions comprising a HbF-inducing agent can be used for the treatment of a blood disorder in a subject, e.g., but not limited to hemaglobinaphthy, thalassemia and aplastic anemia. In some embodiments, pulsed administration of one or more pharmaceutical compositions comprising S a HbF-inducing agent can be used to stimulate myelopiesis or erythropoiesis in a subject, or to increase the proliferation of hematopoietic cells, such as hemoglobin expressing cells and red blood cells, white blood cells, neutrophils and the like. Similarly, pulsed administration of one or more pharmaceutical compositions comprising a HbF-inducing agent can be used for prophylactic treatment, e.g., for example, a subject who will, or has or is currently undergoing chemotherapy and chemoradiation therapy. In some embodiments, pulsed administration can be more effective than continuous treatment as pulsed doses results in an overall lower amount of compound used than would be expected from continuous administration of the same composition. Each pulse dose can be reduced and the total amount of drug administered over the course of treatment to the patient can be minimized With pulse therapy, in vivo levels of a HbF-inducing agent thereof can drop below that level required for effective continuous treatment. Pulsed administration can reduce the amount of a composition comprising a HbF-inducing agent thereof administered to the patient per dose, and/or per total treatment regimen with an increased effectiveness. Pulsed administration can provide a saving in time, effort and expense and a lower effective dose can lessen the number and severity of complications that can be experienced by a subject. As such, pulsing can be more effective than continuous administration of the same composition.

In some embodiments, individual pulses can be delivered to a subject continuously over a period of several hours, such as about 2, 4, 6, 8, 10, 12, 14 or 16 hours, or several days, such as 2, 3, 4, 5, 6, or 7 days, or from about 1 hour to about 24 hours or from about 3 hours to about 9 hours. Alternatively, periodic doses can be administered in a single bolus or a small number of injections of the composition comprising a HbF-inducing agent thereof over a short period of time, for example, less than 1 or 2 hours. For example, arginine butyrate can be administered over a period of 4 days with infusions for about 8 hours per day or overnight, followed by a period of 7 days of no treatment.

The interval between pulses or the interval of no delivery can be greater than 24 hours or can be greater than 48 hours, and can be for even longer such as for 3, 4, 5, 6, 7, 8, 9 or 10 days, two, three or four weeks or even longer. The interval between pulses can be determined by one of ordinary skill in the art, for example, as demonstrated herein in the Examples, by measuring the $\gamma$-globin expression level in the blood in the subject after administration of the pulse dose, and administering a pulse when the mRNA $\gamma$-globin level reaches a certain pre-defined low threshold limit. Such pre-defined low threshold limits can be determined by one of ordinary skill in the art, and can be, for example, about baseline level, or about 100% or about 200% above baseline level mRNA $\gamma$-globin expression (e.g, mRNA $\gamma$-globin expression without administration of a HbF-inducing agent) (see FIGS. 12A and 12B). Alternatively, in some embodiments, the interval between pulses can be calculated by administering another dose of a composition comprising a HbF-inducing agent, and when the active component of the composition is no longer detectable in the patient prior to delivery of the next pulse. Alternatively, intervals can also be calculated from the in vivo half-life of the composition.

The interval between pulses can also be determined by one of ordinary skill in the art, for example, as demonstrated herein in the Examples, by measuring the % increase in absolute hemoglobin (see FIG. 12B), % F-reticulocytes, % increase in F-cells, in the blood in the subject after administration of the pulse dose, and administering a pulse when the mRNA $\gamma$-globin level reaches a certain pre-defined low threshold limit, for example below about a 1.0 or about 0.5% increase in absolute hemoglobin.

In some embodiments, the number of pulses in a single therapeutic regimen can be as little as two, but can be from about 5 to 10, 10 to 20, 15 to 30 or more.

In some embodiments, a subject can receive one or more compositions comprising a HbF-inducing agent for life according to the methods of this invention, for example, where the subject has a permanent or incurable blood disorder, e.g., an inherited blood disorder. Compositions can be administered by most any means, and can be delivered to the subject as an oral formulation, or injection (e.g. intravenous, subcutaneous, intraarterial), infusion or instillation. Various methods and apparatus for pulsing compositions by infusion or other forms of delivery to the patient are disclosed in U.S. Pat. Nos. 4,747,825; 4,723,958; 4,948,592; 4,965,251 and 5,403,590, which are incorporated herein in their entirety by reference.

In one embodiment, a composition comprising a HbF-inducing agent thereof can be administered to a subject for about 2, or about 3, or about 4, or about five days, or more than five days, and then a subsequently administered after an appropriate interval for an additional period of time, for example, for about 2, or about 3, or about 4, or about five days, or more than five days. Cycles of treatment may occur in immediate succession or with an interval of no treatment between cycles.

In some embodiments, a composition comprising a HbF-inducing agent can be administered to a subject before a chemotherapeutic treatment, or radiation treatment is administered to the subject. In alternative embodiments, a composition comprising a HbF-inducing agent can be co-administered to a subject concurrently with another agent or treatment regimen, e.g., concurrently with a chemotherapeutic treatment, or radiation treatment. In some embodiments, a composition comprising a HbF-inducing agent can be co-administered with a pharmaceutical composition comprising an comprising one or more addition agents. The pharmaceutical compositions can be provided by pulsed administration. For example, a composition comprising a HbF-inducing agent can be administered to a subject, followed by a chemotherapeutic treatment, or radiation treatment after an interval of time has passed, and this order of administration the same or similar time interval can be repeated, for example, at least 1, 2, 3, 4, 5, 6, 7, 8, 9, or 10 or more times.

A HbF-inducing agent or a prodrug thereof can be administrated to a subject in combination with one or more pharmaceutically active agents. Exemplary pharmaceutically active compound include, but are not limited to other HDAC inhibitors, such as Arginine Butyrate and/or Phenylbutyrate, as well an BCl1 inhibitor, or other compounds as those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

Method for Increasing % HbF and/or Total Hemoglobin

Provided herein are methods for increasing the percentage of fetal hemoglobin in the blood of a subject, comprising administering to a subject a composition comprising a HbF-inducing agent as disclosed herein as the free acid, a pharmaceutically acceptable salt, or ester thereof.

Further provided herein are methods for increasing total hemoglobin in the blood of a subject, comprising administering to the subject a composition comprising a HbF-inducing agent as disclosed herein as the free acid, a pharmaceutically acceptable salt, or ester thereof. Also provided herein are methods for increasing total hemoglobin, hematocrit, and red blood cells in a subject, comprising administering to said subject a HbF-inducing agent as disclosed herein as the free acid, a pharmaceutically acceptable salt, or ester thereof. Further provided herein are methods for increasing total hemoglobin, hematocrit, or red blood cells, or a combination thereof, comprising administering to said subject a HbF-inducing agent as disclosed herein.

In some embodiments, administering a HbF-inducing agent as disclosed herein does not suppress erythropoiesis at concentrations associated with biologic activity. In certain embodiments, administering a HbF-inducing agent as disclosed herein stimulates cell proliferation. In some embodiments, administering a HbF-inducing agent as disclosed herein inhibits apoptosis of erythroid progenitors. In further embodiments, administering a HbF-inducing agent as disclosed herein stimulates erythroid cell proliferation and survival. In some embodiments, administering a HbF-inducing agent as disclosed herein stimulates erythroid cell proliferation. In certain embodiments, administering a HbF-inducing agent as disclosed herein stimulates erythroid cell survival. In some embodiments, administering a HbF-inducing agent as disclosed herein stimulates red blood cell production. In certain embodiments, administering a HbF-inducing agent as disclosed herein leads to a longer survival of sickled blood cells.

In some embodiments, administering a HbF-inducing agent as disclosed herein stimulates erythropoiesis. In certain embodiments, administering a HbF-inducing agent as disclosed herein induces expression of the fetal globin gene promoter. In some embodiments, administering a HbF-inducing agent as disclosed herein increases fetal globin levels. In certain embodiments, administering a HbF-inducing agent as disclosed herein increases RBC production. In some instances, increased RBC production is assayed by reticulocytes, total hemoglobin (Hgb), and hematocrit (Hct).

In certain embodiments, administering a HbF-inducing agent as disclosed herein increases the amount of fetal globin in the blood of the subject. In some embodiments, administering a HbF-inducing agent as disclosed herein increases the amount of fetal hemoglobin in the blood of the subject. In certain embodiments, administering a HbF-inducing agent as disclosed herein increases the amount of total hemoglobin in the blood of the subject. In some embodiments, administering a HbF-inducing agent as disclosed herein increases the percentage of reticulocytes in the blood of the subject. In certain embodiments, administering a HbF-inducing agent as disclosed herein increases the number of reticulocytes in the blood of the subject. In some embodiments, administering a HbF-inducing agent as disclosed herein increases hematocrit.

In contrast to ST20 or hydroxyurea, a HbF-inducing agent as disclosed herein is effective at increasing % HbF at a total daily dose which is below the maximum tolerated dose. In some instances, administering a HbF-inducing agent as disclosed herein does not necessitate the careful dose titration currently required for treatment with ST20.

In addition, the total daily dose of a HbF-inducing agent as disclosed herein which is effective in increasing the percentage of HbF is significantly lower than the dose required for other SCFAD like arginine butyrate. In some embodiments, a subject can be administered a HbF-inducing agent as disclosed herein with other agents, including but not limited to 2,2-dimethylbutyrate is administered as sodium 2,2-dimethylbutyrate. 2,2-Dimethylbutyrate includes, but is not limited to, 2,2-dimethylbutyric acid, sodium 2,2-dimethylbutyrate, potassium 2,2-dimethylbutyrate, magnesium 2,2-dimethylbutyrate, calcium 2,2-dimethylbutyrate, arginine 2,2-dimethylbutyrate, lysine 2,2-dimethylbutyrate, choline 2,2-dimethylbutyrate, methyl 2,2-dimethylbutyrate (2,2-dimethylbutyric acid methyl ester), ethyl 2,2-dimethylbutyrate, propyl 2,2-dimethylbutyrate, or isopropyl 2,2-dimethylbutyrate.

In certain embodiments, the subject has been diagnosed with a blood disorder. In some embodiments, the blood disorder is sickle cell disease. In other embodiments, the blood disorder is a α- and/or beta thalassemia. In certain embodiments, the beta thalassemia is beta thalassemia intermedia. In some embodiments, the beta thalassemia is beta thalassemia major. In certain embodiments, the beta thalassemia is beta thalassemia minor (beta thalassemia trait). In some embodiments, the beta thalassemia is HbE beta thalassemia. In certain embodiments, the beta thalassemia is HbS beta thalassemia.

In certain embodiments, a subject is administered a composition comprising a HbF-inducing agent as disclosed herein, daily. In further embodiments, administration is continuous. In some embodiments, the administration of a composition comprising a HbF-inducing agent as disclosed herein is by pulsed administration. In certain embodiments, pulsed administration comprises administering a HbF-inducing agent pulse for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In some embodiments, pulsed administration comprises intervals of not administering a HbF-inducing agent for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months. In certain embodiments, administration is for the lifetime of the subject.

In some embodiments, a composition comprising a HbF-inducing agent is administered every other day. In certain embodiments, the pulsed administration comprises administering a composition comprising a HbF-inducing agent for about 5 days per week. In some embodiments, the pulsed administration comprises administering a composition comprising a HbF-inducing agent for about 5 days, followed by not administering a HbF-inducing agent for about 2 days. In certain embodiments, the pulsed administration comprises administering a HbF-inducing agent for about 2 weeks, followed by not administering a HbF-inducing agent for about 1 week. In some embodiments, the pulsed administration comprises administering a HbF-inducing agent for about 2 weeks, followed by not administering a HbF-inducing agent for about 2 weeks. In certain embodiments, the pulsed administration comprises administering a HbF-inducing agent for about 4 weeks, followed by not administering a HbF-inducing agent for about 1 week. In some embodiments, the pulsed administration comprises administering a HbF-inducing agent for about 4 weeks, followed by not administering a HbF-inducing agent for about 2 weeks. In further embodiments, the pulsed administration comprises administering a HbF-inducing agent for about 6 weeks, followed by not administering a HbF-inducing agent for about 2 weeks. In certain embodiments, the pulsed administration comprises administering a HbF-inducing agent for about 8 weeks, followed by not administering a HbF-inducing agent for about 2 weeks. In some embodiments, the pulsed administration comprises administering a HbF-inducing agent for about 8 weeks, followed by not administering a HbF-inducing agent for about 4 weeks.

In some instances, administering a composition comprising a HbF-inducing agent to a subject with one genotype of beta thalassemia is more effective in raising % HbF than administering DMB to a subject with a different genotype of beta thalassemia. Further provided herein are methods comprising diagnosing a beta thalassemia genotype of a patient, determining a treatment plan considering the beta thalassemia genotype, and optionally increasing the percentage of fetal hemoglobin in the blood of the patient, comprising administering to the patient a HbF-inducing agent as the free acid, a pharmaceutically acceptable salt, or ester thereof.

Pharmaceutical Compositions

In some embodiments, a pharmaceutical composition comprising a HbF-inducing agent administered according to a method of the invention are administered orally in effective dosages, depending upon the weight, body surface area, and condition of the subject being treated. In some instances, variations occur depending upon the species of the subject being treated and its individual response to said medicament, as well as on the type of pharmaceutical formulation chosen and the time period and interval at which such administration is carried out.

In some embodiments, the administration of the pharmaceutical composition comprising a HbF-inducing agent according to a method of the invention is carried out in single or multiple doses. For example, the composition can be administered in a wide variety of different dosage forms, i.e., it may be combined with various pharmaceutically acceptable inert carriers in the form of tablets, dragees, capsules, lozenges, troches, hard candies, aqueous suspensions, elixirs, syrups, and the like. Such carriers include solid diluents or fillers, sterile aqueous media and various non-toxic organic solvents, etc. Moreover, oral pharmaceutical compositions can be suitably sweetened and/or flavored.

In certain embodiments, pharmaceutical compositions comprising a HbF-inducing agent are suitable for oral administration. Suitable pharmaceutical compositions for oral administration can be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient. When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: filters or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

If desired, pharmaceutical compositions of the present invention may also be formulated to provide slow or controlled release of the active ingredient using, by way of example, hydroxypropyl methyl cellulose in varying proportions; or other polymer matrices, liposomes and/or microspheres. Sustained release compositions can be formulated including those wherein the active component is derivatized with differentially degradable coatings, e.g., by microencapsulation, multiple coatings, etc.

It will be appreciated that the actual preferred amounts of active compounds used in a given therapy will vary according to the particular compositions formulated. Optimal administration rates for a given protocol of administration can be readily ascertained by those skilled in the art using conventional dosage determination tests conducted with regard to the foregoing guidelines.

It will also be understood that normal, conventionally known precautions will be taken regarding the administration of the compounds of the invention generally to ensure their efficacy under normal use circumstances. Especially when employed for treatment of humans and animals in vivo, the practitioner should take all sensible precautions to avoid conventionally known contradictions and toxic effects.

The composition, shape, and type of dosage forms of the invention will typically vary depending on their use. This aspect of the invention will be readily apparent to those skilled in the art. See, e.g., Remington's Pharmaceutical Sciences (1990) 18th ed., Mack Publishing, Eastern Pa.

In certain embodiments, the pharmaceutical compositions of the invention is packaged in a unit dosage form. The term "unit dosage form" or "unit dose" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like. Unit doses can also be prepared to contain any useful amount of an active ingredient (e.g., a HbF-inducing agent). For example, a unit dose can comprise 10 mg, 20mg, 30mg, 40mg, 50mg, 60mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg, 625 mg, 650 mg, 675 mg, 700 mg, 750 mg, 800 mg, 850 mg, 900 mg, 950 mg, 1000 mg, or more of a HbF-inducing agent per unit dose. Milligrams per dose can refer to either the free acid form of a HbF-inducing agent, or a HbF-inducing agent in a salt or ester form.

Administrations can be repeated on consecutive or non-consecutive days. Thus, daily administrations can be performed for 2, 3, 4, 5, 6, 7, 8, 9, 10, 11, 12, 13, 14, 15, 16, 17, 18, 19, 20, 25, 30, 35, 40, 45, 50, 55, 60, or more consecutive days. For example, administration of 10 mg/kg of a HbF-inducing agent is performed twice a day (at a total daily dose of 20 mg/kg) for 14 consecutive days. Alternatively, administration may occur for multiple days, but on non-consecutive days separated by 1, 2, 3, 4, 5, 6, 7, 8, 9, 10 or more days. For example, administration of 15 mg/kg of a HbF-inducing agent is performed on every other day following therapy onset. In another instance, administration of a HbF-inducing agent is performed for 5 days per week. Such dosing regimens can be tailored to an individual patient, based on any number of clinically relevant parameters including, but not limited to toxicity, tolerance, side-effects, effectiveness, etc.

Combination Therapy

In certain embodiments, the pharmaceutical composition is administered alone or in combination with other known compositions for treating blood disorders in a subject, e.g., a mammal. In some embodiments, mammals include cats, dogs, pigs, horses, cows, rats, mice, monkeys, chimpanzees, baboons, and humans. In specific embodiments, the mammal is a human. In some embodiments, the human is a child. In certain embodiments, the human is under the age of 18. In some embodiments, the human is under the age of 10. In some embodiments, the human is under the age of 2. In one embodiment, the subject is suffering from a blood disorder. In another embodiment, the subject is at risk of suffering from a blood disorder.

The language "in combination with" a known composition is intended to include simultaneous administration of the composition of the invention and the known composition, administration of the composition of the invention first, followed by the known composition and administration of the known composition first, followed by the composition of the invention. Any of the compositions known in the art for treating blood disorders can be used in the methods of the invention.

In some embodiments, in addition to the use of a HbF-inducing agent for the treatment of blood disorders, concomitant administration of other pharmaceutical and nutraceutical compounds occurs. For example, persons suffering from sickle cell disease are given a HbF-inducing agent other agents as disclosed herein), folic acid supplements (for blood cell production), opioids or analgesics (for pain management), and/or antibiotics (for treating secondary infections). In further embodiments, administration of a HbF-inducing agent for the treatment of blood disorders is combined with the administration of natural or synthetic erythropoietin. In certain instances, concomitant treatment with a HbF-inducing agent and a second agent occurs at the same time, or on different regimen schedules. In some embodiments a HbF-inducing agent is an orally bio-available compound that is active at well tolerated doses.

Administration of the compositions comprising HbF-inducing agents as described herein may be by oral, parenteral, sublingual, rectal, or enteral administration, or pulmonary absorption or topical application. Compositions can be directly or indirectly administered to the patient. Indirect administration is performed, for example, by administering the composition to cells ex vivo and subsequently introducing the treated cells to the subject, e.g., human patient. Alternatively, the cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

The compositions comprising HbF-inducing agents can be purchased commercially and prepared as a mixed composition using techniques well-known to those of ordinary skill in the art.

Direct administration of a composition comprising HbF-inducing agents to a subject can be by oral, parenteral, sublingual, rectal such as suppository or enteral administration, or by pulmonary absorption or topical application. Parenteral administration may be by intravenous (IV) injection, subcutaneous (s.c.) injection, intramuscular (i.m) injection, intra-arterial injection, intrathecal (i.t.) injection, intra-peritoneal (i.p) injection, or direct injection or other administration to the subject.

Alternatively, pharmaceutical compositions comprising HbF-inducing agents and/or salts thereof can be added to the culture medium of cells ex vivo. In addition to the active compound, such compositions comprising HbF-inducing agents can contain pharmaceutically-acceptable carriers and other ingredients known to facilitate administration and/or enhance uptake (e.g., saline, dimethyl sulfoxide, lipid, polymer, affinity-based cell specific-targeting systems). In some embodiments, a composition comprising HbF-inducing agents and/or salts thereof can be incorporated in a gel, sponge, or other permeable matrix (e.g., formed as pellets or a disk) and placed in proximity to the endothelium for sustained, local release. In some embodiments, a composition comprising HbF-inducing agents and/or salts thereof can be administered in a single dose or in multiple doses which are administered at different times.

Pharmaceutical compositions comprising HbF-inducing agents and/or salts thereof can be administered by any known route. By way of example, a composition c comprising HbF-inducing agents and/or salts thereof can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

Suitable choices in amounts and timing of doses, formulation, and routes of administration of a composition comprising HbF-inducing agents and/or salts thereof can be made with the goals of achieving a favorable response in the subject with a blood disorder, e.g., thalassemia, aplastic anemia and hemaglobinaphthy or a risk of developing neutropenia or cytopenia, and avoiding undue toxicity or other harm thereto (i.e., safety). Therefore, "effective" refers to such choices that involve routine manipulation of conditions to achieve a desired effect.

A bolus of the formulation of a composition comprising HbF-inducing agents and/or salts thereof administered to an individual over a short time once a day is a convenient dosing schedule. Alternatively, the effective daily dose can be divided into multiple doses for purposes of administration, for example, two to twelve doses per day. Dosage levels of active ingredients in a pharmaceutical composition comprising HbF-inducing agents and/or salts thereof can also be varied so as to achieve a transient or sustained concentration of the compound or derivative thereof in an individual, especially in and around the blood circulation and to result in the desired therapeutic response or protection. But it is also within the skill of the art to start doses at levels lower than required to achieve the desired therapeutic effect and to gradually increase the dosage until the desired effect is achieved.

In some embodiments, the amount of a composition comprising HbF-inducing agents and/or salts thereof can be administered is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration, and the like. It will also be understood that the specific dose level to be achieved for any particular individual can depend on a variety of factors, including age, gender, health, medical history, weight, combination with one or more other drugs, and severity of disease.

Production of compounds comprising HbF-inducing agents and/or salts thereof according to present regulations will be regulated for good laboratory practices (GLP) and good manufacturing practices (GMP) by governmental agencies (e.g., U.S. Food and Drug Administration). This requires accurate and complete record keeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

Dosages, formulations, dosage volumes, regimens, and methods for analyzing results aimed at increasing the proliferation of blood cells, and increasing absolute neutrophil count (ANC) can vary. Thus, minimum and maximum effective dosages vary depending on the method of administration. Increase in ANC in a subject can occur within a specific dosage range, which varies depending on, for example, the race, sex, gender, age, and overall health of the subject receiving the dosage, the route of administration, whether a composition comprising HbF-inducing agents and/or salts thereof is administered in conjunction with other molecules, and the specific regimen of administration of the composition comprising HbF-inducing agents and/or salts thereof. For example, in general, nasal administration requires a smaller dosage than oral, enteral, rectal, or vaginal administration.

In an alternative embodiment, for oral and/or enteral formulations of a composition comprising HbF-inducing agents and/or salts thereof, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982, which are all incorporated herein in their entirety by reference.

Examples of solid carriers include starch, sugar, bentonite, silica, and other commonly used carriers. Further non-limiting examples of carriers and diluents which can be used in the formulations of the present invention include saline, syrup, dextrose, and water.

Enteric Coated Formulation

In some embodiments, oral formulations of a composition comprising HbF-inducing agents and/or salts thereof can be in the form of a tablet formulation, for example, comprising HbF-inducing agents and/or salts thereof with an enteric polymer casing. An example of such a preparation can be found in WO2005/021002, which is incorporated herein in its entirety by reference. The active material in the core can be present in a micronised or solubilised form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof binders such as microcrystalline cellulose, hydroxypropylmethylcellulose, hydroxypropyl-cellulose, polyvinylpyrrolidone, pre-gelatinised starch or gum acacia or mixtures thereof disintegrants such as microcrystalline cellulose (fulfilling both binder and disintegrant functions) cross-linked polyvinylpyrrolidone, sodium starch glycollate, croscarmellose sodium or mixtures thereof lubricants, such as magnesium stearate or stearic acid, glidants or flow aids, such as colloidal silica, talc or starch, and stabilizers such as desiccating amorphous silica, coloring agents, flavors etc. In some embodiments, a tablet comprises lactose as diluent. When a binder is present, it is preferably hydroxypropylmethyl cellulose. In some embodiments, a tablet comprises magnesium stearate as lubricant. In some embodiments, a tablet comprises croscarmellose sodium as disintegrant, or can comprises a microcrystalline cellulose.

In some embodiments, a diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

In some embodiments, the active ingredient, e.g., HbF-inducing agents and/or a salts thereof comprises between 10 and 50% of the weight of the core, more preferably between 15 and 35% of the weight of the core. (calculated as free base equivalent). The core can contain any therapeutically suitable dosage level of the active ingredient e.g., HbF-inducing agents and/or a salts thereof, but preferably contains up to 150 mg as free base of the active ingredient. In some embodiments, the core contains 20, 30, 40, 50, 60, 80 or 100 mg as free base of the active ingredient. The active ingredient e.g., HbF-inducing agents and/or a salts thereof can be present as the free base, or as any pharmaceutically acceptable salt. If the active ingredient e.g., HbF-inducing agents is present as a salt, the weight is adjusted such that the tablet contains the desired amount of active ingredient, calculated as free base of the salt. In some embodiments, the active ingredient e.g., HbF-inducing agents is present as a hydrochloride salt.

In some embodiments, the core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

In some embodiments, the core can be surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin or 1,2-, 3,4-diepoxybutane. The casing can also include starch and/or dextrin.

In some embodiments, an enteric coating materials are the commercially available EUDRAGIT® enteric polymers such as EUDRAGIT® L, EUDRAGIT® S and EUDRAGIT® NE, used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or CITROFLEX® or CITROFLEX® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

In some embodiments, a casing can also include an anti-tack agent such as talc, silica or glyceryl monostearate. In some embodiments, an anti-tack agent is glyceryl monostearate. Typically, the casing can include around 5-25 wt % Plasticiser and up to around 50 wt % of anti tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an OPADRY coating, and particularly preferably it is Opadry White OY-S-28876.

In one embodiment, the pharmaceutically active ingredient is HbF-inducing agents or a salt thereof.

In some embodiments, an example of an enteric-coated formulation as described in WO2005/021002, comprises varying amounts of HbF-inducing agents. In that example, lactose monohydrate, microcrystalline cellulose, the active ingredient, the hydroxypropyl methyl cellulose and half of the croscarmellose sodium were screened into a 10 Liter Fielder high-shear blender (any suitable high shear blender could be used) and blended for 5 minutes at 300 rpm with the chopper off. The mixture was then granulated by the addition of about 750 ml water whilst continuing to blend. The granules were dried in a Glatt 3/5 fluid bed drier, screened by Comil into a Pharmatec 5 Liter bin blender and then blended with any lactose anhydrous given in the formula plus the remainder of the croscarmellose sodium over 5 minutes at 20 rpm. Magnesium stearate was screened into the blender and the mixing process continued for a further 1 minute at 10 rpm. The lubricated mix was compressed using a Riva Piccolla rotary tablet press fitted with 9.5 mm round normal convex punches (any suitable tablet press could be used). The sealcoat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

Other enteric-coated preparations of this sort can be prepared by one skilled in the art, using these materials or their equivalents.

Other Formulations and Routes of Administration

In alternative embodiments, the compositions as disclosed herein is by an infusion pump (to infuse, for example, the compositions as disclosed herein into the subject's circulatory system) is generally used intravenously, although subcutaneous, arterial, and epidural infusions are occasionally used. Injectable forms of administration are sometimes preferred for maximal effect. When long-term administration by injection is necessary, medi-ports, in-dwelling catheters, or automatic pumping mechanisms are also preferred, wherein direct and immediate access is provided to the arteries in and around the heart and other major organs and organ systems.

In some embodiments, compositions as disclosed herein comprising HbF-inducing agents and/or salts thereof can be administered to a specific site may be by transdermal transfusion, such as with a transdermal patch, by direct contact to the cells or tissue, if accessible, such as a skin tumor, or by administration to an internal site through an incision or some other artificial opening into the body.

Alternatively, in some embodiments, compositions as disclosed herein comprising HbF-inducing agents and/or salts thereof can also be administered to the nasal passages as a spray. Diseases localized to the head and brain area are treatable in this fashion, as arteries of the nasal area provide a rapid and efficient access to the upper areas of the head. Sprays also provide immediate access to the pulmonary system and are the preferable methods for administering compositions to these areas. Access to the gastrointestinal tract is gained using oral, enema, or injectable forms of administration. For example, administration of the compositions as disclosed herein comprising HbF-inducing agents and/or salts thereof to a subject is preferably oral. As a result, the subject can undergo administration of a composition comprising HbF-inducing agents and/or salts at home.

As indicated above, orally active compositions comprising HbF-inducing agents and/or salts thereof are preferred for at least a portion of the cycle of therapy, as oral administration is usually the safest, most convenient, and economical mode of drug delivery. Consequently, compositions as disclosed herein comprising HbF-inducing agents and/or salts thereof can be modified to increase their oral bioavailable by reducing or eliminating their polarity. This can often be accomplished by formulating a composition with a complimentary reagent that neutralizes its polarity, or by modifying the compound with a neutralizing chemical group. Oral bioavailability is also a problem, because drugs are exposed to the extremes of gastric pH and gastric enzymes. Accordingly, problems associated with oral bioavailability can be overcome by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

In some embodiments, the compositions as disclosed herein comprising HbF-inducing agents and/or salts thereof can be used in combination with other agents to maximize the effect of the compositions administered in an additive or synergistic manner. Accordingly, compositions as disclosed herein comprising HbF-inducing agents and/or salts thereof can also comprise proteinaceous agents such as growth factors and/or cytokines. Such proteinaceous agents may also be aminated, glycosylated, acylated, neutralized, phosphorylated, or otherwise derivatized to form compositions that are more suitable for the method of administration to the patient or for increased stability during shipping or storage. Cytokines that are useful to be included in the compositions comprising HbF-inducing agents and/or salts thereof include, but are not limited to, growth factors such as B cell growth factor (BCGF), fibroblast-derived growth factor (FDGF), granulocyte/macrophage colony stimulating factor (GM-CSF), granulocyte colony stimulating factor (G-CSF), macrophage colony stimulating factor (M-CSF), epidermal growth factor (EGF), vascular endothelial growth factor (VEGF), platelet derived growth factor (PDGF) nerve growth factor (NGF), stem cell factor (SCF), and transforming growth factor (TGF). In some embodiments, other agents such as differentiating agents may be useful in combination with a composition as disclosed herein comprising at least one HbF-inducer as disclosed herein and/or salts thereof to prevent or treat a neoplastic disorder. Other differentiating agents include B cell differentiating factor (BCDF), erythropoietin (EPO), steel factor, activin, inhibin, the bone morphogenic proteins (BMPs), retinoic acid or retinoic acid derivatives such as retinol, the prostaglandins, and TPA.

In some embodiments, cytokines and related antigens can be used in combination with a composition as disclosed herein comprising HbF-inducing agents and/or salts thereof, for example, cytokines such as, but not limited to, tumor necrosis factor (TNF), the interleukins IL-1, IL-2, 11-3, IL-4, IL-5, IL-6, etc., recombinant IL receptors, growth factors, colony stimulating factors, erythropoietin (EPO), the interferon (IFN) proteins IFN-α, IFN-β, and IFN-γ; cyclic AMP including dibutyryl cyclic AMP, hemin, DMSO, hydroxyurea, hypoxanthine, glucocorticoid hormones, and cytosine arabinoside. Therapies using combinations of these agents would be safe and effective therapies against malignancies and other forms of cancer.

Compositions as disclosed herein comprising HbF-inducing agents and/or salts thereof can be physiologically stable at therapeutically effective concentrations. Physiological stable compounds of HbF-inducing agents or salts thereof not break down or otherwise become ineffective upon administration to a subject or prior to having a desired effect. Compounds of HbF-inducing agents that are structurally resistant to catabolism, and, thus, physiologically stable, or coupled by electrostatic or covalent bonds to specific reagents to increase physiological stability. Such reagents include amino acids such as arginine, glycine, alanine, asparagine, glutamine, histidine, or lysine, nucleic acids including nucleosides or nucleotides, or substituents such as carbohydrates, saccharides and polysaccharides, lipids, fatty acids, proteins, or protein fragments. Useful coupling partners include, for example, glycol, such as polyethylene glycol, glucose, glycerol, glycerin, and other related substances.

In some embodiments, compositions as disclosed herein comprising at least one HbF-inducer agent as disclosed herein, e.g., at least one or a combination of any of 2-amino-3-hydroxy-N'-(2,3,4-trihydroxybenzyl)propanehydrazide (Benserazide) or 8-Chloro-6,11-dihydro-11-(4-piperidinylidene)-5H-benzo[5,6]cyclohepta[1,2-b]pyridine (Desloratadine) or N-(2-aminophenyl)-4-[N-(pyridin-3-yl-methoxycarbonyl)aminomethyl]benzamide (MS-275), or any pharmaceutically acceptable salt, polymorph or ester thereof, are used in combination with other agents. For example, where the compositions as disclosed herein comprising HbF-inducing agents and/or salts thereof are being used to increase platelets or neutrophils, or increase blood cell proliferation, after, for example, chemotherapy or radiation treatment, a combination therapy can include administering a composition comprising a HbF-inducing agent and/or salts thereof and an additional agent, e.g., an anti-cancer treatments. Such an agent, e.g, anti-cancer agent can be an agent that decreases growth of tumor after the anti-cancer effects of other therapies have decreased. The additional agent or therapy can also be another anti-viral or anti-cancer agent or therapy.

Physiological stability of a composition comprising a HbF-inducing agent and/or salts thereof can be measured from a number of parameters such as the half-life of the a HbF-inducing agent compound or salts thereof, or the half-life of active metabolic products derived from the a HbF-inducing agent compound or salts thereof. In some embodiments, compositions comprising a HbF-inducing agent and/or salts thereof have in vivo half-lives of greater than about fifteen minutes, greater than about one hour, greater than about two hours, and greater than about four hours, eight hours, twelve hours, or longer. A compound of a HbF-inducing agent or its salts is stable using this criteria, however, physiological stability can also be measured by observing the duration of biological effects on the patient. Clinical symptoms that are important from the patient's perspective include a reduced frequency or duration, or elimination of the need for transfusions or chelation therapy. Preferably, a stable composition comprising a HbF-inducing agent and/or salts thereof has an in vivo half-life of greater than about 15 minutes, a serum half-life of greater than about 15 minutes, or a biological effect which continues for greater than 15 minutes after treatment has been terminated or the serum level of the compound has decreased by more than half.

Preferably, compositions as disclosed herein comprising a HbF-inducing agent and/or salts thereof are also not significantly biotransformed, degraded, or excreted by catabolic processes associated with metabolism. Although there may be some biotransformation, degradation, or excretion, these functions are not significant, if the composition is able to exert its desired effect.

In some embodiments, compositions as disclosed herein comprising a HbF-inducing agent and/or salts thereof are also safe at effective dosages. Safe compositions are compositions that are not substantially toxic (e.g. cytotoxic or myelotoxic), or mutagenic at required dosages, do not cause adverse reactions or side effects, and are well-tolerated. Although side effects may occur, compositions are substantially safe if the benefits achieved from their use outweigh disadvantages that may be attributable to side effects. Unwanted side effects include nausea, vomiting, hepatic or renal damage or failure, hypersensitivity, allergic reactions, cardiovascular problems, gastrointestinal disturbances, seizures, and other central nervous system difficulties, fever, bleeding or hemorrhaging, serum abnormalities, and respiratory difficulties.

Compositions useful for treating blood disorders preferably do not substantially affect the viability of a blood cell such as a normal mammalian blood cell. Normal cell viability or the viability of blood cell, e.g., hematopoietic cell can be determined from analyzing the effects of the composition on one or more biological processes of the blood or hematopoietic cell.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation.

Administration of the composition comprising a HbF-inducing agent and/or salts thereof to a subject according to a method of the invention may be for prophylaxis, or alternatively, for therapeutic treatment of a subject diagnosed with a blood disorder as disclosed herein or low platelet count or neutropenia.

In some embodiments, the composition comprising a HbF-inducing agent and/or salts thereof can be used in prophylaxis treatment, for example, where the subject has been diagnosed with cancer and will undergo chemotherapy or radiation therapy for the treatment of cancer, the subject can be administered a composition comprising a HbF-inducing agent and/or salts thereof prior to, or concurrent with or subsequent to, the chemotherapy or radiation therapy, in order to prevent a low platelet counts which typically occur as a side-effect of the chemotherapy or radiation therapy cancer treatment.

In some embodiments, the composition comprising a HbF-inducing agent and/or salts thereof can be administered to an adult, an adolescent, a child, a neonate, an infant or in utero.

In some embodiments, the composition comprising a HbF-inducing agent and/or salts thereof can be administered according to a specific dosing regimen, e.g., in a single or multiple doses, or continuous or sporadic, or as deemed necessary based on an administration regime as determined by measuring absolute neutrophil counts (ANC) in the subject as disclosed herein in the Examples.

In some embodiments, a composition comprising a HbF-inducing agent and/or salts thereof can be administered to a subject via a continuous infusion throughout the cycle of therapy. Alternatively, a composition comprising a HbF-inducing agent and/or salts thereof can be administered to a the subject over a single span of a few to several hours per day every day throughout the first period of the cycle of therapy.

Alternatively, in some embodiments a composition comprising a HbF-inducing agent and/or salts thereof can be administered to a subject in a single parenteral bolus, or orally, daily for several days throughout the treatment regimen or cycle, or weekly.

In some embodiments, a composition comprising a HbF-inducing agent and/or salts thereof can be administered to a subject to augment the treatment of cancer, for example, where a subject is undergoing, or has undergone, or will undergo conventional cancer treatment, for example, chemotherapy, radiation therapy, antibody therapy, and/or other forms of cancer therapy. Some conventional chemotherapeutic agents that would be useful in combination therapy with the methods and compositions of the invention comprising a HbF-inducing agent and/or salts thereof can be administered to a subject include the cyclophosphamides such as alkylating agents, the purine and pyrimidine analogs such as mercaptopurine, the vinca and vinca-like alkaloids, the etoposides or etoposide-like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as anti-insulin and anti-androgen, the anti-estrogens such as tamoxifen, and other agents such as doxorubicin, L-asparaginase, DTIC, mAMSA, procarbazine, hexamethylmelamine, and mitoxantrone. These agents could be given simultaneously, or alternately as defined by a protocol in combination with composition comprising a HbF-inducing agent and/or salts thereof to a subject designed to maximize effectiveness, but minimize toxicity to the patient's body.

In some embodiments, a composition comprising a HbF-inducing agent and/or salts thereof can be prepared in solution as a dispersion, mixture, liquid, spray, capsule, or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil, or a relatively inert solid or liquid. Liquids, pills, capsules or tablets administered orally may also include flavoring agents to increase palatability. Additionally, in some embodiments, a composition comprising a HbF-inducing agent and/or salts thereof can further comprise agents to increase shelf-life, such as preservatives, anti-oxidants, and other components necessary and suitable for manufacture and distribution of the composition. Compositions comprising a HbF-inducing agent and/or salts thereof can further comprise a pharmaceutically acceptable carrier or excipient. Carriers are chemical or multi-chemical compounds that do not significantly alter or affect the active ingredients of the compositions. Examples include water, alcohols such as glycerol and polyethylene glycol, glycerin, oils, salts such as sodium, potassium, magnesium, and ammonium, fatty acids, saccharides, or polysaccharides. Carriers may be single substances or chemical or physical combinations of these substances.

Administration Therapy

In some embodiments, a composition comprising a HbF-inducing agent and/or salts thereof can contain chemicals that are substantially non-toxic. Substantially non-toxic means that the composition, although possibly possessing some degree of toxicity, is not harmful to the long-term health of the patient. Although the active component of the composition may not be toxic at the required levels, there may also be problems associated with administering the necessary volume or amount of the final form of the composition to the patient. For example, if composition comprising a HbF-inducing agent contains a salt, although the active ingredient may be at a concentration that is safe and effective, there can be a harmful build-up of sodium, potassium, or another ion. With a reduced requirement for the composition or at least the active component of that composition, the likelihood of such problems can be reduced or even eliminated. Consequently, although patients may suffer minor or short term detrimental side-effects, the advantages of taking the composition outweigh the negative consequences.

In some embodiments, treatment of a subject with a composition comprising a HbF-inducing agent and/or salts thereof can be according to the methods as disclosed herein can be therapeutic treatment, e.g., a method of treatment of a blood disorder in a subject, for example, a subject with neutropenia or low platelet count. In some embodiments, therapeutic treatment involves administration of a composition comprising a HbF-inducing agent and/or salts thereof according to the methods as disclosed herein to a patient suffering from one or more symptoms of or having been diagnosed as being afflicted with a blood disease or disorder. Relief and even partial relief from one or more of a symptom or a blood disorder may correspond to an increased life span or, simply, an increased quality of life. Further, treatments that alleviate a pathological symptom can allow for other treatments to be administered.

In alternative embodiments, the treatment of a subject with a composition comprising a HbF-inducing agent and/or salts thereof can be according to the methods as disclosed herein can be a prophylactic treatment, for example, to prevent low platelet count of a subject with cancer which is, or has or will undergo cancer treatment, such as for example chemotherapy, radiotherapy and the like. In some embodiments, prophylactic treatments involve administration of a composition comprising a HbF-inducing agent and/or salts thereof according to a method of the invention to a patient having a been recommended to have, or having undergone a cancer treatment, where it is desirable to prevent the loss or decrease of white blood cells in the subject as a side-effect of the cancer treatment. Administration of a composition comprising a HbF-inducing agent and/or salts thereof can begin at the beginning or after, or during (e.g., concurrent with) administration of a cancer therapy (e.g., chemotherapy, radiation therapy) etc., and can continue, if necessary, after cancer treatment, and if necessary for life. In some embodiments, prophylactic treatment is useful where a subject is likely to be exposed to radiation, for example, subjects who are in or located near an area of a radiation disaster accident, or subjects who are working in a recovery effort in an area that has had a radiation disaster or working in or near a radiation exposure. As demonstrated herein, both prophylactic and therapeutic uses are readily acceptable, because these compounds are generally safe and non-toxic.

In some embodiments, a subject can be administered a composition comprising a HbF-inducing agent as disclosed herein and/or salts thereof can be according to the methods as disclosed herein as a blood stimulant increase hematopoietic cell proliferation, for example, to increase hematopoietic stem cell production prior to bone marrow donation. In some embodiments, a composition comprising at least one or a combination of any of 2-amino-3-hydroxy-N'-(2,3,4-trihydroxybenzyl)propanehydrazide (Benserazide) or 8-Chloro-6,11-dihydro-11-(4-piperidinylidene)-5H-benzo[5,6]cyclohepta[1,2-b]pyridine (Desloratadine) or N-(2-aminophenyl)-4-[N-(pyridin-3-yl-methoxycarbonyl)aminomethyl] benzamide (MS-275), or any pharmaceutically acceptable salt, polymorph or ester thereof, can be used to induce erthropoiesis or induce blood cell proliferation, as demonstrated in FIG. 8. For example, similar to the administration of a mobilizing agent, such as G-CSF and GM-CSF as disclosed in U.S. Pat. No. 6,261,549 and U.S. Patent Application 2009/0155225 (which are incorporated herein in their entirety by reference) to increase hematopoietic cell and hematopoietic stem cell production in subjects, herein, a composition comprising a HbF-inducing agent and/or salts thereof can be administered to a donor subject, for example, to increase hematopoietic cells or stimulate blood cell proliferation prior to bone marrow donation, or alternatively a bone marrow stem cell donation. Accordingly, in some embodiments, administration of a composition comprising a HbF-inducing agent as disclosed herein and/or salts thereof according to a methods as disclosed herein to a subject who will donate bone marrow, or bone marrow-derived stem cells, or blood, where it is desirable to increase hematopoietic cells and/or white blood cells in the donor subject prior to the donation.

Assays to Identify HbF-Inducing Agents

In some embodiments, the present invention provides methods an assay to identify actions which function as HbF-inducers as disclosed herein, e.g., induce fetal globin mRNA expression in vivo, and/or increase the number of fetal hemoglobin producing cells. In some embodiments, an agent is contacted with a cell comprising a nucleic acid construct comprising a locus control region (LCR-HS2) linked to the γ-globin promoter, or a portion thereof, operatively linked to at least one nucleic acid encoding a reporter gene. In some embodiments, there are at least 2, or at least 3, or more reporter genes operatively linked to the locus control region (LCR-HS2), γ-globin promoter construct. In some embodiments, the locus control region is a μLCR. In some embodiments, the γ-globin promoter is $^A$γ-promoter. In some embodiments, the reporter gene encodes a protein with fluorescent activity and/or chromogenic activity, for example but not limited to fluorescent proteins, for example green fluorescent protein (GFP) or variants thereof or bioluminescent proteins, for example luciferase or variants thereof. In some embodiments, the reporter gene encodes a protein with fluorescent and/or chromogenic activity or variants or functional fragments thereof, for example, a chromogenic protein can be a bioluminescent protein or functional variants thereof, such as but not limited to a luciferase or functional fragments or modified functional versions thereof.

In some embodiments, the nucleic acid construct can comprise a β-globin promoter operatively linked to a different reporter gene. Thus, an agent that functions as a HbF-inducer will result in a greater change in the signal from the reporter gene which is operatively linked to the γ-globin promoter, as compared to the signal produced from the reporter gene which operatively linked to the β-globin promoter. This is useful to identify agents which induce expression of γ-globin expression as compared to induce expression of β-globin gene expression.

In some embodiments, the agent is a small molecule, nucleic acid, nucleic acid analogue, aptamer, ribosome, peptide, protein, antibody or variants or fragments thereof. An agent that functions as a HbF-inducer will result in a change in the signal from the reporter gene, where the change is a result of contacting the cell with agent as compared to when the cell is not contacted with the agent.

In some embodiments, the present invention provides methods of identify an agent functions as HbF-inducer, e.g., induce fetal globin mRNA expression in vivo, and/or increase the number of fetal hemoglobin producing cells in a cell, the methods comprising; (a) providing a cell containing a nucleic acid construct comprising at least a nucleic acid sequence encoding a locus control region (LCR-HS2) linked to the γ-globin promoter, or a portion thereof, which is operatively linked to a nucleic acid encoding a reporter gene; and (b) contacting the cell or an extract of the cell with an agent; and (c) measuring the signal from the reporter gene, whereby a change in the signal from the reporter gene in the presence of the agent compared to the signal from the reporter gene in the absence of the agent indicates the agent modulates the γ-globin expression. In some embodiments, where the change is an increase in the signal in step (c) indicates the agent activates γ-globin gene expression.

In some embodiments, an agent used to identify an agent that functions as an HbF-inducer is a small molecule, nucleic acid, nucleic acid analogue, aptamer, ribosome, peptide, protein, antibody, or variants and functional fragments thereof. In some embodiments, an antibody can be, for example but not limited to, a recombinant antibody, humanized antibody, chimeric antibody, modified antibody, monoclonal antibody, polyclonal antibody, miniantibody, dimeric miniantibody, minibody, diabody or tribody or functional variants, functional analogues or functional modified versions thereof. In some embodiments, a nucleic acid is DNA, RNA, nucleic acid analogue, peptide nucleic acid (PNA), pseudo-complementary PNA (pcPNA), locked nucleic acid (LNA) or functional analogues thereof, where an RNA can be, for example but not limited to, a small inhibitory RNA, siRNA, microRNA, shRNA, miRNA and functional analogues and homologues and functional variants thereof.

In some embodiments, the cells may be freshly isolated, cultured, genetically engineered as described above, or the like. A cell may be environmentally induced variants of clonal cultures: e.g. split into independent cultures and grown under distinct conditions. Alternatively, a cell can be a somatic cell or a stem cell or progenitor, and can be a variant with a desired pathological characteristic. For example, the desired pathological characteristic includes a mutation and/or polymorphism which contribute to blood disease or disorder pathology.

In alternative embodiments, the methods of the invention can be used to screen for HbF-inducing agents in which a cell comprising a particular mutation and/or polymorphism which respond differently compared with a wild-type cell, e.g., cell without the mutation and/or polymorphism, therefore the methods can be used for example, to asses an effect of a particular drug and/or agent cells from a defined subpopulation of people and/or cells, therefore acting as a high-throughput screen for personalized medicine and/or pharmogenetics. The manner in which cells respond to an agent, particularly a pharmacologic agent, including the timing of responses, is an important reflection of the physiologic state of the cell.

The agent used in the screening method can be selected from a group of a chemical, small molecule, chemical entity, nucleic acid sequences, an action; nucleic acid analogues or protein or polypeptide or analogue of fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein agent within the cell. An agent also encompasses any action and/or event the cells are subjected to. As a non-limiting examples, an action can comprise any action that triggers a physiological change in the cell, for example but not limited to; heat-shock, ionizing irradiation, cold-shock, electrical impulse, light and/or wavelength exposure, UV exposure, pressure, stretching action, increased and/or decreased oxygen exposure, exposure to reactive oxygen species (ROS), ischemic conditions, fluorescence exposure etc. Environmental stimuli also include intrinsic environmental stimuli defined below. The exposure of the cell in the assay to a test agent may be continuous or non-continuous.

In some embodiments, the agent is an agent of interest including known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

The agents include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

Parameters are quantifiable components of a cell in the assay is the detection of one or more reporter genes. In a second screen, the candidate HbF-inducer agent can be assessed to measure the expression of the γ-globin expression (e.g., protein expression or mRNA expression) in cells in vitro and/or in vivo, for example, using the assays as disclosed herein in the Examples. In some embodiments, the reporter gene expression from the assay construct and/or γ-globin gene expression can be accurately measured, desirably in a high throughput system.

In some embodiments, an output parameter from the assay screen can be any increase in at least one reporter gene and/or γ-globin gene expression. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. In some embodiments, the assay is a computerized assay or a robotic high-throughput system operated through a computer interface.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened using the assays as disclosed herein by adding the agent to at least one and usually a plurality of the cells comprising the nucleic acid construct, e.g., a population of cells, and can be performed concurrently with a test well with a cell lacking the agent (e.g., reference culture). The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method. In some embodiments, agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Optionally, a cell used in the screen can be manipulated to express desired gene products. Gene therapy can be used to either modify a cell to replace a gene product or add or knockdown a gene product, e.g., reproduce a cell comprising the genes of a genetic blood disorder. Techniques for transfecting cells are known in the art.

Kits

The invention also provides kits or pharmaceutical packages that comprise a combination of one or more of the HbF-inducing agents as disclosed herein, e.g., at least one of, or any combination of HbF-inducing agent, which include, ambroxol, benserazide, desloratadine, resveratrol, NSC-95397, idarubicin or MS-275, or auronafin testosterone, or an analogue, or salt or derivative thereof for use in the prevention and/or treatment of the blood disorders and diseases as described herein. In addition to at least one or a combination of a HbF-inducing agent, which include, ambroxol, benserazide, desloratadine, resveratrol, NSC-95397, idarubicin or MS-275, or auronafin testosterone, or an analogue, or salt or derivative thereof the form of, for example, tablets, capsules, or lyophilized powders, the kits or packages can include instructions for using the HbF-inducing agent in the prevention and/or treatment of a blood disorder or diseases as disclosed herein. A combination of at least one or a combination of a HbF-inducing agent, which include, ambroxol, benserazide, desloratadine, resveratrol, NSC-95397, idarubicin or MS-275, or auronafin testosterone, or an analogue, or salt or derivative thereof can be provided in the kits or packages in a bottle or another appropriate form (e.g., a blister pack). Optionally, the kits or pharmaceutical packages can also include other pharmaceutically active agents (see, e.g., the agents listed above), and/or materials used in administration of the drug(s), such as diluents, needles, syringes, applicators, and the like.

In another embodiment, the present invention provides kits comprising the assay as disclosed herein, where the assay can be used to identify HbF-inducing agents as disclosed herein. In some embodiments, the kit can comprise at least one cell, or a population of cells comprising at least one construct, e.g., a construct comprising a locus control region (LCR-HS2) linked to the γ-globin promoter, or a portion thereof, operatively linked to at least one nucleic acid encoding a reporter gene. In some embodiments, the construct comprises the nucleic acid encoding the locus control region is a μLCR In some embodiments, the construct can also comprise a nucleic acid encoding a β-globin promoter, or fragment thereof operatively linked to a different reporter gene. Thus, the kit can comprise an assay useful to identify an HbF-inducer agent which activates γ-globin expression to a greater extent than inducing expression of β-globin expression. In some embodiments, the kit can also comprise a positive control HbF inducer agent, e.g., MS-275, desloratadine or benserazide. In some embodiments, the kit can also comprise a negative control agent. In some embodiments, the kit can comprise one or more agents required for detection of a chromogenic protein, or a bioluminescent protein or the like. In some embodiments, the kit can comprise a control cell line comprising a construct which does not include a γ-globin promoter, or alternatively, the control cell line does not comprise a construct as disclosed herein. In some embodiments, the kit can comprise instructions for using the assay to identify one or more HbF-inducing agents. In some embodiments, the kit can comprise the assay and reagents for use in a high-throughput manner.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

The present invention is well adapted to carry out the objects and obtain the ends and advantages mentioned, as well as those inherent therein. The methods, compositions and systems and kits are representative of certain embodiments, are exemplary, and are not intended as limitations on the scope of the invention. Modifications therein and other uses are also contemplated herein. These modifications are encompassed within the spirit of the invention and are defined by the scope of the claims. Varying substitutions and modifications may be made to the invention disclosed herein without departing from the scope and spirit of the invention.

Certain claims are presented in dependent form for the sake of convenience, but Applicant reserves the right to rewrite any dependent claim in independent form to include the limitations of the independent claim and any other claim(s) on which such claim depends, and such rewritten claim is to be considered equivalent in all respects to the dependent claim in whatever form it is in (either amended or unamended) prior to being rewritten in independent format. It should also be understood that, unless clearly indicated to the contrary, in any methods claimed herein that include more than one act, the order of the acts of the method is not necessarily limited to the order in which the acts of the method are recited, but the invention includes embodiments in which the order is so limited.

EXAMPLES

Materials and Methods

Dual Luciferase Reporter Assay

The inventors conducted a counter-screening assay to demonstrate and confirm the γ-globin-specificity of identified compounds, using an assay established in our laboratory, which measures γ-globin gene promoter induction relative to β-globin gene promoter induction. This assay is fluorescence-based, and consists of a dual-luciferase reporter construct containing the LCR and the γ-globin promoter linked to renilla luciferase and the Aγ-globin promoter linked to firefly luciferase (µLCRβprRlucAγprFluc cassette), stably-transfected into GM979 cells. The orientation of the promoters and µLCR allowed detection only of strong, specific inducers of the γ-globin gene promoter. This assay is also been predictive of in vivo HbF-inducing activity.

Erythroid Progenitor Cultures

Fetal globin-inducing activity in human erythroid progenitors was assessed. Human erythroid progenitors were cultured from peripheral blood samples, exposed to the test compounds at varying concentrations and for varying durations and analyzed for globin chain mRNA ratios. Erythroid progenitors were cultured from cord blood CD34+ cells. Briefly, CD34+ cells in the human cord blood were separated using a Ficoll-paque density gradient. CD34+ cells were cultured in H4230 medium containing 2 mM L-glutamine, 1% Methylcellulose in Iscove's Medium, 30% Fetal Bovine Serum, 1% Bovine Serum Albumin and 10-4 M β-mercaptoethanol. Methylcellulose H4230 medium was supplemented with EPO (0.5 U/ml) and IL-3 (20 ng/ml) to support BFU-e growth. Cells were cultured in 35×100 mm mini-dishes and incubated in a humidified atmosphere containing 5% $CO_2$, at 37° C. Different concentrations of the test compounds were added at the time the cultures were established. Each compound was tested in three different cultures. BFU-e colonies grown in mini-dishes were counted on day 14 and harvested for mRNA analysis.

mRNA Analysis by Real-Time PCR

On day 14, RNA was extracted from cultured erythroid cells, and relative quantification PCR was performed. Briefly, cDNA was generated from equal amounts of total RNA extracted using The PerfectPure RNA Purification Kit (5 Prime Inc Gaithersburg, Md.). Real-time PCR was performed using an ABI 7500 Real-Time PCR system (Applied Biosystems, Foster City, Calif.). Levels of globin mRNA were calculated by the ΔΔCt method. Isolated total RNA was used as a template for cDNA synthesis and real-time PCR was performed using the following primer sets: TCACAGAGGAG-GACAAGGCTA (SEQ ID NO:1) and GAGATCATCCAG-GTGCTTT (SEQ ID NO: 2). GAPDH levels were used for standardization. Western blotting Nuclear extract of K562 cells and 14-day-old BFU-e were analyzed by electrophoresis using 5-24% gradient SDS-polyacrylamide mini-gels (BIO-RAD Laboratories. Hercules Calif.). Proteins in the gels were transferred to Immobilon-P membranes. Blots were then incubated with BCL11A polyclonal (Novus Biologicals, Littleton Co) or mouse monoclonal (Santa Cruz Biotechnology, Santa Cruz Calif.) antibodies, after washing blots were incubated with anti-rabbit IgG-horseradish peroxidase secondary antibody (ECL, Little Chalfont Buckinghamshire UK). BCL11A bands were detected on the X-ray film using Western Lightning Reagents (Perking Elmer Inc, Waltham, Mass.).

Studies in Non-Human Primates

Studies to evaluate pharmacokinetic properties and γ-globin induction were performed in juvenile baboons (*Papio hamadryas anubis*). Briefly, animals were chronically phlebotomized on a daily basis to achieve stable anemia, maintaining a total hemoglobin level of 7.0 to 7.5 g/dl. Candidate compounds were administered intravenously or orally once daily in single doses for pharmacokinetic studies, or once daily in single doses, 4-5 days per week for 4-5 weeks, for pharmacodynamic studies. The compound Desloratadine was administered intravenously to a baboon at doses of 50 or 200 mg/kg once daily, 5 days per week for 4 weeks, to evaluate γ-globin gene expression. MS-275 was administered intravenously at a dose of 10 mg/kg once daily, 4-5 days per week for four weeks, to assess γ-globin gene expression in baboon 5002. Benserazide, administered at 1 or 3 mg/kg in baboon 1509 increased both fetal hemoglobin mRNA and also the total haemoglobin levels, and increased blood cell proliferation. Levels of γ-globin mRNA expression and globin chain synthesis were assessed in baboons before and during treatment with test compounds. A washout period between administrations of different compounds in the same baboon was provided. MS-275 and desloratidine both induced fetal globin mRNA and total hemoglobin levels increased following MS-275 administration.

Example 1

A human cell-based assay which was previously used in low throughput assays, utilizing a 1.4-kilobase (kb) KpnI-BglII fragment of the HS2 of the locus control region (LCR) linked to the γ-globin gene promoter and the enhanced green fluorescent protein (EGFP) reporter gene, was adapted for high throughput screening and employed as the primary screen (FIG. 1A). Cytotoxic activity was assayed in a simultaneous counter screen. A number of hits were identified as being more potent than positive controls (such as butyrate). Several hits were immediately eliminated from further development as potential hemoglobinopathy therapeutics because of cytotoxicity (e.g., Idarubicin) or undesirable off-target effects, but nonetheless validated the HTS itself and were validated in secondary confirmatory assays as highly-potent HbF-inducers.

The HTS assay identified eight FDA-approved drugs as potent inducers of γ-globin gene expression, with activity at 1-2 logs lower concentrations (1000-fold higher potency) than prior generation therapeutic candidates. The γ-globin-specificity of hits was determined in a secondary assay employing a stably-transfected dual-luciferase reporter construct containing the LCR and the β-globin promoter linked to renilla luciferase and the Aγ-globin promoter linked to firefly luciferase (µLCRβprRlucAγprFluc cassette) (FIG. 2B).

The inventors demonstrated that clinical-stage or clinically-approved agents, including Ambroxol at 1 µM, Desloratadine at 1 µM, Resveratrol at 10 µM, Benserazide at 0.03 µM (or a range of 30 nM-5 µM), the HDAC inhibitor MS-275 at 5 µM, and an established bioactive, NSC-95397, at 1 µM were all significantly more active in this assay than sodium Butyrate at 2000 µM, with MS-275, Benserazide and Resveratrol being the most active at inducing γ-globin mRNA expression.

These drugs were then assayed for their ability to induce γ-globin mRNA expression in cultured primary human erythroid progenitors, at concentrations which are pharmacologically achievable in humans. Drugs significantly more active in γ-globin mRNA induction than the positive control (2-fold induction) in this system included Ambroxol (3-fold), Desloratadine (up to 6-fold), Resveratrol (up to 3-fold), Benserazide (up to 5-fold), and MS-275 (up to 3.7-fold). Two agents were subsequently studied in anemic baboons, and demonstrated in vivo induction of γ-globin mRNA, HbF, and F-reticulocytes. Unexpectedly, rises in total hemoglobin (>1 gm/dL) also occurred with 2 agents. Thus, the inventors have discovered a panel of structurally- and functionally-unrelated compounds which demonstrate significantly greater HbF-inducing activity, with up to 1000-fold higher potency, than current HbF-inducers which have significant activity in clinical trials.

Additionally, some of the drugs identified by HTS have entirely benign safety profiles. These candidates could be clinically evaluated rapidly and at significantly less cost than new chemical entities, which require extensive toxicology, manufacturing, and clinical evaluation. These findings demonstrate the utility of a high-throughput screening program based on γ-globin gene promoter induction.

HTS Assay

An assay previously used in low throughout screens was adapted for high throughput screening effort and allowed investigation of entirely new libraries of known bioactive compounds and therapeutics, including a library of therapeutic agents which are already FDA-approved (for other indications) for γ-globin inducing activity. The screening assay utilizes a cell-based reporter, stably transfected with a construct containing the 1.4-kilobase (kb) KpnI-BglII fragment of the human HS2 of the locus control region (LCR) linked to the γ-globin promoter and the enhanced green fluorescent protein (EGFP) reporter gene (FIG. 1A), as previously described. Because EGFP messenger RNA (mRNA) has long stability, positive changes (up until our newest results, below) averaged 1.2- to 2-fold, and weak inducers are not detectable in this system. Inductions of 2-fold or higher indicate very strong inducers of γ-globin gene activity.

The results of HTS screening demonstrated a number of suitable candidates, or hits, in the FDA-approved-drug library, from drugs with highly diverse structures, with activity higher than agents that were active in prior clinical trials. The inventors discovered that some compounds have much higher potency than our positive (clinical stage) control in the assay. A few of these newly recognized therapeutics have high specificity and do not have off-target effects that would be detrimental for long-term use.

The HTS assay was developed in 96-well format on a Tecan SpectraFluor Plus, incorporating multiple positive and negative control wells in each plate, generating 40-80 assay points for each. Some preliminary optimization of 96-well format was carried out: (i) Optimization of number of cells per well; (ii) Identification of ideal time points for fluorescent measurements.

In this 96-well format, a (positive) signal of intensity of 9000 RFUs was demonstrated in a volume of 100 µl, which is more than sufficient for accurate analyses. In these pilot studies, a signal-to-background ratio of at least 7 was demonstrated. The mean and standard deviations for the two controls were calculated, and the Z' factor was generated (Z'=0.71) for this assay.

Out of a small, cherry-picked group of compounds from an "FDA-approved compound" library, a number of hits were identified. Several were immediately eliminated from further development as potential hemoglobinopathy therapeutics because of cytotoxicity (e.g. idarubicin), but were nonetheless validated in confirmatory assays as potent HbF-inducers. A small panel of candidates have shown higher activity and potency (activity at lower concentrations) than clinically active therapeutics in current trials.

Herein, the inventors investigated 5 diverse chemical libraries including bioactive compounds and therapeutics which are already FDA-approved (for other indications) for γ-globin inducing activity. The HTS identified a number of candidates, or hits. Interestingly, hits in the FDA-approved-library included drugs with highly diverse structures, and higher activity than agents in current clinical trials. Some have much higher potency than the positive (clinical stage) control (Butyrate). A select few of these newly recognized therapeutics are known not to have off-target effects that could be detrimental for long-term application.

Figure 2A:
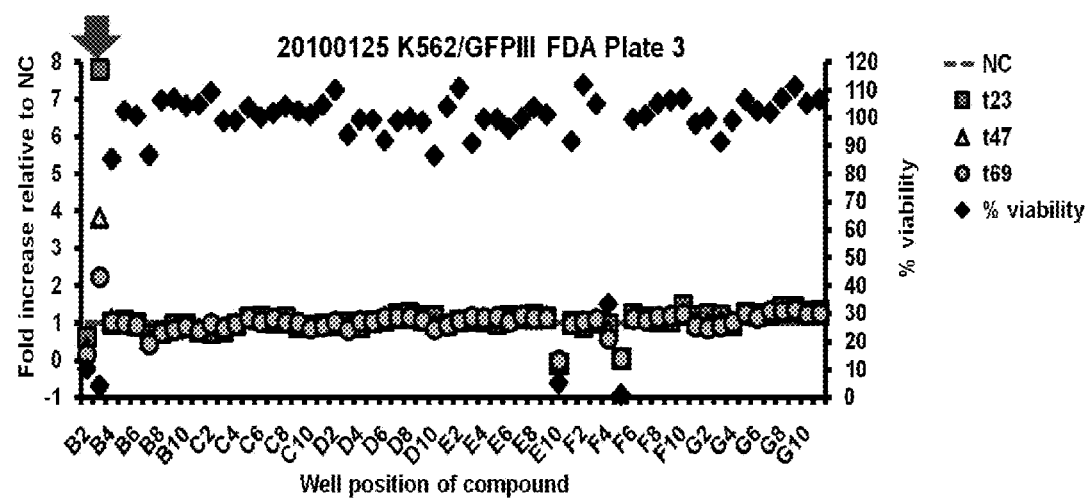
FIG. 2A shows the results from a screen plate assay using the γ-globin reporter cell line, showing the fold increase relative to NC (negative control) and % of viable cells. The arrow identified a hit candidate compound (Idarubicin) selected for further analysis which had an 8-fold induction of the γ-globin promoter.
Figure 2B:
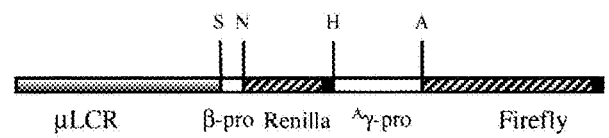
FIG. 2B shows a construct for a follow-up assay used to validate the HTS. Cell-based screen for γ-globin inducing compounds in GM979 cells (Skarpidi, et al. Blood 2000; 96:321-326). Mini-gene construct integrated into GM979 cell genome. The readout is Firefly/Renilla luciferase ratio, and is designed to identify only strong inducers of the γ-globin promoter, and specificity for the γ- vs. the □γ-globin gene. This second assay confirmed 12/15 candidates.
Figure 3:
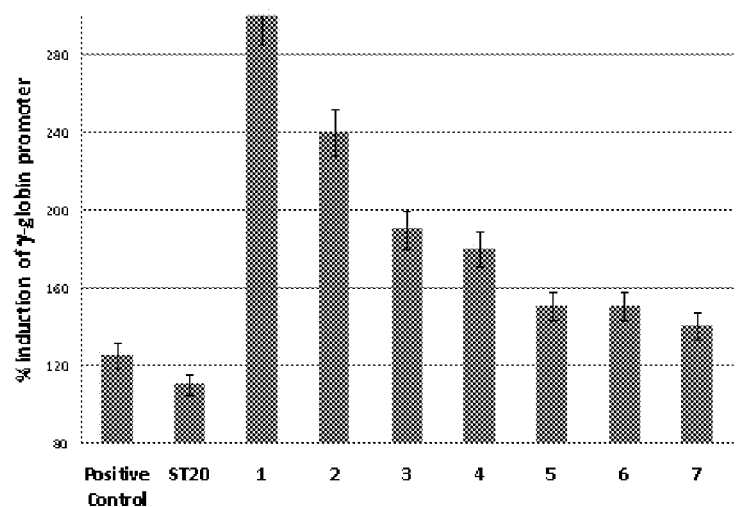
FIG. 3 show a histogram of the analysis of selected hit compounds from a HTS, showing the percentage γ-globin fold-induction of selected compounds relative to a positive control compound included on each plate. ST20, an HbF-inducing compound currently in clinical testing, is also shown.
Figure 4A:
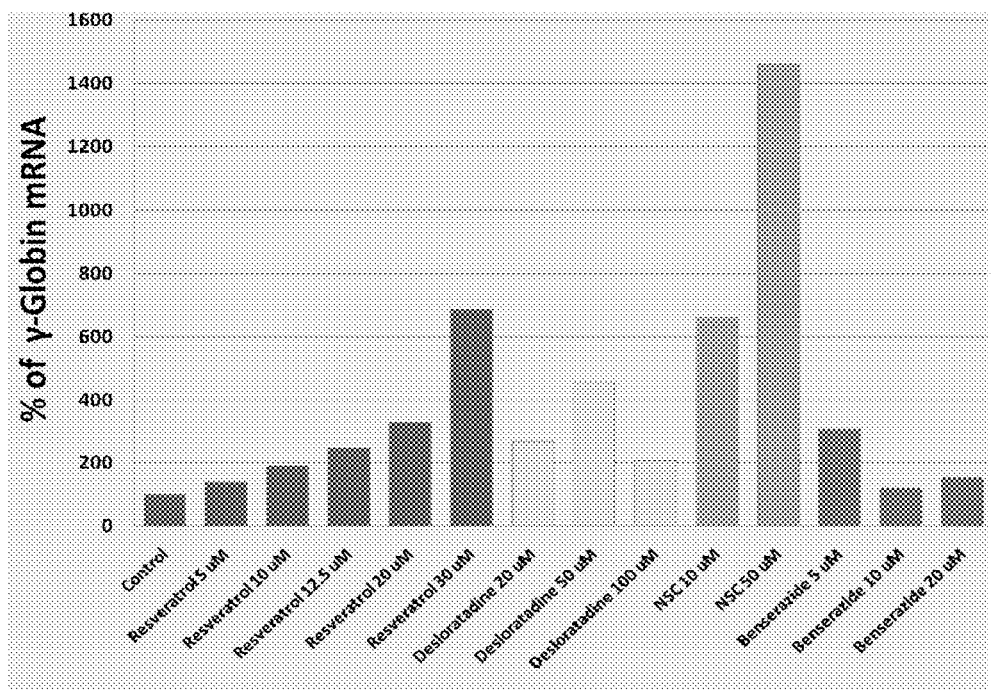
Figure 5A:
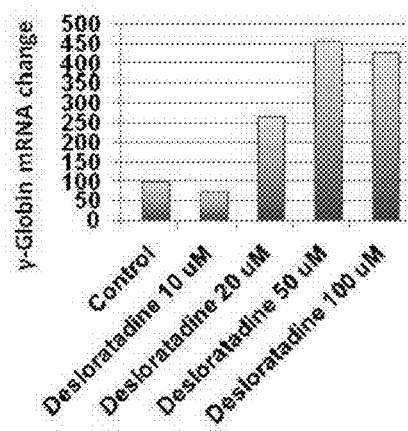
FIG. 5A-5C shows Deslorathadine, Resveratrol and NSC increases γ-Globin mRNA gene expression in K562 cells.
Figure 5B:
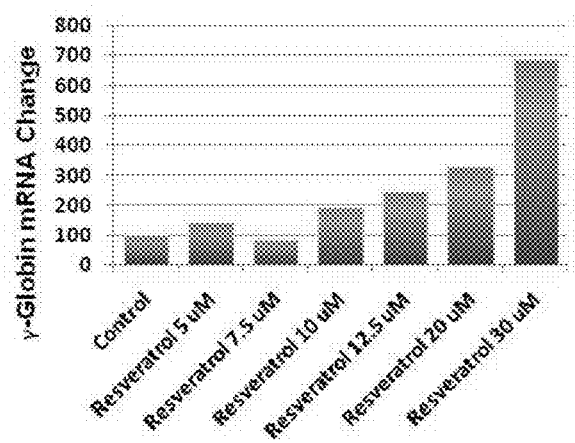
Figure 5C:
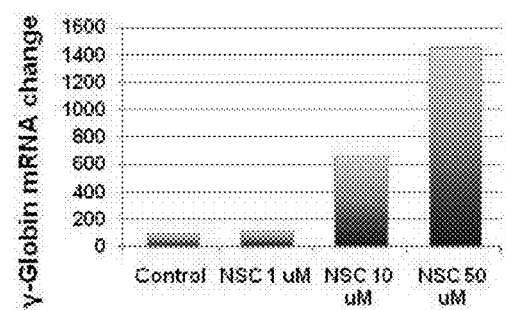
Figure 6:
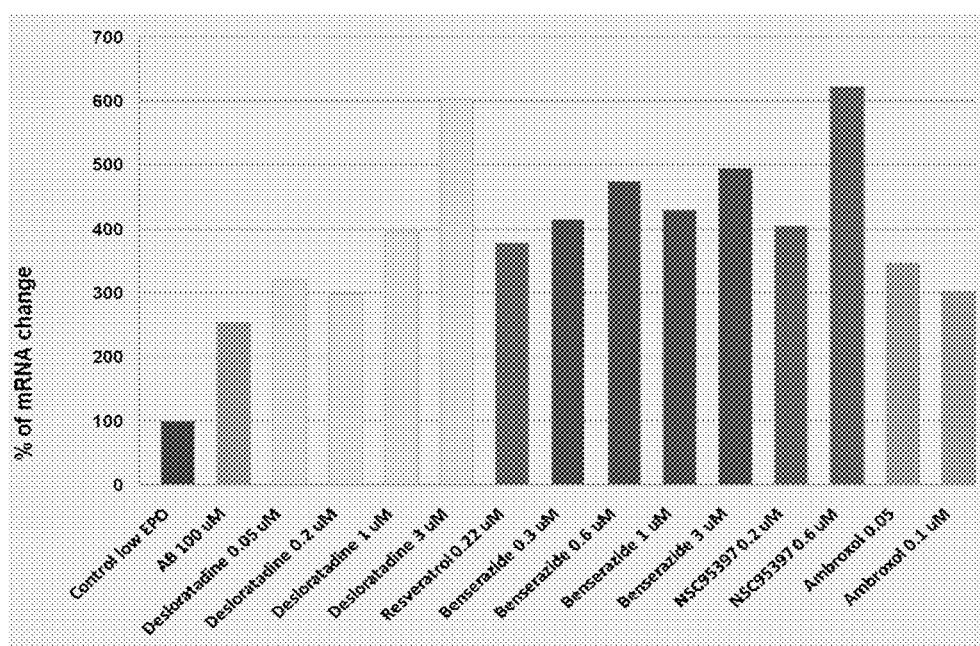
FIG. 6 shows effects of AB, Desloratadine, Resveratrol, Benserazide, and NSC5397 and Ambroxol increases % γ-Globin mRNA gene expression in BFU-e (Burst-forming units-erythroid) cells. Desloratadine e (3 μM), Benserazide (3 μM), and NSC5397 (0.6 μM) show greatest effect in increasing % of γ-globin mRNA expression.

FIG. 2A shows an example of a readout from a pilot screen plate assay using the γ-globin reporter cell line. The arrow shows one potential hit candidate with 8-fold induction of the γ-globin promoter (Idarubicin). Selected candidate hits were assessed in a follow-up assay used to validate the HTS. Cell-based screen for γ-globin inducing compounds in GM979 cells (Skarpidi, et al. Blood 2000; 96:321-326). γ-globin was analysed by RT-PCR (FIG. 3, 4A, 4B, 5A-5C).

Figure 9:
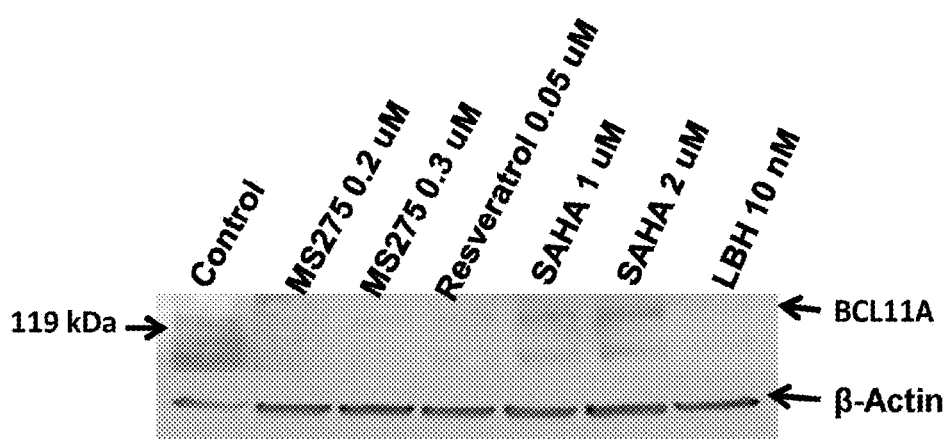
FIG. 9 shows a western blot analysis of Bcl11A in nuclear extracts of cord blood CD34+ cells cultured in Phase II media, treated with MS275, resveratrol, SAHA, or LBH and using specific antibodies.
Figure 10A:
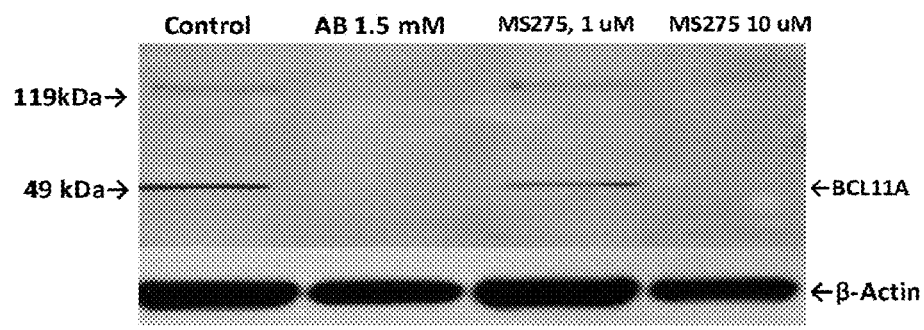
FIG. 10A-10B shows a western blot analysis of Bcl11A in nuclear extracts of K562 cells treated with arginine butyrate (AB) and MS275.
Figure 10B:
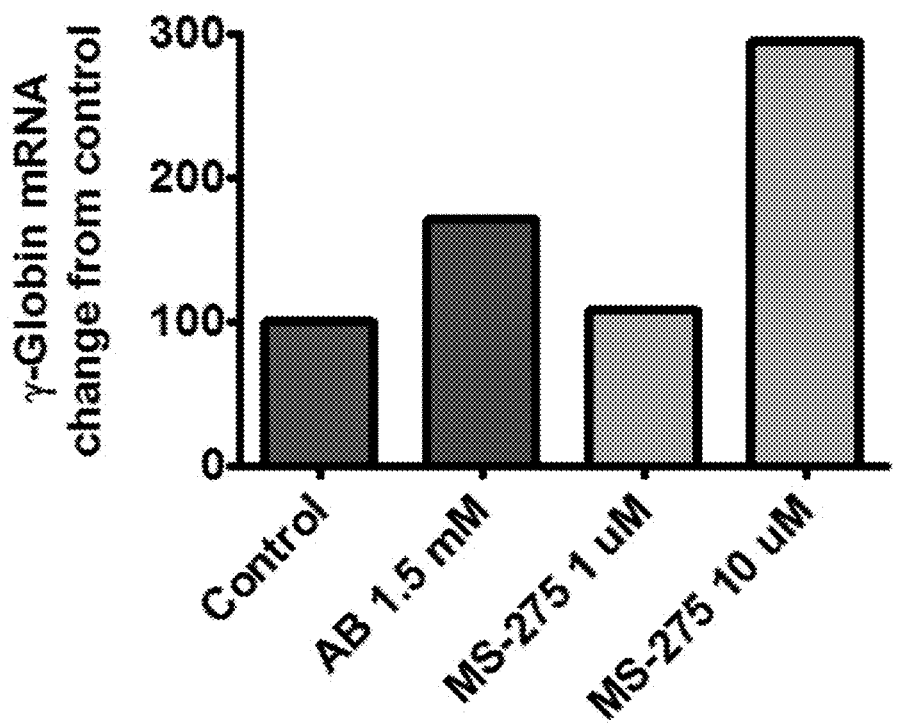

To evaluate potential mechanisms by which the new agents may influence γ-globin expression, BCL-11A protein expression was assessed by Western Blot (FIG. 10A). γ-Globin induction was associated with BCL-11A suppression; induction by MS-275 and BCL-11A suppression were dose-dependent. (FIG. 10B). BCL-11A suppression was detected with HDAC inhibitors MS-275 and LBH589, and a new candidate Resveratrol, but not by SAHA in primary erythroid cells (FIG. 9).

FIG. 8 shows examples of 3 drug candidates that enhance erythroid growth. A small panel of drugs are active at 1/100 to 1/1000 of the concentration required by Butyrate (200 uM) (ie, have higher potency for inducing γ-globin).

Example 2

Figure 12A:
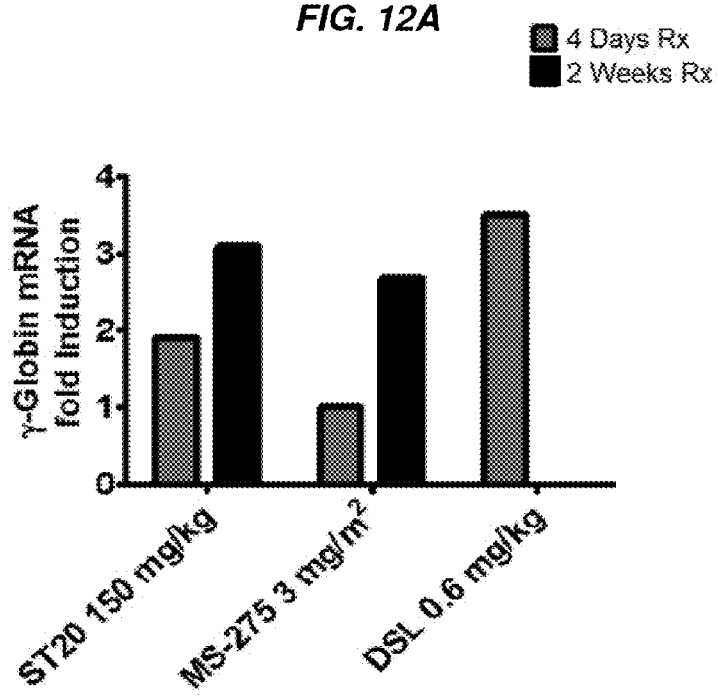
FIGS. 12A-12B show HTS agents induce g-globin mRNA and total Hb in non-human primates in vivo.
Figure 12B:
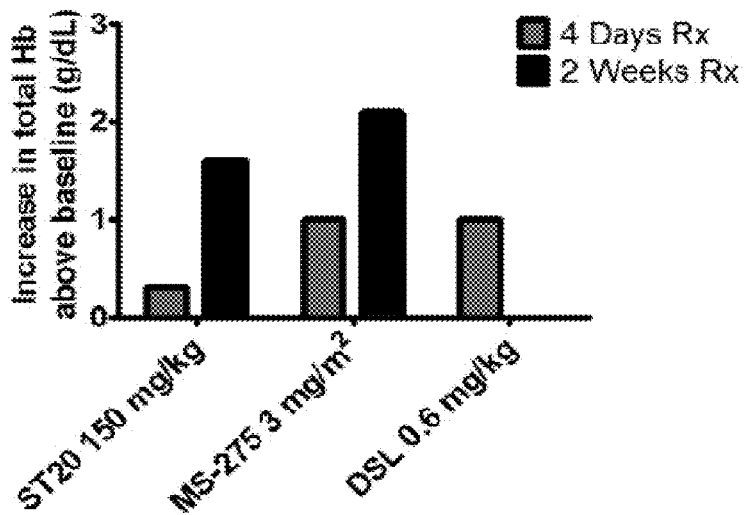

Chronically catheterized baboons were phlebotomized daily to create chronic anemia with total hemoglobin levels (Hb) between 7.0 to 7.5 g/dl which simulates the expanded erythropoiesis and anemia in sickle cell disease and beta thalassemia. Blood counts were drawn and total Hb (hemoglobin) and reticulocytes were analyzed on a hemavet analyzer. Fetal globin mRNA was analyzed by RT-PCR and proportions for f-cells were analyzed by flow cytometry. In one baboon, MS-275 (3 mg/m$^2$), ST20 (positive control) were each administered for 2 weeks with a washout period between each test agent. Desloratidine (0.6 mg/kg) was administered for 4 days following a washout period. Blood counts were obtained at least 3 days/week. Hemoglobin levels were compared after 4 days of Desloratidine (0.6 mg/kg) treatment and after 4 days and 2 weeks of treatment with the positive control ST20 (sodium 2,2 dimethylbutyrate), MS-275 was given twice per week, and Desloratidine and ST20 were given daily (FIGS. 12A-12B).

Example 3

Inducers of Fetal Globin and Hematopoiesis

Example of Increased Red Blood Cell Production Induced by Benserazide in an Anemic Nonhuman Primate Undergoing Daily Blood Withdrawal.

A third non-human primate experiment demonstrated that Benserazide increases hemoglobin levels and hematocrit % in blood in vivo. Baboon 1509 (weight 10.9 kg) was phlebotomized to induce anemia and marrow expansion, similar to the hemoglobin disorders. After phlebotomizing from hemoglobin level of 14.3 to 6.8 and then to a stable level with a phlebotomy volume of 37 mls of whole blood withdrawn daily, the hemoglobin level measured was to be at 7.6 g/dl and the hematocrit was 25.6%. After administration of Benserazide at 1 mg/kg and then 2 mg/kg, the hemoglobin level increased to 8.9 g/dl and the hematocrit increased to 28% by 2 weeks after administration and despite the continuing blood withdrawal daily. This result strongly demonstrated that Benserazide (at doses of at least 1 mg/kg and 2 mg·kg) stimulates red blood cell production over the increased levels induced by endogenous erythropoietin.

Fetal Globin Induction (HbF Protein Levels and Fetal Globin mRNA) in 2 Anemic Baboons Treated with Desloratidine and/or MS-275

Baboons HL-25 and HD50 were phlebotomized daily to create anemia with erythroid expansion. When stably anemic, Desloratidine (0.6 mg/kg) was administered orally, fetal hemoglobin (HbF) protein levels were assayed. Typically this assay produces only minor results, as the blood withdrawal daily reduces the detection of new HbF production. However, surprisingly HbF levels increased above levels produced by erythroid stress alone by 170% in Baboon HD50 and by 193% in Baboon HL25. With administration of MS-275 (3 mg/m$^2$) to Baboon HD50, HbF increased by 115%.

Accordingly, the inventors demonstrate that fetal globin (HbF) mRNA increased above baseline as follows: Desloratidine produced a 350% and 386% increase above baseline in baboons HD50 and HL25 respectively; MS-275 treatment increased fetal globin mRNA by 270% in HD50 (see Table 1).

Furthermore, the effects of Desloratidine, MS-275 and Benserazide on increasing HbF expression in vivo were surprisingly achieved at much low doses of the test agents as compared to other therapeutics (e.g., sodium 2,2 dimethylbutyrate (ST-20) which requires 50-150 mg/kg in baboons, and requires about 3-fold less in humans, e.g., about 20-50 mg/kg in humans). Furthermore, the increases in fetal globin (HbF) mRNA occurred after 2 weeks of treatment with ST-20, whereas fetal globin induction and increased in HbF was detected within 4 days of desloratidine treatment in the same baboon.

Table 1:

Increase in γ-globin mRNA above baseline in Baboons treated with oral HbF inducers Desloratadine, MS-275, and Benserazide.

| Compound oral dose | Baboon HD50 | Baboon HL25 | Baboon 1509 |
|---|---|---|---|
| ST20 (150 mg/kg) | 310% | | |
| Desloratadine (0.55 mg/kg) | 350% | 386% | |
| MS-275 (0.18 mg/kg) | 270% | | |
| Benserazide (2 mg/kg) | | | 193% |

Novel Therapeutic Agents in Erythroid Progenitors Cultured from Human Cord Blood, Adult Bone Marrow and Peripheral Blood, and from Subjects with Hemoglobin Disorders.

Accordingly, the inventors have demonstrated HbF inducers which can induce fetal globin expression at much lower concentrations and doses as compared to concentrations and doses required for known inducers therapeutic candidates, such as the short chain fatty acids (SCFAs) and derivatives (SCFADs) which require about 100 to 600 micromolar (μM) concentrations in primary erythroid progenitors in vitro. Thus, the HbF inducers as disclosed herein have higher potency by at least 1-2 logs. In particular, Desloratidine demonstrates fetal hemoglobin (HbF) inducing activity at concentrations as low as 5 nanomolar (5 nM) to 3 micromolar (3 μM). Benserazide induces fetal globin (HbF) mRNA at concentrations as low as 0.3 to 5 micromolar (0.3-5.0 μM). Resveratrol induces fetal globin (HbF) and inhibits histone deacetylases at 0.05 micromolar (0.05 μM) as compared to other histone deacetylase inhibitors which act at 1 millimolar (1 mM) concentrations (butyrate).

Example 4

Figure 13:
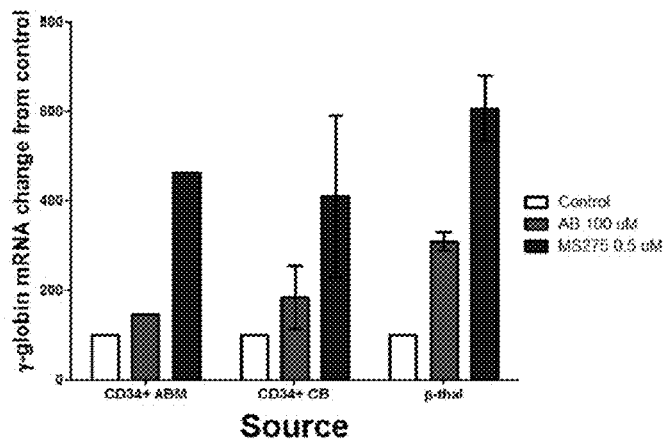
FIG. 13 shows a histogram of γ-globin induction by MS-275 (0.5 μM) is greater than by arginine butyrate (100 μM) in erythroid progenitors cultured from human sources with low or high basal HbF levels.
Figure 14:
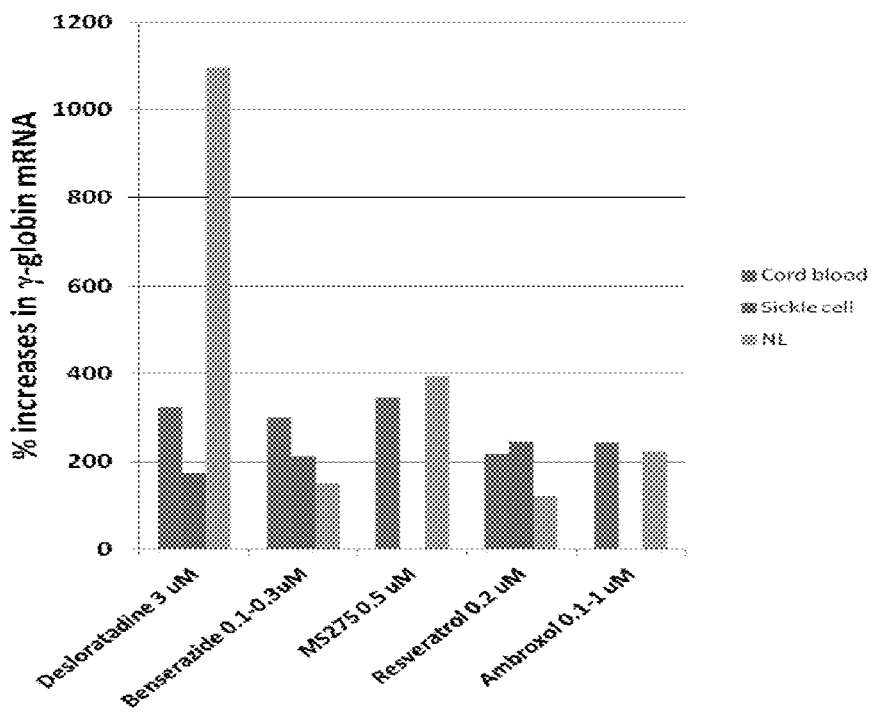
FIG. 14 shows a histogram of fetal globin mRNA in primary erythroid progenitor cells treated with the candidate HbF-inducing agents, compared to untreated control cultures from the same subject, from different human sources of erythroid cells. The numbers represent % of control fetal globin.

In erythroid progenitors cultured from human sources with low or high basal HbF levels, MS-275 demonstrates higher activity than Arginine Butyrate (FIG. 13). This demonstrated that MS-275 is active in a variety of patients with beta hemoglobin disorders. Table 2 shows that expression of fetal globin mRNA in erythroid cells treated with the candidate therapeutics, compared to untreated control cultures from the same subject, from different human sources of erythroid cells. The numbers represent % of control fetal globin. The findings indicate that fetal globin mRNA is induced regardless of basal levels of expression, (low expression occurs in normal adults cells).

TABLE 2

Effect of agents on Erythroid Progenitors

| Source of progenitors | Cord Blood | Hemoglobin disorder | Normal |
|---|---|---|---|
| Desloratadine 3 uM | 4/4 responses | 3/3 responses | 1 response |
| Mean: | 323 | 175 | 1098 |
| | 600 | 135 (CC) | (ABM) |
| | 260 | 274.2 (CD) | |
| | 220 | 121 (CC) | |
| | 213 | 123 (CH) | |
| Benserazide 0.1-0.3 uM | 4/5 | 4/4 | 3/4 |
| Mean: | 300 | 212 | 151 |
| | 475 | 178 (CC) | 115 MB) |
| | 356 | 143 (CC) | 223 (JS) |
| | 187 | 282 (CH) | 114 (ABM) |
| | 183 | 128 (MLB) | |
| | | 277.3 (CD) | |
| MS275 0.5 uM | 2/2 | | 5/6 |
| Mean: | 345 | | 394 |
| | 228 | | 680 (MB) |
| | 463 | | 534 (MB) |
| | | | 168 (JS) |
| | | | 463 (ABM) |
| | | | 126 (ABM) |
| Resveratrol 0.2 uM | 5/5 | 1/2 | 1/2 |
| Mean: | 217 | 245 | 122 |
| | 378 | | |
| | 147 | | |
| | 122 | | |
| | 254 | | |
| | 186 | | |
| Ambroxol 0.1-1 uM | 3/4 | | 1/1 |
| Means: | 243 | | 224 |
| | 302 | | |
| | 233 | | |
| | 193 | | |

Example 5

Desloratidine was administered to an adult human subject with alpha thalassemia trait at a standard allergy treatment dose of 5 mg/day total, once per day. Hemoglobin increased from 10 to 11.5 g/gl and hematocrit, a measure of red blood cells, increased from 30% to 35% within 4 weeks. This is an unexpected and rapid rise in red blood cell levels in a mildly anemic subject. Accordingly, the inventors have discovered that desloratidine can be used to increase red blood cells in a subject at a dose of at least about 35 mg/day or any range between about 35 mg/day and 150 mg/kg day in order to increase the red blood levels in a subject in need of treatment. In some embodiments, the subject who is administered desloratidine is selected to have a low red blood count, or is anaemic or has a cytopenia as disclosed herein.

REFERENCES

All references cited in the specification and Examples are incorporated herein in their entirety by reference.

Perrine S P Perrine S P, Castaneda S, Chui D H K, Faller D V, Berenson R, Fuchareon S. Fetal globin gene inducers: novel agents and new potential. Ann NY Acad Sci, 1202: 158-164, 2010.

Steinberg M H & Rodgers G P. Pharmacologic modulation of fetal hemoglobin. Medicine 80:328-44, 2001.

Steinberg M H. Sickle cell Anemia, the First Molecular Disease: overview of molecular etiology pathophysiology, and therapeutic approaches. The Scientific World 8: 1295-1324,2008.

Weatherall D J. The inherited diseases of hemoglobin are an emerging global health burden. Blood. 115: 4331-4336, 2010.

Perrine S P. Fetal globin stimulant therapies in the beta-hemoglobinopathies: principles and current potential. Pediatr Ann. 2008; 37:339-346.

Steinberg M H. Predicting the clinical severity of sickle cell disease. Br. J. Haematol. 129:465-81, 2005.

Mork, C A, Spanjaard, R A, and Faller D V. A mechanistic approach to anticancer therapy: targeting the cell cycle with histone deacetylase inhibitors. Current Reviews in Pharmacology, 2005, 11:1091-1104.

Wittich S, Scherf H, Xie C, Heltweg B, Dequiedt F, Verdin E, Gerhauser C, Jung M. Effect of inhibitors of histone deacetylase on the induction of cell differentiation in murine and human erythroleukemia cell lines. Anticancer Drugs. 2005 July; 16(6):635-43.

Cao H, Stamatoyannopoulos G, Jung M. Induction of human gamma globin gene expression by histone deacetylase inhibitors. Blood. 2004 Jan. 15; 103(2):701-9.

Perrine S P, Ginder G D, Faller D V, Dover G J, Ikuta T, et al. A short-term trial of butyrate to stimulate fetal globin gene expression in the beta globin gene disorders. N Eng J Med 1993; 328:81-86.

Atweh G F, Sutton M, Nassif I, Boosalis V, Dover G J, Wright E, Wallenstein S, McMahon L, Stamatoyannopoulos G, Faller D V, Perrine S P. Sustained induction of fetal hemoglobin by pulse butyrate therapy in sickle cell disease. Blood 1999. 93(6):1790-1797.

Goldberg, M. A., Husson, M. A., and Bunn, H. F. Participation of hemoglobins A and F in polymerization of sickle hemoglobin. J. Biol. Chem., 252: 3414-3421, 1977

The invention claimed is:

1. A method for increasing the percentage or absolute amount of fetal hemoglobin in the blood of a subject, comprising administering to the subject a pharmaceutical composition comprising 2 amino-3-hydroxy-N'-(2,3,4-trihydroxy-benzyl)propanehydrazide (benserazide), or 8-Chloro-6,11-dihydro-11-(4-piperidinylidene)-5H-benzo[5,6]cyclohepta[1,2-b]pyridine (desloratadine) or both, or a pharmaceutically acceptable salt or ester thereof, wherein the dose of benserazide or desloratadine is equal to or less than 2 mg/kg/day, and wherein after administration, the percentage of fetal hemoglobin in the blood of the subject increases.

2. The method of claim 1, where the composition further comprises at least one of a fetal hemoglobin-inducing agent selected from the group consisting of: ambroxol, resveratrol, 2,3-bis-[(2-Hydroxyethyl)thio]-1,4 naphthoquinone (NSC-95397), idarubicin, or auronafin or N-(2-aminophenyl)-4-[N-(pyridin-3-yl-methoxycarbonyl)aminomethyl]benzamide (MS-275), and a combination thereof.

3. The method of claim 1, further comprising administering to the subject 2,2-dimethylbutyrate or N-(2-aminophenyl)-4-[N-(pyridin-3-yl-methoxycarbonyl)aminomethyl]benzamide (MS-275).

4. The method of claim 1, further comprising administering to the subject hydroxyurea (HU), a histone deacetylase (HDAC) inhibitor or a combination thereof.

5. The method of claim 1, wherein the subject has been diagnosed with a blood disorder or anemia.

6. The method of claim 1, wherein the blood disorder is sickle cell syndrome, α-Thalassemia, or a -Thalassemia syndrome, or HbE thalassemia.

7. The method of claim 1, wherein the blood disorder is caused by radiation therapy or chemotherapy.

8. The method of claim 1, wherein the percentage or absolute number, or the percentage and absolute number of reticulocytes increases in the blood of the subject.

9. The method of claim 1, wherein the amount of hemoglobin or the percentage of hematocrit, or the amount of hemoglobin and the percentage of hematocrit increases in the blood of the subject.

10. The method of claim 1, wherein the red blood cell production increases.

11. The method of claim 1, where the composition is administered by pulse administration.

12. The method of claim 1, wherein the subject is a human.

13. The method of claim 12, wherein the human is a child.

14. A method of treating a subject with a blood disorder due to a defect or disease in hemoglobin producing red blood cells or the production of hemoglobin, comprising: administering to the subject determined to have a blood disorder, a pharmaceutical composition comprising 2 amino-3-hydroxy-N'-(2,3,4-trihydroxybenzyl)propanehydrazide (benserazide), or 8-Chloro-6,11-dihydro-11-(4-piperidinylidene)-5H-benzo[5,6]cyclohepta[1,2-b]pyridine (desloratadine) or both, or a pharmaceutically acceptable salt or ester thereof, wherein the dose of benserazide or desloratadine is equal to or less than 2 mg/kg/day, to increase the percentage or absolute amount of fetal hemoglobin in the blood or increase the absolute number of red blood cells and/or total hemoglobin to treat the blood disorder in the subject.

15. The method of claim 14, wherein administration of the composition increases the percentage of fetal hemoglobin in the blood of the subject.

16. The method of claim 14, wherein the blood disorder is an anemia, a red blood cell cytopenia, a hemoglobinopathy, a sickle cell syndrome or a β-Thalassemia syndrome, or HbE β thalassemia.

17. The method of claim 14, wherein the subject is a human.

18. The method of claim 17, wherein the human is a child or a human under the age of 2 years.

19. The method of claim 1, wherein 8-Chloro-6,11-dihydro-11-(4-piperidinylidene)-5H-benzo[5,6]cyclohepta[1,2-b]pyridine (desloratidine) is administered in a dose of at least 5 nM or at least 0.2 mg/kg.

20. The method of claim 1, wherein 2-amino-3-hydroxy-N'-(2,3,4-trihydroxybenzyl)propanehydrazide (benserazide) is administered in a dose of at least 0.3 μM or at least 0.5 mg/kg.

21. The method of claim 2 or 3, wherein N-(2-aminophenyl)-4-[N-(pyridin-3-yl-methoxycarbonyl)aminomethyl]benzamide (MS-275) is administered in a dose of between 0.1 mg/kg and 2 mg/kg.

22. The method of claim 1, wherein the subject is administered the pharmaceutical composition orally.

23. The method of claim 11, wherein the interval between pulsed administration of the composition is at least 3 days.

24. The method of claim 11, wherein the interval between pulsed administration of the composition is at least 7 days.

25. The method of claim 11, wherein the interval between pulsed administration of the composition is between 7 days and 3 weeks.

* * * * *